(12) United States Patent
Mirkov et al.

(10) Patent No.: US 12,193,734 B2
(45) Date of Patent: Jan. 14, 2025

(54) PICOSECOND OPTICAL RADIATION SYSTEMS AND METHODS OF USE

(71) Applicant: CYNOSURE, LLC, Westford, MA (US)

(72) Inventors: Mirko Georgiev Mirkov, Chelmsford, MA (US); Rafael Armando Sierra, Palmer, MA (US)

(73) Assignee: CYNOSURE, LLC, Westford, MA (US)

( * ) Notice: Subject to any disclaimer, the term of this patent is extended or adjusted under 35 U.S.C. 154(b) by 0 days.

(21) Appl. No.: 17/886,685

(22) Filed: Aug. 12, 2022

(65) Prior Publication Data

US 2022/0387105 A1 Dec. 8, 2022

Related U.S. Application Data

(63) Continuation of application No. 17/013,082, filed on Sep. 4, 2020, now Pat. No. 11,446,086, which is a
(Continued)

(51) Int. Cl.
*A61B 18/20* (2006.01)
*A61N 5/06* (2006.01)
(Continued)

(52) U.S. Cl.
CPC .......... *A61B 18/203* (2013.01); *A61N 5/0616* (2013.01); *H01S 3/0627* (2013.01);
(Continued)

(58) Field of Classification Search
CPC .......... A61B 18/203; A61B 2018/0047; A61N 5/0616; A61N 5/067; H01S 3/0627;
(Continued)

(56) References Cited

U.S. PATENT DOCUMENTS 853,033 A 5/1907 Roberts
1,590,283 A 6/1926 Catlin
(Continued)

FOREIGN PATENT DOCUMENTS

AT 400305 4/1995
AU 1851583 3/1984
(Continued)

OTHER PUBLICATIONS

US 6,230,044 B1, 05/2001, Afanassieva et al. (withdrawn)
(Continued)

*Primary Examiner* — Xinning(Tom) Niu
(74) *Attorney, Agent, or Firm* — K&L GATES LLP

(57) ABSTRACT

Methods, systems and apparatus are disclosed for delivery of pulsed treatment radiation by employing a pump radiation source generating picosecond pulses at a first wavelength, and a frequency-shifting resonator having a lasing medium and resonant cavity configured to receive the picosecond pulses from the pump source at the first wavelength and to emit radiation at a second wavelength in response thereto, wherein the resonant cavity of the frequency-shifting resonator has a round trip time shorter than the duration of the picosecond pulses generated by the pump radiation source. Methods, systems and apparatus are also disclosed for providing beam uniformity and a sub-harmonic resonator.

34 Claims, 15 Drawing Sheets

Related U.S. Application Data continuation of application No. 16/363,655, filed on Mar. 25, 2019, now Pat. No. 10,765,478, which is a continuation of application No. 14/340,961, filed on Jul. 25, 2014, now Pat. No. 10,245,107, which is a continuation of application No. 14/216,353, filed on Mar. 17, 2014, now Pat. No. 10,285,757.

(60) Provisional application No. 61/891,299, filed on Oct. 15, 2013, provisional application No. 61/789,144, filed on Mar. 15, 2013.

(51) Int. Cl.
| | |
|---|---|
| *H01S 3/06* | (2006.01) |
| *H01S 3/08018* | (2023.01) |
| *H01S 3/094* | (2006.01) |
| *H01S 3/102* | (2006.01) |
| *H01S 3/1106* | (2023.01) |
| *H01S 3/1109* | (2023.01) |
| *A61B 18/00* | (2006.01) |
| *A61N 5/067* | (2006.01) |
| *H01S 3/00* | (2006.01) |
| *H01S 3/08* | (2023.01) |
| *H01S 3/093* | (2006.01) |
| *H01S 3/107* | (2006.01) |
| *H01S 3/16* | (2006.01) |

(52) U.S. Cl.
CPC .... *H01S 3/08018* (2013.01); *H01S 3/094076* (2013.01); *H01S 3/1024* (2013.01); *H01S 3/1106* (2013.01); *H01S 3/1109* (2013.01); *H01S 3/1121* (2013.01); *A61B 2018/0047* (2013.01); *A61N 5/067* (2021.08); *H01S 3/0092* (2013.01); *H01S 3/08054* (2013.01); *H01S 3/093* (2013.01); *H01S 3/094038* (2013.01); *H01S 3/094084* (2013.01); *H01S 3/107* (2013.01); *H01S 3/1611* (2013.01); *H01S 3/1623* (2013.01); *H01S 3/1633* (2013.01); *H01S 3/1643* (2013.01); *H01S 3/1673* (2013.01)

(58) Field of Classification Search
CPC ........... H01S 3/08018; H01S 3/094076; H01S 3/1024; H01S 3/1106; H01S 3/1109; H01S 3/1121; H01S 3/0092; H01S 3/08054; H01S 3/093; H01S 3/094038; H01S 3/094084; H01S 3/107; H01S 3/1611; H01S 3/1623; H01S 3/1633; H01S 3/1643; H01S 3/1673
See application file for complete search history.

(56) References Cited

U.S. PATENT DOCUMENTS

| | | |
|---|---|---|
| 1,676,183 A | 7/1928 | Garfunkle |
| 1,706,161 A | 3/1929 | Hollnagen |
| 2,068,721 A | 1/1937 | Wappler et al. |
| 2,472,385 A | 6/1949 | Rollman |
| 2,669,771 A | 2/1954 | Burge et al. |
| 3,243,650 A | 3/1966 | Hawkins et al. |
| 3,261,978 A | 7/1966 | Brenman |
| 3,284,665 A | 11/1966 | Goncz |
| 3,327,712 A | 6/1967 | Kaufmann |
| 3,465,203 A | 9/1969 | Michaels et al. |
| 3,486,070 A | 12/1969 | Engel |
| 3,524,144 A | 8/1970 | Buser et al. |
| 3,527,932 A | 9/1970 | Thomas |
| 3,538,919 A | 11/1970 | Meyer |
| 3,597,652 A | 8/1971 | Gates, Jr. |
| 3,622,743 A | 11/1971 | Muncheryan |
| 3,651,425 A | 3/1972 | McKnight |
| 3,653,778 A | 4/1972 | Freiling |
| 3,667,454 A | 6/1972 | Prince |
| 3,693,623 A | 9/1972 | Harte et al. |
| 3,699,967 A | 10/1972 | Anderson |
| 3,725,733 A | 4/1973 | Mack et al. |
| 3,766,393 A | 10/1973 | Herzog et al. |
| 3,766,488 A | 10/1973 | Kohn |
| 3,769,963 A | 11/1973 | Goldman et al. |
| 3,793,723 A | 2/1974 | Kuris et al. |
| 3,794,028 A | 2/1974 | Mueller et al. |
| 3,815,046 A | 6/1974 | Johnson et al. |
| 3,818,373 A | 6/1974 | Chun et al. |
| 3,818,914 A | 6/1974 | Bender |
| 3,821,510 A | 6/1974 | Muncheryan |
| 3,834,391 A | 9/1974 | Block |
| 3,843,865 A | 10/1974 | Nath |
| 3,846,811 A | 11/1974 | Nakamura et al. |
| 3,857,015 A | 12/1974 | Clark et al. |
| 3,858,577 A | 1/1975 | Bass et al. |
| 3,861,921 A | 1/1975 | Hoffmann et al. |
| 3,885,569 A | 5/1975 | Judson |
| 3,890,537 A | 6/1975 | Park et al. |
| 3,900,034 A | 8/1975 | Katz et al. |
| 3,909,649 A | 9/1975 | Arsena |
| 3,914,709 A | 10/1975 | Pike et al. |
| 3,939,560 A | 2/1976 | Lyall |
| 3,977,083 A | 8/1976 | Leslie et al. |
| 3,980,861 A | 9/1976 | Fukunaga |
| 4,019,156 A | 4/1977 | Fountain et al. |
| 4,037,136 A | 7/1977 | Hoene |
| 4,038,984 A | 8/1977 | Sittner |
| 4,047,106 A | 9/1977 | Robinson |
| 4,065,370 A | 12/1977 | Noble et al. |
| 4,122,853 A | 10/1978 | Smith |
| 4,133,503 A | 1/1979 | Bliss |
| 4,139,342 A | 2/1979 | Sheldrake et al. |
| 4,154,240 A | 5/1979 | Ikuno et al. |
| 4,176,324 A | 11/1979 | Aldag et al. |
| 4,180,751 A * | 12/1979 | Ammann ................. G02F 1/39 359/330 |
| 4,188,927 A | 2/1980 | Harris |
| 4,213,462 A | 2/1980 | Sato |
| 4,228,800 A | 10/1980 | Degler, Jr. et al. |
| 4,233,493 A | 11/1980 | Nath et al. |
| 4,254,333 A | 3/1981 | Bergstrom |
| 4,259,123 A | 3/1981 | Tymkewicz |
| 4,269,067 A | 5/1981 | Tynan et al. |
| 4,273,109 A | 6/1981 | Enderby |
| 4,275,335 A | 6/1981 | Ishida et al. |
| 4,291,281 A | 9/1981 | Pinard et al. |
| 4,292,601 A | 9/1981 | Aldag et al. |
| 4,293,827 A | 10/1981 | McAllister et al. |
| 4,298,005 A | 11/1981 | Mutzhas |
| 4,299,912 A | 11/1981 | Shiba et al. |
| 4,302,730 A | 11/1981 | Jernigan |
| 4,313,431 A | 2/1982 | Frank |
| 4,316,467 A | 2/1982 | Muckerheide |
| 4,333,197 A | 6/1982 | Kuris |
| 4,335,726 A | 6/1982 | Kolstedt |
| 4,336,809 A | 6/1982 | Clark |
| 4,364,015 A | 12/1982 | Drake et al. |
| 4,375,684 A | 5/1983 | Everett |
| 4,388,924 A | 6/1983 | Weissman et al. |
| 4,409,479 A | 10/1983 | Sprague et al. |
| 4,428,368 A | 1/1984 | Torii |
| 4,435,808 A | 3/1984 | Javan |
| 4,445,217 A | 4/1984 | Acharekar et al. |
| 4,452,081 A | 6/1984 | Seppi |
| 4,456,872 A | 6/1984 | Froeschle |
| 4,461,294 A | 7/1984 | Baron |
| 4,488,104 A | 12/1984 | Suzuki |
| 4,489,415 A | 12/1984 | Jones et al. |
| 4,492,601 A | 1/1985 | Nakasone et al. |
| 4,503,854 A | 3/1985 | Jako |
| 4,504,727 A | 3/1985 | Melcher et al. |
| 4,512,197 A | 4/1985 | von Gutfeld et al. |
| 4,524,289 A | 6/1985 | Hammond et al. |

(56) References Cited

U.S. PATENT DOCUMENTS

| | | | |
|---|---|---|---|
| 4,539,987 | A | 9/1985 | Nath et al. |
| 4,553,546 | A | 11/1985 | Javelle |
| 4,555,786 | A | 11/1985 | Byer |
| 4,556,979 | A | 12/1985 | Scott et al. |
| 4,559,943 | A | 12/1985 | Bowers |
| 4,561,440 | A | 12/1985 | Kubo et al. |
| 4,566,271 | A | 1/1986 | French et al. |
| 4,566,438 | A | 1/1986 | Liese et al. |
| 4,569,345 | A | 2/1986 | Manes |
| 4,576,177 | A | 3/1986 | Webster, Jr. |
| 4,587,968 | A | 5/1986 | Price |
| 4,591,762 | A | 5/1986 | Nakamura |
| 4,592,353 | A | 6/1986 | Daikuzono |
| 4,601,037 | A | 7/1986 | McDonald |
| 4,601,753 | A | 7/1986 | Soileau et al. |
| 4,608,978 | A | 9/1986 | Rohr |
| 4,608,979 | A | 9/1986 | Breidenthal et al. |
| 4,617,926 | A | 10/1986 | Sutton |
| 4,623,929 | A | 11/1986 | Johnson et al. |
| 4,629,884 | A | 12/1986 | Bergstrom |
| 4,638,800 | A | 1/1987 | Michel |
| 4,653,495 | A | 3/1987 | Nanaumi |
| 4,656,641 | A | 4/1987 | Scifres et al. |
| 4,662,368 | A | 5/1987 | Hussein et al. |
| 4,677,347 | A | 6/1987 | Nakamura |
| 4,686,986 | A | 8/1987 | Fenyo et al. |
| 4,693,244 | A | 9/1987 | Daikuzono |
| 4,693,556 | A | 9/1987 | McCaughan, Jr. |
| 4,695,697 | A | 9/1987 | Kosa |
| 4,710,677 | A | 12/1987 | Halberstadt et al. |
| 4,718,416 | A | 1/1988 | Nanaumi |
| 4,723,248 | A * | 2/1988 | Harter .............. H01S 3/1061 372/41 |
| 4,724,835 | A | 2/1988 | Liss et al. |
| 4,733,660 | A | 3/1988 | Itzkan |
| 4,735,201 | A | 4/1988 | O'Reilly |
| 4,736,743 | A | 4/1988 | Daikuzono |
| 4,736,745 | A | 4/1988 | Gluckman |
| 4,740,047 | A | 4/1988 | Abe et al. |
| 4,741,338 | A | 5/1988 | Miyamae |
| 4,745,909 | A | 5/1988 | Pelton et al. |
| 4,747,660 | A | 5/1988 | Nishioka et al. |
| 4,749,913 | A | 6/1988 | Stuermer et al. |
| 4,759,349 | A | 7/1988 | Betz et al. |
| 4,773,413 | A | 9/1988 | Hussein et al. |
| 4,775,361 | A | 10/1988 | Jacques et al. |
| 4,779,173 | A | 10/1988 | Carr et al. |
| 4,784,135 | A | 11/1988 | Blum et al. |
| 4,799,479 | A | 1/1989 | Spears |
| 4,813,412 | A | 3/1989 | Yamazaki et al. |
| 4,813,762 | A | 3/1989 | Leger et al. |
| 4,819,669 | A | 4/1989 | Politzer |
| 4,826,431 | A | 5/1989 | Fujimura et al. |
| 4,829,262 | A | 5/1989 | Furumoto |
| 4,832,024 | A | 5/1989 | Boussignac et al. |
| 4,840,174 | A | 6/1989 | Gluckman |
| 4,840,563 | A | 6/1989 | Altendorf |
| 4,845,608 | A | 7/1989 | Gdula |
| 4,848,339 | A | 7/1989 | Rink et al. |
| 4,852,107 | A | 7/1989 | Hamal et al. |
| 4,852,549 | A | 8/1989 | Mori |
| 4,860,172 | A | 8/1989 | Schlager et al. |
| 4,860,303 | A | 8/1989 | Russell |
| 4,860,743 | A | 8/1989 | Abela |
| 4,860,744 | A | 8/1989 | Johnson et al. |
| 4,862,886 | A | 9/1989 | Clarke et al. |
| 4,862,888 | A | 9/1989 | Yessik |
| 4,862,903 | A | 9/1989 | Campbell |
| 4,871,479 | A | 10/1989 | Bachelard et al. |
| 4,878,224 | A | 10/1989 | Kuder |
| 4,884,560 | A | 12/1989 | Kuracina |
| 4,887,600 | A | 12/1989 | Watson et al. |
| 4,889,525 | A | 12/1989 | Yuhas et al. |
| 4,890,898 | A | 1/1990 | Bentley et al. |
| 4,891,817 | A | 1/1990 | Duarte |
| 4,896,329 | A | 1/1990 | Knaak |
| 4,898,438 | A | 2/1990 | Mori |
| 4,898,439 | A | 2/1990 | Mori |
| 4,901,323 | A | 2/1990 | Hawkins et al. |
| 4,905,690 | A | 3/1990 | Ohshiro et al. |
| 4,910,438 | A | 3/1990 | Farnsworth |
| 4,913,142 | A | 4/1990 | Kittrell et al. |
| 4,914,298 | A | 4/1990 | Quad et al. |
| 4,917,084 | A | 4/1990 | Sinofsky |
| 4,926,227 | A | 5/1990 | Jensen |
| 4,928,038 | A | 5/1990 | Nerone |
| 4,930,504 | A | 6/1990 | Diamantopoulos |
| 4,931,053 | A | 6/1990 | L'Esperance |
| 4,932,954 | A | 6/1990 | Wondrazek et al. |
| 4,945,239 | A | 7/1990 | Wist et al. |
| 4,950,266 | A | 8/1990 | Sinofsky |
| 4,955,882 | A | 9/1990 | Hakky |
| 4,968,314 | A | 11/1990 | Michaels |
| 4,972,427 | A | 11/1990 | Streifer et al. |
| 4,973,848 | A | 11/1990 | Kolobanov et al. |
| 4,976,308 | A | 12/1990 | Faghri |
| 4,976,709 | A | 12/1990 | Sand |
| 4,977,571 | A | 12/1990 | Furumoto et al. |
| 4,978,186 | A | 12/1990 | Mori |
| 4,979,180 | A | 12/1990 | Muncheryan |
| 4,992,256 | A | 2/1991 | Skaggs et al. |
| 4,994,060 | A | 2/1991 | Rink et al. |
| 5,000,752 | A | 3/1991 | Hoskin et al. |
| 5,006,293 | A | 4/1991 | Hartman et al. |
| 5,009,658 | A | 4/1991 | Damgaard-Iversen |
| 5,011,483 | A | 4/1991 | Sleister |
| 5,027,359 | A | 6/1991 | Leger et al. |
| 5,030,090 | A | 7/1991 | Maeda et al. |
| 5,032,178 | A | 7/1991 | Cornell |
| 5,037,421 | A | 8/1991 | Boutacoff et al. |
| 5,041,109 | A | 8/1991 | Abela |
| 5,046,494 | A | 9/1991 | Searfoss et al. |
| 5,050,597 | A | 9/1991 | Daikuzono |
| 5,056,515 | A | 10/1991 | Abel |
| 5,057,099 | A | 10/1991 | Rink |
| 5,057,104 | A | 10/1991 | Chess |
| 5,059,192 | A | 10/1991 | Zaias |
| 5,061,266 | A | 10/1991 | Hakky |
| 5,060,243 | A | 11/1991 | Furumoto |
| 5,065,515 | A | 11/1991 | Iderosa |
| 5,066,292 | A | 11/1991 | Müller et al. |
| 5,066,293 | A | 11/1991 | Furumoto |
| 5,071,416 | A | 12/1991 | Heller et al. |
| 5,071,417 | A | 12/1991 | Sinofsky |
| 5,079,772 | A | 1/1992 | Negus et al. |
| 5,080,660 | A | 1/1992 | Buelna |
| 5,090,019 | A | 2/1992 | Scheps |
| 5,092,865 | A | 3/1992 | Rink |
| 5,099,231 | A | 3/1992 | Sato |
| 5,102,410 | A | 4/1992 | Dressel |
| 5,108,388 | A | 4/1992 | Trokel |
| 5,109,387 | A | 4/1992 | Garden et al. |
| 5,112,328 | A | 5/1992 | Taboada et al. |
| 5,127,395 | A | 7/1992 | Bontemps |
| 5,129,896 | A | 7/1992 | Hasson |
| 5,129,897 | A | 7/1992 | Daikuzono |
| 5,132,980 | A | 7/1992 | Connors et al. |
| 5,133,102 | A | 7/1992 | Sakuma |
| 5,137,530 | A | 8/1992 | Sand |
| 5,140,608 | A | 8/1992 | Karpol et al. |
| 5,140,984 | A | 8/1992 | Dew et al. |
| 5,147,353 | A | 9/1992 | Everett |
| 5,147,356 | A | 9/1992 | Bhatta |
| 5,151,097 | A | 9/1992 | Daikuzono |
| 5,159,601 | A | 10/1992 | Huber |
| 5,160,194 | A | 11/1992 | Feldman |
| 5,163,935 | A | 11/1992 | Black et al. |
| 5,171,564 | A | 12/1992 | Nathoo et al. |
| 5,178,617 | A | 1/1993 | Kuizenga et al. |
| 5,180,378 | A | 1/1993 | Kung et al. |
| 5,182,557 | A | 1/1993 | Lang |
| 5,182,857 | A | 2/1993 | Simon |
| 5,190,541 | A | 3/1993 | Abele et al. |
| 5,191,883 | A | 3/1993 | Lennox et al. |

(56) References Cited

U.S. PATENT DOCUMENTS

| | | |
|---|---|---|
| 5,192,278 A | 3/1993 | Hayes et al. |
| 5,196,004 A | 3/1993 | Sinofsky |
| 5,197,470 A | 3/1993 | Helfer et al. |
| 5,201,731 A | 4/1993 | Hakky |
| 5,193,526 A | 5/1993 | Daikuzono |
| 5,207,671 A | 5/1993 | Franken et al. |
| 5,207,672 A | 5/1993 | Roth et al. |
| 5,207,673 A | 5/1993 | Ebling et al. |
| 5,209,748 A | 5/1993 | Daikuzono |
| 5,213,092 A | 5/1993 | Uram |
| 5,217,455 A | 6/1993 | Tan |
| 5,219,347 A | 6/1993 | Negus et al. |
| 5,222,907 A | 6/1993 | Katabuchi et al. |
| 5,222,953 A | 6/1993 | Dowlatshaki |
| 5,225,926 A | 7/1993 | Cuomo et al. |
| 5,226,907 A | 7/1993 | Tankovich |
| 5,242,437 A | 9/1993 | Everett et al. |
| 5,242,438 A | 9/1993 | Saadatmanesh |
| 5,246,436 A | 9/1993 | Rowe |
| 5,249,192 A | 9/1993 | Kuizenga et al. |
| 5,254,114 A | 10/1993 | Reed, Jr. et al. |
| 5,255,277 A | 10/1993 | Carvalho |
| 5,257,970 A | 11/1993 | Dougherty |
| 5,257,991 A | 11/1993 | Fletcher et al. |
| 5,261,904 A | 11/1993 | Baker et al. |
| 5,267,399 A | 12/1993 | Johnston |
| 5,267,995 A | 12/1993 | Doiron et al. |
| 5,267,998 A | 12/1993 | Hagen |
| 5,269,777 A | 12/1993 | Doiron et al. |
| 5,269,780 A | 12/1993 | Roos |
| 5,281,211 A | 1/1994 | Parel et al. |
| 5,281,216 A | 1/1994 | Klicek |
| 5,282,797 A | 2/1994 | Chess |
| 5,284,154 A | 2/1994 | Raymond et al. |
| 5,287,372 A | 2/1994 | Ortiz |
| 5,287,380 A | 2/1994 | Hsia |
| 5,290,273 A | 3/1994 | Tan |
| 5,290,274 A | 3/1994 | Levy et al. |
| 5,292,320 A | 3/1994 | Brown et al. |
| 5,293,880 A | 3/1994 | Levitt |
| 5,300,063 A | 4/1994 | Tano et al. |
| 5,300,065 A | 4/1994 | Anderson |
| 5,300,097 A | 4/1994 | Lerner et al. |
| 5,303,585 A | 4/1994 | Lichte |
| 5,304,167 A | 4/1994 | Freiberg |
| 5,304,170 A | 4/1994 | Green |
| 5,304,173 A | 4/1994 | Kittrell et al. |
| 5,306,143 A | 4/1994 | Levy |
| 5,306,274 A | 4/1994 | Long |
| 5,307,369 A | 4/1994 | Kimberlin |
| 5,308,311 A | 5/1994 | Eggers et al. |
| 5,312,395 A | 5/1994 | Tan et al. |
| 5,312,396 A | 5/1994 | Feld et al. |
| 5,320,618 A | 6/1994 | Gustafsson |
| 5,320,620 A | 6/1994 | Long et al. |
| 5,330,470 A | 7/1994 | Hagen |
| 5,331,649 A | 7/1994 | Dacquay et al. |
| 5,334,191 A | 8/1994 | Poppas et al. |
| 5,334,193 A | 8/1994 | Nardella |
| 5,336,217 A | 8/1994 | Buys et al. |
| 5,336,221 A | 8/1994 | Anderson |
| 5,342,358 A | 8/1994 | Daikuzono et al. |
| 5,344,418 A | 9/1994 | Ghaffari |
| 5,344,434 A | 9/1994 | Talmore |
| 5,346,488 A | 9/1994 | Prince et al. |
| 5,348,551 A | 9/1994 | Spears et al. |
| 5,349,590 A | 9/1994 | Amirkhanian et al. |
| 5,350,376 A | 9/1994 | Brown |
| 5,353,020 A | 10/1994 | Schurmann |
| 5,353,790 A | 10/1994 | Jacques et al. |
| 5,354,294 A | 10/1994 | Chou |
| 5,356,081 A | 10/1994 | Sellar |
| 5,358,503 A | 10/1994 | Bertwell et al. |
| 5,360,426 A | 11/1994 | Muller et al. |
| 5,366,456 A | 11/1994 | Rink et al. |
| 5,368,031 A | 11/1994 | Cline et al. |
| 5,368,038 A | 11/1994 | Fraden |
| 5,369,496 A | 11/1994 | Alfano et al. |
| 5,369,831 A | 12/1994 | Bock |
| 5,370,642 A | 12/1994 | Keller |
| 5,370,649 A | 12/1994 | Gardetto et al. |
| 5,380,317 A | 1/1995 | Everett et al. |
| 5,383,876 A | 1/1995 | Nardella |
| 5,386,427 A | 1/1995 | Zayhowski |
| 5,387,211 A | 2/1995 | Saadatmanesh |
| 5,395,356 A | 3/1995 | King et al. |
| 5,403,306 A | 4/1995 | Edwards et al. |
| 5,405,368 A | 4/1995 | Eckhouse |
| 5,409,446 A | 4/1995 | Rattner |
| 5,409,479 A | 4/1995 | Dew et al. |
| 5,409,481 A | 4/1995 | Poppas et al. |
| 5,415,654 A | 5/1995 | Daikuzono |
| 5,421,337 A | 6/1995 | Richards-Kortum |
| 5,421,339 A | 6/1995 | Ramanujam et al. |
| 5,422,112 A | 6/1995 | Williams |
| 5,423,800 A | 6/1995 | Ren et al. |
| 5,423,803 A | 6/1995 | Tankovich et al. |
| 5,423,805 A | 6/1995 | Brucker et al. |
| 5,425,728 A | 6/1995 | Tankovich |
| 5,425,735 A | 6/1995 | Rosen et al. |
| 5,425,754 A | 6/1995 | Braun et al. |
| 5,439,954 A | 8/1995 | Bush |
| 5,441,499 A | 8/1995 | Fritzsch |
| 5,445,608 A | 8/1995 | Chen et al. |
| 5,445,611 A | 8/1995 | Eppstein et al. |
| 5,454,807 A | 10/1995 | Lennox et al. |
| 5,456,682 A | 10/1995 | Edwards et al. |
| 5,458,140 A | 10/1995 | Eppstein et al. |
| 5,464,436 A | 11/1995 | Smith |
| 5,464,724 A | 11/1995 | Akiyama et al. |
| 5,470,331 A | 11/1995 | Daikuzono |
| 5,472,748 A | 12/1995 | Wolfe et al. |
| 5,474,549 A | 12/1995 | Ortiz et al. |
| 5,484,436 A | 1/1996 | Eggers et al. |
| 5,486,170 A | 1/1996 | Winston et al. |
| 5,486,172 A | 1/1996 | Chess |
| 5,488,626 A | 1/1996 | Heller et al. |
| 5,489,256 A | 2/1996 | Adair |
| 5,492,894 A | 2/1996 | Bascom et al. |
| 5,496,305 A | 3/1996 | Kittrell et al. |
| 5,496,307 A | 3/1996 | Daikuzono |
| 5,498,935 A | 3/1996 | McMahan et al. |
| 5,499,313 A | 3/1996 | Kleinerman |
| 5,501,680 A | 3/1996 | Kurtz et al. |
| 5,502,582 A | 3/1996 | Larson et al. |
| 5,505,726 A | 4/1996 | Meserol |
| 5,505,727 A | 4/1996 | Keller |
| 5,507,739 A | 4/1996 | Vassiliadis et al. |
| 5,519,534 A | 5/1996 | Smith et al. |
| 5,521,367 A | 5/1996 | Bard et al. |
| 5,522,813 A | 6/1996 | Trelles |
| 5,527,350 A | 6/1996 | Grove et al. |
| 5,527,368 A | 6/1996 | Supkis et al. |
| 5,530,711 A | 6/1996 | Scheps |
| 5,531,739 A | 7/1996 | Trelles |
| 5,531,740 A | 7/1996 | Black |
| 5,536,168 A | 7/1996 | Bourke |
| 5,540,676 A | 7/1996 | Freiberg |
| 5,540,678 A | 7/1996 | Long et al. |
| 5,540,681 A | 7/1996 | Strul et al. |
| 5,541,948 A | 7/1996 | Krupke et al. |
| 5,546,214 A | 8/1996 | Black et al. |
| 5,549,660 A | 8/1996 | Mendes et al. |
| 5,557,625 A | 9/1996 | Durville |
| 5,558,666 A | 9/1996 | Dewey et al. |
| 5,558,667 A | 9/1996 | Yarborough et al. |
| 5,561,881 A | 10/1996 | Klinger et al. |
| 5,571,098 A | 11/1996 | Domankevitz et al. |
| 5,578,029 A | 11/1996 | Trelles et al. |
| 5,578,866 A | 11/1996 | DePoorter et al. |
| 5,592,327 A | 1/1997 | Gabl et al. |
| 5,595,568 A | 1/1997 | Anderson et al. |
| 5,598,426 A | 1/1997 | Hsia et al. |
| 5,608,210 A | 3/1997 | Esparza et al. |

(56) References Cited

U.S. PATENT DOCUMENTS

| | | |
|---|---|---|
| 5,611,793 A | 3/1997 | Wilson et al. |
| 5,616,140 A | 4/1997 | Prescott |
| 5,618,284 A | 4/1997 | Sand |
| 5,620,478 A | 4/1997 | Eckhouse |
| 5,624,435 A | 4/1997 | Furumoto et al. |
| 5,626,631 A | 5/1997 | Eckhouse |
| 5,628,744 A | 5/1997 | Coleman et al. |
| 5,628,771 A | 5/1997 | Mizukawa et al. |
| 5,630,811 A | 5/1997 | Miller |
| 5,632,741 A | 5/1997 | Zavislan et al. |
| 5,634,711 A | 6/1997 | Kennedy et al. |
| 5,647,866 A | 7/1997 | Zaias et al. |
| 5,649,972 A | 7/1997 | Hochstein |
| 5,651,783 A | 7/1997 | Reynard |
| 5,652,481 A | 7/1997 | Johnson et al. |
| 5,653,706 A | 8/1997 | Zavislan et al. |
| 5,655,547 A | 8/1997 | Karni |
| 5,657,760 A | 8/1997 | Ying et al. |
| 5,658,148 A | 8/1997 | Neuberger et al. |
| 5,658,323 A | 8/1997 | Miller |
| 5,660,836 A | 8/1997 | Knowlton |
| 5,661,744 A | 8/1997 | Murakami et al. |
| 5,662,643 A | 9/1997 | Kung et al. |
| 5,662,644 A | 9/1997 | Swor |
| 5,668,824 A | 9/1997 | Furumoto |
| 5,671,315 A | 9/1997 | Tabuchi et al. |
| 5,673,451 A | 10/1997 | Moore et al. |
| 5,679,113 A | 10/1997 | Caisey et al. |
| 5,683,380 A | 11/1997 | Eckhouse et al. |
| 5,684,902 A | 11/1997 | Tada |
| 5,688,266 A | 11/1997 | Edwards et al. |
| 5,688,267 A | 11/1997 | Panescu et al. |
| 5,692,509 A | 12/1997 | Voss et al. |
| 5,698,866 A | 12/1997 | Doiron et al. |
| 5,707,369 A | 1/1998 | Vaitekunas et al. |
| 5,707,401 A | 1/1998 | Martin et al. |
| 5,707,403 A | 1/1998 | Grove et al. |
| 5,713,738 A | 2/1998 | Yarborough |
| 5,714,119 A | 2/1998 | Kawagoe et al. |
| 5,720,772 A | 2/1998 | Eckhouse |
| 5,722,397 A | 3/1998 | Eppstein |
| 5,725,522 A | 3/1998 | Sinofsky |
| 5,728,090 A | 3/1998 | Martin et al. |
| 5,735,844 A | 4/1998 | Anderson et al. |
| 5,735,884 A | 4/1998 | Thompson et al. |
| 5,738,678 A | 4/1998 | Patel |
| 5,742,392 A | 4/1998 | Anderson et al. |
| 5,743,901 A | 4/1998 | Grove et al. |
| 5,743,902 A | 4/1998 | Trost |
| 5,746,735 A | 5/1998 | Furumoto et al. |
| 5,748,822 A | 5/1998 | Miura et al. |
| 5,749,868 A | 5/1998 | Furumoto |
| 5,755,751 A | 5/1998 | Eckhouse |
| 5,759,162 A | 6/1998 | Oppelt et al. |
| 5,759,200 A | 6/1998 | Azar |
| 5,760,362 A | 6/1998 | Etoy |
| 5,769,076 A | 6/1998 | Maekawa et al. |
| 5,776,129 A | 7/1998 | Mersch |
| 5,782,249 A | 7/1998 | Weber et al. |
| 5,802,136 A | 9/1998 | Carol |
| 5,807,386 A | 9/1998 | Slatkine et al. |
| 5,810,801 A | 9/1998 | Anderson et al. |
| 5,810,802 A | 9/1998 | Panescu et al. |
| 5,812,567 A | 9/1998 | Jeon et al. |
| 5,813,855 A | 9/1998 | Crisio, Jr. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |
| 5,818,580 A | 10/1998 | Murnick |
| 5,820,625 A | 10/1998 | Izawa et al. |
| 5,820,626 A | 10/1998 | Baumgardner |
| 5,822,034 A | 10/1998 | Shimashita et al. |
| 5,824,023 A | 10/1998 | Anderson |
| 5,827,264 A | 10/1998 | Hohla |
| 5,828,803 A | 10/1998 | Eckhouse |
| 5,830,208 A | 11/1998 | Muller |
| 5,830,209 A | 11/1998 | Savage et al. |
| 5,835,648 A | 11/1998 | Narciso, Jr. |
| 5,836,877 A | 11/1998 | Zavislan |
| 5,836,999 A | 11/1998 | Eckhouse et al. |
| 5,837,001 A | 11/1998 | Mackey |
| 5,840,048 A | 11/1998 | Cheng |
| 5,843,072 A | 12/1998 | Furumoto et al. |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,868,732 A | 2/1999 | Waldman et al. |
| 5,871,479 A | 2/1999 | Furumoto et al. |
| 5,871,480 A | 2/1999 | Tankovich |
| 5,879,159 A | 3/1999 | Cipolla |
| 5,879,346 A | 3/1999 | Waldman et al. |
| 5,879,376 A | 3/1999 | Miller |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,893,828 A | 4/1999 | Uram |
| 5,893,885 A | 4/1999 | Webster, Jr. |
| 5,895,350 A | 4/1999 | Hori |
| 5,897,549 A | 4/1999 | Tankovich |
| 5,906,609 A | 5/1999 | Assa et al. |
| 5,908,418 A | 6/1999 | Dority et al. |
| 5,908,731 A | 6/1999 | Leenders et al. |
| 5,913,883 A | 6/1999 | Alexander et al. |
| 5,916,211 A | 6/1999 | Quon et al. |
| 5,919,601 A | 7/1999 | Nguyen et al. |
| 5,920,374 A | 7/1999 | Vaphiades et al. |
| 5,921,926 A | 7/1999 | Rolland et al. |
| 5,928,222 A | 7/1999 | Kleinerman |
| 5,935,124 A | 8/1999 | Klumb et al. |
| 5,944,687 A | 8/1999 | Benett et al. |
| 5,944,748 A | 8/1999 | Mager et al. |
| 5,948,011 A | 9/1999 | Knowlton |
| 5,948,596 A | 9/1999 | Zhong et al. |
| 5,949,222 A | 9/1999 | Buono |
| 5,951,543 A | 9/1999 | Brauer |
| 5,954,710 A | 9/1999 | Paolini et al. |
| 5,955,490 A | 9/1999 | Kennedy et al. |
| 5,957,915 A | 9/1999 | Trost |
| 5,964,749 A | 10/1999 | Eckhouse et al. |
| 5,968,033 A | 10/1999 | Fuller et al. |
| 5,968,034 A | 10/1999 | Fullmer et al. |
| 5,971,976 A | 10/1999 | Wang et al. |
| 5,974,059 A | 10/1999 | Dawson |
| 5,974,616 A | 11/1999 | Dreyfus |
| 5,976,123 A | 11/1999 | Baumgardner et al. |
| 5,977,723 A | 11/1999 | Yoon |
| 5,979,454 A | 11/1999 | Anvari et al. |
| 5,983,900 A | 11/1999 | Clement et al. |
| 5,984,915 A | 11/1999 | Loeb et al. |
| 6,004,723 A | 12/1999 | Figov |
| 6,007,219 A | 12/1999 | O'Meara |
| 6,015,404 A | 1/2000 | Altshuler et al. |
| 6,017,677 A | 1/2000 | Maemoto et al. |
| 6,022,316 A | 2/2000 | Eppstein et al. |
| 6,022,346 A | 2/2000 | Panescu et al. |
| 6,024,095 A | 2/2000 | Stanley, III |
| 6,026,828 A | 2/2000 | Altshuler |
| 6,027,493 A | 2/2000 | Donitzky et al. |
| 6,027,495 A | 2/2000 | Miller |
| 6,028,694 A | 2/2000 | Schmidt |
| 6,029,303 A | 2/2000 | Dewan |
| 6,029,304 A | 2/2000 | Hulke et al. |
| 6,030,378 A | 2/2000 | Stewart |
| 6,030,399 A | 2/2000 | Ignotz et al. |
| 6,032,071 A | 2/2000 | Binder |
| RE36,634 E | 3/2000 | Ghaffari |
| 6,033,431 A | 3/2000 | Segal |
| 6,036,684 A | 3/2000 | Tankovich et al. |
| 6,044,514 A | 4/2000 | Kaneda et al. |

(56) References Cited

U.S. PATENT DOCUMENTS

| | | | |
|---|---|---|---|
| 6,045,548 A | 4/2000 | Furumoto et al. |
| 6,050,990 A | 4/2000 | Tankovich et al. |
| D424,197 S | 5/2000 | Sydlowski et al. |
| 6,056,548 A | 5/2000 | Neuberger et al. |
| 6,056,738 A | 5/2000 | Marchitto et al. |
| 6,058,937 A | 5/2000 | Doiron et al. |
| 6,059,820 A | 5/2000 | Baronov |
| 6,063,108 A | 5/2000 | Salansky et al. |
| 6,068,963 A | 5/2000 | Aoshima |
| 6,070,092 A | 5/2000 | Kazama et al. |
| 6,071,239 A | 6/2000 | Cribbs et al. |
| 6,074,382 A | 6/2000 | Asah et al. |
| 6,077,294 A | 6/2000 | Cho et al. |
| 6,080,146 A | 6/2000 | Altshuler et al. |
| 6,080,147 A | 6/2000 | Tobinick |
| 6,083,217 A | 7/2000 | Tankovich |
| 6,086,363 A | 7/2000 | Moran et al. |
| 6,086,558 A | 7/2000 | Bower et al. |
| 6,086,580 A | 7/2000 | Mordon et al. |
| 6,090,524 A | 7/2000 | Deboer et al. |
| 6,132,929 A | 7/2000 | Nakamura |
| 6,094,767 A | 8/2000 | Iimura |
| 6,096,028 A | 8/2000 | Bahmanyar et al. |
| 6,096,029 A | 8/2000 | O'Donnell, Jr. |
| 6,096,209 A | 8/2000 | O'Brien et al. |
| 6,099,521 A | 8/2000 | Shadduck |
| 6,101,207 A | 8/2000 | Ilorinne |
| 6,104,959 A | 8/2000 | Spertell |
| 6,106,293 A | 8/2000 | Wiesel |
| 6,106,294 A | 8/2000 | Daniel |
| 6,110,195 A | 8/2000 | Xie et al. |
| 6,112,123 A | 8/2000 | Kelleher et al. |
| 6,113,559 A | 9/2000 | Klopotek |
| 6,117,129 A | 9/2000 | Mukai |
| 6,120,497 A | 9/2000 | Anderson et al. |
| 6,126,655 A | 10/2000 | Domankevitz et al. |
| 6,129,723 A | 10/2000 | Anderson |
| 6,135,774 A | 10/2000 | Hack et al. |
| 6,142,650 A | 11/2000 | Brown et al. |
| 6,142,939 A | 11/2000 | Eppstein et al. |
| 6,149,644 A | 11/2000 | Xie |
| 6,149,895 A | 11/2000 | Kutsch |
| 6,153,352 A | 11/2000 | Oohashi et al. |
| 6,159,203 A | 12/2000 | Sinofsky et al. |
| 6,159,236 A | 12/2000 | Biel |
| 6,162,055 A | 12/2000 | Montgomery et al. |
| 6,162,211 A | 12/2000 | Tankovich et al. |
| 6,162,212 A | 12/2000 | Kreindel et al. |
| 6,162,215 A | 12/2000 | Feng |
| 6,162,218 A | 12/2000 | Elbrecht et al. |
| 6,164,837 A | 12/2000 | Haake et al. |
| 6,171,300 B1 | 1/2001 | Adams |
| 6,171,301 B1 | 1/2001 | Nelson |
| 6,171,302 B1 | 1/2001 | Talpalriu et al. |
| 6,171,332 B1 | 1/2001 | Whitehurst |
| 6,173,202 B1 | 1/2001 | Eppstein |
| 6,174,325 B1 | 1/2001 | Eckhouse |
| 6,176,854 B1 | 1/2001 | Cone |
| 6,177,230 B1 | 1/2001 | Kawamura |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,187,029 B1 | 2/2001 | Shapiro et al. |
| 6,190,825 B1 | 2/2001 | Denzinger et al. |
| 6,190,831 B1 | 2/2001 | Leon et al. |
| 6,197,020 B1 | 3/2001 | O'Donnell, Jr. |
| 6,200,134 B1 | 3/2001 | Kovac et al. |
| 6,200,309 B1 | 3/2001 | Rice et al. |
| 6,202,242 B1 | 3/2001 | Salmon et al. |
| 6,203,540 B1 | 3/2001 | Weber |
| 6,210,425 B1 | 4/2001 | Chen |
| 6,210,426 B1 | 4/2001 | Cho et al. |
| 6,214,034 B1 | 4/2001 | Azar |
| 6,221,068 B1 | 4/2001 | Fried et al. |
| 6,221,095 B1 | 4/2001 | Van Zuylen et al. |
| 6,228,074 B1 | 5/2001 | Almeida |
| 6,228,075 B1 | 5/2001 | Furumoto |
| 6,229,831 B1 | 5/2001 | Nightingale et al. |
| 6,235,015 B1 | 5/2001 | Mead et al. |
| 6,235,016 B1 | 5/2001 | Stewart |
| 6,236,891 B1 | 5/2001 | Ingle et al. |
| 6,238,839 B1 | 5/2001 | Tomita et al. |
| 6,239,442 B1 | 5/2001 | Iimura |
| 6,240,306 B1 | 5/2001 | Rohrscheib et al. |
| 6,240,925 B1 | 6/2001 | McMillan et al. |
| 6,245,093 B1 | 6/2001 | Li et al. |
| 6,245,486 B1 | 6/2001 | Teng |
| 6,246,710 B1 | 6/2001 | Furumoto |
| 6,248,103 B1 | 6/2001 | Tannenbaum et al. |
| 6,248,503 B1 | 6/2001 | Vermeersch et al. |
| 6,251,127 B1 | 6/2001 | Biel |
| 6,246,740 B1 | 7/2001 | Nguyen et al. |
| 6,254,388 B1 | 7/2001 | Yarborough |
| 6,263,233 B1 | 7/2001 | Zavislan et al. |
| 6,264,649 B1 | 7/2001 | Whitcroft et al. |
| 6,267,779 B1 | 7/2001 | Gerdes |
| 6,267,780 B1 | 7/2001 | Streeter |
| 6,273,883 B1 | 8/2001 | Furumoto |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,282,442 B1 | 8/2001 | Destefano et al. |
| 6,283,956 B1 | 9/2001 | McDaniel |
| 6,287,549 B1 | 9/2001 | Sumian et al. |
| 6,290,496 B1 | 9/2001 | Azar et al. |
| 6,290,712 B1 | 9/2001 | Nordquist et al. |
| 6,290,713 B1 | 9/2001 | Russell |
| 6,294,311 B1 | 9/2001 | Shimazu et al. |
| 6,306,130 B1 | 10/2001 | Anderson et al. |
| 6,306,160 B1 | 10/2001 | Nidetzky |
| 6,233,584 B1 | 11/2001 | Ingle et al. |
| 6,315,772 B1 | 11/2001 | Marchitto et al. |
| 6,317,624 B1 | 11/2001 | Kollias et al. |
| 6,319,274 B1 | 11/2001 | Shadduck |
| 6,322,584 B2 | 11/2001 | Ingle et al. |
| 6,325,769 B1 | 12/2001 | Klopotek |
| 6,327,506 B1 | 12/2001 | Yogo et al. |
| 6,328,733 B1 | 12/2001 | Trost |
| 6,331,111 B1 | 12/2001 | Cao |
| 6,332,891 B1 | 12/2001 | Himes |
| 6,338,855 B1 | 1/2002 | Albacarys et al. |
| 6,340,495 B1 | 1/2002 | Sumian et al. |
| 6,343,400 B1 | 2/2002 | Massholder et al. |
| 6,343,933 B1 | 2/2002 | Montgomery et al. |
| 6,346,365 B1 | 2/2002 | Kawauchi et al. |
| 6,350,261 B1 | 2/2002 | Domankevitz et al. |
| 6,350,276 B1 | 2/2002 | Knowlton |
| 6,352,811 B1 | 3/2002 | Patel et al. |
| 6,354,370 B1 | 3/2002 | Miller et al. |
| 6,355,054 B1 | 3/2002 | Neuberger |
| 6,358,242 B1 | 3/2002 | Cecchetti |
| 6,358,272 B1 | 3/2002 | Wilden |
| 6,358,669 B1 | 3/2002 | Savarair-Hauck et al. |
| 6,364,872 B1 | 4/2002 | Hsia et al. |
| 6,383,176 B1 | 5/2002 | Connors et al. |
| 6,383,177 B1 | 5/2002 | Balle-Petersen |
| 6,387,089 B1 | 5/2002 | Kreindel et al. |
| 6,387,353 B1 | 5/2002 | Jensen et al. |
| 6,391,022 B1 | 5/2002 | Furumoto et al. |
| 6,394,949 B1 | 5/2002 | Crowley et al. |
| 6,395,016 B1 | 5/2002 | Oron et al. |
| 6,398,801 B1 | 6/2002 | Clement et al. |
| 6,400,011 B1 | 6/2002 | Miki |
| 6,402,739 B1 | 6/2002 | Neev |
| 6,405,732 B1 | 6/2002 | Edwards et al. |
| 6,406,474 B1 | 6/2002 | Neuberger et al. |
| 6,409,665 B1 | 6/2002 | Scott et al. |
| 6,409,723 B1 | 6/2002 | Edwards |
| 6,413,267 B1 | 7/2002 | Dumoulin-White |
| 6,416,319 B1 | 7/2002 | Cipolla |
| 6,419,389 B1 | 7/2002 | Fuchs et al. |
| 6,423,462 B1 | 7/2002 | Kunita |
| 6,424,852 B1 | 7/2002 | Zavislan |

(56) References Cited

U.S. PATENT DOCUMENTS

| | | |
|---|---|---|
| 6,425,912 B1 | 7/2002 | Knowlton |
| 6,435,873 B1 | 8/2002 | Burgio |
| 6,436,094 B1 | 8/2002 | Reuter |
| 6,439,888 B1 | 8/2002 | Boutoussov et al. |
| 6,440,155 B1 | 8/2002 | Matsumae et al. |
| 6,440,633 B1 | 8/2002 | Kawauchi |
| 6,443,946 B2 | 9/2002 | Clement et al. |
| 6,443,978 B1 | 9/2002 | Zharov |
| 6,447,503 B1 | 9/2002 | Wynne et al. |
| 6,447,504 B1 | 9/2002 | Ben-Haim et al. |
| 6,451,007 B1 | 9/2002 | Koop et al. |
| 6,454,790 B1 | 9/2002 | Neuberger et al. |
| 6,459,919 B1 | 10/2002 | Lys et al. |
| 6,461,296 B1 | 10/2002 | Desai |
| 6,464,694 B1 | 10/2002 | Massengill |
| 6,468,717 B2 | 10/2002 | Kita et al. |
| 6,470,216 B1 | 10/2002 | Mulholland |
| 6,471,712 B2 | 10/2002 | Burres |
| 6,471,716 B1 | 10/2002 | Pecukonis |
| 6,475,211 B2 | 11/2002 | Chess et al. |
| 6,482,199 B1 | 11/2002 | Neev |
| 6,484,052 B1 | 11/2002 | Visuri et al. |
| 6,485,413 B1 | 11/2002 | Boppart et al. |
| 6,491,685 B2 | 12/2002 | Visuri et al. |
| 6,493,608 B1 | 12/2002 | Niemeyer |
| 6,494,900 B1 | 12/2002 | Salansky et al. |
| 6,497,702 B1 | 12/2002 | Bernaz |
| 6,503,269 B2 | 1/2003 | Nield et al. |
| 6,503,486 B2 | 1/2003 | Xu et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,519,376 B2 | 2/2003 | Biagi et al. |
| 6,525,819 B1 | 2/2003 | Delawter et al. |
| 6,527,716 B1 | 3/2003 | Eppstein |
| 6,527,764 B1 | 3/2003 | Neuberger et al. |
| 6,529,540 B1 | 3/2003 | Demmer et al. |
| 6,530,915 B1 | 3/2003 | Eppstein et al. |
| 6,530,916 B1 | 3/2003 | Shimmick |
| 6,537,270 B1 | 3/2003 | Elbrecht et al. |
| 6,544,257 B2 | 4/2003 | Nagage et al. |
| 6,547,780 B1 | 4/2003 | Sinofsky |
| 6,551,346 B2 | 4/2003 | Crossley |
| 6,554,439 B1 | 4/2003 | Teicher et al. |
| 6,556,596 B1 | 4/2003 | Kim et al. |
| 6,558,372 B1 | 5/2003 | Altshuler |
| 6,561,808 B2 | 5/2003 | Neuberger |
| 6,569,155 B1 | 5/2003 | Connors et al. |
| 6,570,892 B1 | 5/2003 | Lin et al. |
| 6,570,893 B1 | 5/2003 | Libatique et al. |
| 6,572,634 B2 | 6/2003 | Koo |
| 6,572,637 B1 | 6/2003 | Yamazaki et al. |
| 6,595,934 B1 | 7/2003 | Hissong et al. |
| 6,600,951 B1 | 7/2003 | Anderson |
| 6,602,245 B1 | 8/2003 | Thiberg |
| 6,602,275 B1 | 8/2003 | Sullivan |
| 6,603,988 B2 | 8/2003 | Dowlatshahi |
| 6,605,080 B1 | 8/2003 | Altshuler et al. |
| 6,605,083 B2 | 8/2003 | Clement et al. |
| 6,606,755 B1 | 8/2003 | Robinson et al. |
| 6,607,525 B2 | 8/2003 | France et al. |
| 6,610,052 B2 | 8/2003 | Furumoto |
| 6,613,040 B2 | 9/2003 | Tankovich et al. |
| 6,616,447 B1 | 9/2003 | Rizoiu et al. |
| 6,616,451 B1 | 9/2003 | Rizoiu et al. |
| 6,618,531 B1 | 9/2003 | Goto et al. |
| 6,623,272 B2 | 9/2003 | Clemans |
| 6,623,513 B2 | 9/2003 | Biel |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,578 B2 | 11/2003 | Mukai |
| 6,641,600 B1 | 11/2003 | Kohler |
| 6,648,904 B2 | 11/2003 | Altshuler et al. |
| 6,652,459 B2 | 11/2003 | Payne et al. |
| 6,653,618 B2 | 11/2003 | Zenzie |
| 6,659,999 B1 | 12/2003 | Anderson et al. |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,666,856 B2 | 12/2003 | Connors et al. |
| 6,669,685 B1 | 12/2003 | Rizoiu et al. |
| 6,675,425 B1 | 1/2004 | Iimura |
| 6,676,654 B1 | 1/2004 | Balle-Petersen |
| 6,679,837 B2 | 1/2004 | Daikuzono |
| 6,682,523 B2 | 1/2004 | Shadduck |
| 6,682,524 B1 | 1/2004 | Elbrecht et al. |
| 6,685,639 B1 | 2/2004 | Wang et al. |
| 6,685,699 B1 | 2/2004 | Eppstein et al. |
| 6,685,722 B1 | 2/2004 | Rosenbluth et al. |
| 6,689,124 B1 | 2/2004 | Thiberg |
| 6,692,456 B1 | 2/2004 | Eppstein et al. |
| 6,692,517 B2 | 2/2004 | Cho et al. |
| 6,699,040 B1 | 3/2004 | Hahn et al. |
| 6,706,035 B2 | 3/2004 | Cense et al. |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,724,958 B1 | 4/2004 | German et al. |
| 6,726,681 B2 | 4/2004 | Grasso et al. |
| 6,736,807 B2 | 5/2004 | Yamazaki et al. |
| 6,743,222 B2 | 6/2004 | Durkin et al. |
| 6,746,444 B2 | 6/2004 | Key |
| 6,749,623 B1 | 6/2004 | His et al. |
| 6,755,647 B2 | 6/2004 | Melikechi et al. |
| 6,770,069 B1 | 8/2004 | Hobart et al. |
| 6,772,053 B2 | 8/2004 | Niemeyer |
| 6,790,205 B1 | 9/2004 | Yamazaki et al. |
| 6,800,122 B2 | 10/2004 | Anderson et al. |
| 6,801,595 B2 | 10/2004 | Grodzins et al. |
| 6,808,331 B2 | 10/2004 | Hall et al. |
| 6,808,532 B2 | 10/2004 | Andersen et al. |
| 6,824,542 B2 | 11/2004 | Jay |
| RE38,670 E | 12/2004 | Asah et al. |
| 6,858,009 B2 | 2/2005 | Kawata et al. |
| 6,860,879 B2 | 3/2005 | Irion et al. |
| 6,860,896 B2 | 3/2005 | Leber et al. |
| 6,862,771 B1 | 3/2005 | Muller |
| 6,863,781 B2 | 3/2005 | Nocera et al. |
| 6,872,203 B2 | 3/2005 | Shafirstein et al. |
| 6,878,144 B2 | 4/2005 | Altshuler et al. |
| 6,881,212 B1 | 4/2005 | Clement et al. |
| 6,887,260 B1 | 5/2005 | McDaniel |
| 6,888,319 B2 | 5/2005 | Inochkin et al. |
| 6,893,259 B1 | 5/2005 | Reizenson |
| 6,902,397 B2 | 6/2005 | Farrell et al. |
| 6,902,563 B2 | 6/2005 | Wilkens et al. |
| 6,905,492 B2 | 6/2005 | Zvuloni et al. |
| 6,916,316 B2 | 7/2005 | Jay |
| 6,917,715 B2 | 7/2005 | Berstis |
| 6,936,046 B2 | 8/2005 | Hissong et al. |
| 6,942,658 B1 | 9/2005 | Rizoiu et al. |
| 6,953,341 B2 | 10/2005 | Black |
| 6,974,450 B2 | 12/2005 | Weber et al. |
| 6,974,451 B2 | 12/2005 | Altshuler et al. |
| 6,976,985 B2 | 12/2005 | Altshuler et al. |
| 6,986,903 B2 | 1/2006 | Zulli et al. |
| 6,989,007 B2 | 1/2006 | Shadduck |
| 6,989,023 B2 | 1/2006 | Black |
| 6,991,644 B2 | 1/2006 | Spooner et al. |
| 6,997,923 B2 | 2/2006 | Anderson et al. |
| 7,001,413 B2 | 2/2006 | Butler |
| 7,006,223 B2 | 2/2006 | Mullani |
| 7,006,874 B2 | 2/2006 | Knowlton |
| 7,018,396 B2 | 3/2006 | Sierra et al. |
| 7,029,469 B2 | 4/2006 | Vasily |
| 7,033,349 B2 | 4/2006 | Key |
| 7,041,094 B2 | 5/2006 | Connors et al. |
| 7,041,100 B2 | 5/2006 | Kreindel |
| 7,044,959 B2 | 5/2006 | Anderson et al. |

(56) References Cited

U.S. PATENT DOCUMENTS

| | | |
|---|---|---|
| 7,060,061 B2 | 6/2006 | Altshuler et al. |
| 7,066,733 B2 | 6/2006 | Logan et al. |
| 7,070,611 B2 | 7/2006 | Biel |
| 7,077,840 B2 | 7/2006 | Altshuler et al. |
| 7,081,128 B2 | 7/2006 | Hart et al. |
| 7,097,639 B1 | 8/2006 | Almeida |
| 7,097,656 B1 | 8/2006 | Akopov et al. |
| 7,104,985 B2 | 9/2006 | Martinelli |
| 7,118,562 B2 | 10/2006 | Furumoto |
| 7,118,563 B2 | 10/2006 | Weckwerth et al. |
| 7,135,033 B2 | 11/2006 | Altshuler et al. |
| 7,144,247 B2 | 12/2006 | Black |
| 7,144,248 B2 | 12/2006 | Irwin |
| 7,145,105 B2 | 12/2006 | Gaulard |
| 7,145,108 B2 | 12/2006 | Kanel et al. |
| 7,160,289 B2 | 1/2007 | Cohen |
| 7,170,034 B2 | 1/2007 | Shalev |
| 7,175,617 B2 | 2/2007 | Jay |
| 7,182,760 B2 | 2/2007 | Kubota |
| 7,198,634 B2 | 4/2007 | Harth et al. |
| 7,202,446 B2 | 4/2007 | Shalev |
| 7,204,832 B2 | 4/2007 | Altshuler et al. |
| 7,216,055 B1 | 5/2007 | Horton et al. |
| 7,217,265 B2 | 5/2007 | Hennings et al. |
| 7,217,267 B2 | 5/2007 | Jay |
| 7,220,254 B2 | 5/2007 | Altshuler et al. |
| 7,223,270 B2 | 5/2007 | Altshuler et al. |
| 7,223,281 B2 | 5/2007 | Altshuler et al. |
| 7,255,691 B2 | 8/2007 | Tolkoff et al. |
| 7,274,155 B2 | 9/2007 | Inochkin et al. |
| 7,276,058 B2 | 10/2007 | Altshuler et al. |
| 7,280,866 B1 | 10/2007 | McIntosh et al. |
| 7,282,060 B2 | 10/2007 | DeBenedictis |
| 7,282,723 B2 | 10/2007 | Schomaket et al. |
| 7,291,140 B2 | 11/2007 | MacFarland et al. |
| 7,291,141 B2 | 11/2007 | Harvey |
| 7,309,335 B2 | 12/2007 | Altshuler et al. |
| 7,311,722 B2 | 12/2007 | Larsen |
| 7,322,972 B2 | 1/2008 | Viator et al. |
| 7,329,273 B2 | 2/2008 | Altshuler et al. |
| 7,329,274 B2 | 2/2008 | Altshuler et al. |
| 7,331,953 B2 | 2/2008 | Manstein et al. |
| 7,331,964 B2 | 2/2008 | Maricle et al. |
| 7,333,698 B2 | 2/2008 | Israel |
| 7,333,841 B2 | 2/2008 | Maruo et al. |
| 7,351,252 B2 | 4/2008 | Altshuler et al. |
| 7,354,448 B2 | 4/2008 | Altshuler et al. |
| 7,422,598 B2 | 9/2008 | Altshuler et al. |
| 7,423,767 B2 | 9/2008 | Steinsiek et al. |
| 7,431,719 B2 | 10/2008 | Altshuler |
| 7,436,863 B2 | 10/2008 | Matsuda et al. |
| 7,500,956 B1 | 3/2009 | Wilk |
| 7,531,967 B2 | 5/2009 | Inochkin et al. |
| 7,540,869 B2 | 6/2009 | Altshuler et al. |
| 7,553,308 B2 | 6/2009 | Jay |
| 7,586,957 B2 | 9/2009 | Sierra et al. |
| 7,588,547 B2 | 9/2009 | Deem et al. |
| 7,624,640 B2 | 12/2009 | Maris et al. |
| 7,647,092 B2 | 1/2010 | Motz et al. |
| 7,699,058 B1 | 4/2010 | Jay |
| 7,722,600 B2 | 5/2010 | Connors et al. |
| 7,758,621 B2 | 7/2010 | Altshuler et al. |
| 7,763,016 B2 | 7/2010 | Altshuler et al. |
| 7,839,972 B2 | 11/2010 | Ruchala et al. |
| 7,856,985 B2 | 12/2010 | Mirkov et al. |
| 7,860,554 B2 | 12/2010 | Leonardi |
| 7,929,579 B2 | 4/2011 | Hohm et al. |
| 7,931,028 B2 | 4/2011 | Jay |
| 7,935,107 B2 | 5/2011 | Altshuler et al. |
| 7,938,821 B2 | 5/2011 | Chan et al. |
| 7,942,869 B2 | 5/2011 | Houbolt et al. |
| 7,942,915 B2 | 5/2011 | Altshuler et al. |
| 7,942,916 B2 | 5/2011 | Altshuler et al. |
| 7,998,181 B2 | 8/2011 | Nightingale et al. |
| 8,002,768 B1 | 8/2011 | Altshuler et al. |
| 8,027,710 B1 | 9/2011 | Dannan |
| 8,109,924 B2 | 2/2012 | Altshuler |
| 8,113,209 B2 | 2/2012 | Masotti et al. |
| 8,182,473 B2 | 5/2012 | Altshuler et al. |
| 8,317,779 B2 | 11/2012 | Mirkov et al. |
| 8,322,348 B2 | 12/2012 | Mirkov et al. |
| 8,328,794 B2 | 12/2012 | Altshuler et al. |
| 8,328,796 B2 | 12/2012 | Altshuler et al. |
| 8,346,347 B2 | 1/2013 | Altshuler et al. |
| 8,357,145 B2 | 1/2013 | Hennings et al. |
| 8,378,322 B2 | 2/2013 | Dahm et al. |
| 8,439,940 B2 | 5/2013 | Chomas et al. |
| 9,780,518 B2 | 10/2017 | Sierra et al. |
| 10,245,107 B2 | 4/2019 | Sierra et al. |
| 10,285,757 B2 | 5/2019 | Robertson et al. |
| 2001/0007068 A1 | 7/2001 | Ota |
| 2001/0008973 A1 | 7/2001 | Van Zuylen et al. |
| 2001/0016732 A1 | 8/2001 | Hobart et al. |
| 2001/0023363 A1 | 9/2001 | Harth et al. |
| 2001/0024777 A1 | 9/2001 | Azar et al. |
| 2001/0025173 A1 | 9/2001 | Ritchie et al. |
| 2001/0029956 A1 | 10/2001 | Argenta et al. |
| 2001/0041886 A1 | 11/2001 | Durkin et al. |
| 2001/0046244 A1 | 11/2001 | Klimov et al. |
| 2001/0046652 A1 | 11/2001 | Ostler et al. |
| 2001/0048077 A1 | 12/2001 | Afanassieva |
| 2002/0002367 A1 | 1/2002 | Tankovich et al. |
| 2002/0004066 A1 | 1/2002 | Stanley et al. |
| 2002/0005475 A1 | 1/2002 | Zenzie |
| 2002/0013572 A1 | 1/2002 | Berlin |
| 2002/0015911 A1 | 2/2002 | Nakamura |
| 2002/0016587 A1 | 2/2002 | Furumoto |
| 2002/0018754 A1 | 2/2002 | Sagel et al. |
| 2002/0019624 A1 | 2/2002 | Clement et al. |
| 2002/0019625 A1 | 2/2002 | Azar |
| 2002/0026225 A1 | 2/2002 | Segal |
| 2002/0028404 A1 | 3/2002 | Nakamura |
| 2002/0029071 A1 | 3/2002 | Whitehurst |
| 2002/0032437 A1 | 3/2002 | Andrews et al. |
| 2002/0039702 A1 | 4/2002 | Hotta |
| 2002/0045891 A1 | 4/2002 | Clement et al. |
| 2002/0048722 A1 | 4/2002 | Aoshima |
| 2002/0049432 A1 | 4/2002 | Mukai |
| 2002/0049483 A1 | 4/2002 | Knowlton |
| 2002/0058890 A1 | 5/2002 | Visuri et al. |
| 2002/0071287 A1 | 6/2002 | Haase |
| 2002/0071827 A1 | 6/2002 | Petersen et al. |
| 2002/0072676 A1 | 6/2002 | Afanassieva |
| 2002/0081555 A1 | 6/2002 | Wiesel |
| 2002/0090725 A1 | 7/2002 | Simpson et al. |
| 2002/0091377 A1 | 7/2002 | Anderson et al. |
| 2002/0108193 A1 | 8/2002 | Gruber |
| 2002/0111546 A1 | 8/2002 | Cook et al. |
| 2002/0111610 A1 | 8/2002 | Nordquist |
| 2002/0120256 A1 | 8/2002 | Furuno et al. |
| 2002/0123745 A1 | 9/2002 | Svaasand et al. |
| 2002/0125230 A1 | 9/2002 | Haight et al. |
| 2002/0127224 A1 | 9/2002 | Chen |
| 2002/0128635 A1 | 9/2002 | Altshuler et al. |
| 2002/0128695 A1 | 9/2002 | Harth et al. |
| 2002/0128696 A1 | 9/2002 | Pearl |
| 2002/0151878 A1 | 10/2002 | Shimmick et al. |
| 2002/0151879 A1 | 10/2002 | Loeb |
| 2002/0160299 A1 | 10/2002 | Asawa et al. |
| 2002/0161357 A1 | 10/2002 | Anderson et al. |
| 2002/0161418 A1 | 10/2002 | Wilkens et al. |
| 2002/0167974 A1 | 11/2002 | Kennedy et al. |
| 2002/0173723 A1 | 11/2002 | Lewis |
| 2002/0173777 A1 | 11/2002 | Sand |
| 2002/0173780 A1 | 11/2002 | Altshuler et al. |
| 2002/0173781 A1 | 11/2002 | Cense et al. |
| 2002/0173782 A1 | 11/2002 | Cense et al. |
| 2002/0182563 A1 | 12/2002 | Boutoussov et al. |
| 2002/0183808 A1 | 12/2002 | Biel |
| 2002/0186380 A1* | 12/2002 | Drake, Jr. ............... G01H 9/00 356/502 |
| 2002/0198517 A1 | 12/2002 | Alfano et al. |
| 2003/0004499 A1 | 1/2003 | McDaniel |
| 2003/0009158 A1 | 1/2003 | Perricone |

(56) References Cited

U.S. PATENT DOCUMENTS

| | | |
|---|---|---|
| 2003/0009205 A1 | 1/2003 | Biel |
| 2003/0018373 A1 | 1/2003 | Eckhardt et al. |
| 2003/0023235 A1 | 1/2003 | Cense et al. |
| 2003/0023283 A1 | 1/2003 | McDaniel |
| 2003/0023284 A1 | 1/2003 | Gartstein et al. |
| 2003/0028186 A1 | 2/2003 | Kreintel |
| 2003/0028227 A1 | 2/2003 | Neuberger et al. |
| 2003/0032900 A1 | 2/2003 | Ella |
| 2003/0032950 A1 | 2/2003 | Altshuler et al. |
| 2003/0036680 A1 | 2/2003 | Black |
| 2003/0040739 A1 | 2/2003 | Koop |
| 2003/0055413 A1 | 3/2003 | Altshuler et al. |
| 2003/0055414 A1 | 3/2003 | Altshuler et al. |
| 2003/0057875 A1 | 3/2003 | Inochkin et al. |
| 2003/0059738 A1 | 3/2003 | Neuberger |
| 2003/0065314 A1 | 4/2003 | Altshuler et al. |
| 2003/0073989 A1 | 4/2003 | Hoey et al. |
| 2003/0083649 A1 | 5/2003 | Margaron et al. |
| 2003/0084534 A1 | 5/2003 | Kaizuka |
| 2003/0092982 A1 | 5/2003 | Eppstein |
| 2003/0097122 A1 | 5/2003 | Ganz et al. |
| 2003/0100936 A1 | 5/2003 | Altshuler et al. |
| 2003/0104340 A1 | 6/2003 | Clemans |
| 2003/0109787 A1 | 6/2003 | Black |
| 2003/0109860 A1 | 6/2003 | Black |
| 2003/0113684 A1 | 6/2003 | Scott |
| 2003/0129154 A1 | 7/2003 | McDaniel |
| 2003/0130709 A1 | 7/2003 | Haber |
| 2003/0152528 A1 | 8/2003 | Singh et al. |
| 2003/0158550 A1 | 8/2003 | Ganz et al. |
| 2003/0163884 A1 | 9/2003 | Weihrauch |
| 2003/0167080 A1 | 9/2003 | Hart et al. |
| 2003/0169433 A1 | 9/2003 | Koele et al. |
| 2003/0181896 A1 | 9/2003 | Zvuloni et al. |
| 2003/0187319 A1 | 10/2003 | Kaneko |
| 2003/0187383 A1 | 10/2003 | Weber et al. |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0216719 A1 | 11/2003 | DeBenedictis |
| 2003/0216795 A1 | 11/2003 | Harth et al. |
| 2003/0232303 A1 | 12/2003 | Black |
| 2003/0233138 A1 | 12/2003 | Spooner |
| 2004/0006332 A1 | 1/2004 | Black |
| 2004/0010298 A1 | 1/2004 | Altshuler et al. |
| 2004/0015156 A1 | 1/2004 | Vasily |
| 2004/0015158 A1 | 1/2004 | Chen et al. |
| 2004/0019120 A1 | 1/2004 | Vargas et al. |
| 2004/0019990 A1 | 2/2004 | Farrell et al. |
| 2004/0024388 A1 | 2/2004 | Altshuler |
| 2004/0024430 A1 | 2/2004 | Bader et al. |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0036975 A1 | 2/2004 | Slatkine |
| 2004/0054248 A1 | 3/2004 | Kimchy et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0092506 A1 | 5/2004 | Thompson et al. |
| 2004/0093042 A1 | 5/2004 | Altshuler et al. |
| 2004/0093043 A1 | 5/2004 | Edel et al. |
| 2004/0098070 A1 | 5/2004 | Mohr et al. |
| 2004/0105611 A1 | 6/2004 | Bischel et al. |
| 2004/0111031 A1 | 6/2004 | Alfano et al. |
| 2004/0111086 A1 | 6/2004 | Trombly |
| 2004/0111132 A1 | 6/2004 | Shenderova et al. |
| 2004/0116984 A1 | 6/2004 | Spooner et al. |
| 2004/0122311 A1 | 6/2004 | Cosman |
| 2004/0133251 A1 | 7/2004 | Altshuler et al. |
| 2004/0143181 A1 | 7/2004 | Damasio et al. |
| 2004/0143247 A1 | 7/2004 | Anderson et al. |
| 2004/0143920 A1 | 7/2004 | Nanda |
| 2004/0147984 A1 | 7/2004 | Altshuler et al. |
| 2004/0156626 A1 | 8/2004 | Thoms |
| 2004/0161213 A1 | 8/2004 | Lee |
| 2004/0162490 A1 | 8/2004 | Soltz et al. |
| 2004/0162549 A1 | 8/2004 | Altshuler |
| 2004/0162596 A1 | 8/2004 | Altshuler et al. |
| 2004/0167502 A1 | 8/2004 | Weckwerth et al. |
| 2004/0176754 A1 | 9/2004 | Island et al. |
| 2004/0176764 A1 | 9/2004 | Dant |
| 2004/0186465 A1 | 9/2004 | Francischelli |
| 2004/0191729 A1 | 9/2004 | Altshuler et al. |
| 2004/0193234 A1 | 9/2004 | Butler |
| 2004/0193235 A1 | 9/2004 | Altshuler et al. |
| 2004/0193236 A1 | 9/2004 | Altshuler et al. |
| 2004/0199079 A1 | 10/2004 | Chuck et al. |
| 2004/0199151 A1 | 10/2004 | Neuberger |
| 2004/0199227 A1 | 10/2004 | Altshuler et al. |
| 2004/0204745 A1 | 10/2004 | Altshuler et al. |
| 2004/0208918 A1 | 10/2004 | Koch et al. |
| 2004/0210275 A1 | 10/2004 | Town et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2004/0230260 A1 | 11/2004 | MacFarland et al. |
| 2004/0234460 A1 | 11/2004 | Tarver et al. |
| 2004/0249261 A1 | 12/2004 | Torchia et al. |
| 2004/0260210 A1 | 12/2004 | Ella et al. |
| 2005/0015077 A1 | 1/2005 | Kuklin et al. |
| 2005/0038418 A1 | 2/2005 | Altshuler et al. |
| 2005/0049467 A1 | 3/2005 | Stamatas et al. |
| 2005/0049582 A1 | 3/2005 | DeBenedictis |
| 2005/0049658 A1 | 3/2005 | Connors et al. |
| 2005/0063931 A1 | 3/2005 | Paus et al. |
| 2005/0065502 A1 | 3/2005 | Stoltz |
| 2005/0065531 A1 | 3/2005 | Cohen |
| 2005/0074038 A1 | 4/2005 | Khaydarov |
| 2005/0080404 A1 | 4/2005 | Jones et al. |
| 2005/0085875 A1 | 4/2005 | Van Zuylen |
| 2005/0102213 A1 | 5/2005 | Savasoglu et al. |
| 2005/0107849 A1 | 5/2005 | Altshuler et al. |
| 2005/0113815 A1 | 5/2005 | Ritchie et al. |
| 2005/0113890 A1 | 5/2005 | Ritchie et al. |
| 2005/0116673 A1 | 6/2005 | Carl et al. |
| 2005/0131400 A1 | 6/2005 | Hennings et al. |
| 2005/0143719 A1 | 6/2005 | Sink |
| 2005/0143723 A1 | 6/2005 | Zvuloni et al. |
| 2005/0154380 A1 | 7/2005 | DeBenedictis |
| 2005/0165315 A1 | 7/2005 | Zuluga et al. |
| 2005/0165393 A1 | 7/2005 | Eppstein |
| 2005/0168158 A1 | 8/2005 | Inochkin et al. |
| 2005/0170313 A1 | 8/2005 | Pitz et al. |
| 2005/0171517 A1 | 8/2005 | Altshuler et al. |
| 2005/0171581 A1 | 8/2005 | Connors et al. |
| 2005/0177026 A1 | 8/2005 | Hoeg et al. |
| 2005/0177139 A1 | 8/2005 | Yamazaki et al. |
| 2005/0177142 A1 | 8/2005 | Jay |
| 2005/0182389 A1 | 8/2005 | Laporte et al. |
| 2005/0197681 A1 | 9/2005 | Barolet et al. |
| 2005/0203496 A1 | 9/2005 | Ritchie et al. |
| 2005/0203497 A1 | 9/2005 | Speeg et al. |
| 2005/0213708 A1 | 9/2005 | Lawrence et al. |
| 2005/0215988 A1 | 9/2005 | Altshuler et al. |
| 2005/0220726 A1 | 10/2005 | Pauly et al. |
| 2005/0222556 A1 | 10/2005 | Arivra et al. |
| 2005/0245917 A1 | 11/2005 | Strassl et al. |
| 2005/0251116 A1 | 11/2005 | Steinke et al. |
| 2005/0251117 A1 | 11/2005 | Anderson et al. |
| 2005/0251118 A1 | 11/2005 | Anderson et al. |
| 2005/0251120 A1 | 11/2005 | Anderson et al. |
| 2005/0257612 A1 | 11/2005 | Hiemer et al. |
| 2005/0281530 A1 | 12/2005 | Rizoiu et al. |
| 2006/0004306 A1 | 1/2006 | Altshuler et al. |
| 2006/0004347 A1 | 1/2006 | Altshuler et al. |
| 2006/0007965 A1 | 1/2006 | Tankovich et al. |
| 2006/0009750 A1 | 1/2006 | Altshuler et al. |
| 2006/0013533 A1 | 1/2006 | Slatkine et al. |
| 2006/0020309 A1 | 1/2006 | Altshuler et al. |
| 2006/0023757 A1 | 2/2006 | Mooradian et al. |
| 2006/0047281 A1 | 3/2006 | Kreindel et al. |
| 2006/0052661 A1 | 3/2006 | Gannot et al. |

(56) References Cited

U.S. PATENT DOCUMENTS

| | | |
|---|---|---|
| 2006/0056589 A1 | 3/2006 | Engelward |
| 2006/0058712 A1 | 3/2006 | Altshuler et al. |
| 2006/0062448 A1 | 3/2006 | Hirsch et al. |
| 2006/0072635 A1 | 4/2006 | Wang |
| 2006/0079947 A1 | 4/2006 | Tankovich et al. |
| 2006/0089687 A1 | 4/2006 | Spooner et al. |
| 2006/0094988 A1 | 5/2006 | Tosaya et al. |
| 2006/0100677 A1 | 5/2006 | Blumenkranz et al. |
| 2006/0116671 A1 | 6/2006 | Slayton et al. |
| 2006/0118127 A1 | 6/2006 | Chinn |
| 2006/0122584 A1 | 6/2006 | Bommannan et al. |
| 2006/0122668 A1 | 6/2006 | Anderson et al. |
| 2006/0128771 A1 | 6/2006 | Mirkov et al. |
| 2006/0149343 A1 | 7/2006 | Altshulter et al. |
| 2006/0153254 A1* | 7/2006 | Franjic ............... G02F 1/39 372/30 |
| 2006/0155266 A1 | 7/2006 | Manstein et al. |
| 2006/0161143 A1 | 7/2006 | Altshuler et al. |
| 2006/0173480 A1 | 8/2006 | Zhang |
| 2006/0194164 A1 | 8/2006 | Altshuler et al. |
| 2006/0206103 A1 | 9/2006 | Altshuler et al. |
| 2006/0217689 A1 | 9/2006 | Dick et al. |
| 2006/0224148 A1 | 10/2006 | Cho et al. |
| 2006/0247609 A1 | 11/2006 | Mirkov et al. |
| 2006/0253176 A1 | 11/2006 | Caruso et al. |
| 2006/0259102 A1 | 11/2006 | Slatkine |
| 2006/0265032 A1 | 11/2006 | Hennings |
| 2006/0271028 A1 | 11/2006 | Altshuler et al. |
| 2006/0280221 A1* | 12/2006 | Seitel ............... H01S 3/08 372/100 |
| 2006/0282067 A1 | 12/2006 | Koop et al. |
| 2006/0287646 A1 | 12/2006 | Altshuler et al. |
| 2006/0293727 A1 | 12/2006 | Spooner et al. |
| 2006/0293728 A1 | 12/2006 | Roersma et al. |
| 2007/0027440 A1 | 2/2007 | Altshuler et al. |
| 2007/0038271 A1 | 2/2007 | Cole et al. |
| 2007/0038206 A1 | 3/2007 | Altshuler et al. |
| 2007/0049910 A1 | 3/2007 | Altshuler et al. |
| 2007/0060819 A1 | 3/2007 | Altshuler et al. |
| 2007/0060989 A1 | 3/2007 | Deem et al. |
| 2007/0067006 A1 | 3/2007 | Altshuler et al. |
| 2007/0073308 A1 | 3/2007 | Anderson et al. |
| 2007/0078501 A1 | 4/2007 | Altshuler et al. |
| 2007/0088206 A1 | 4/2007 | Peyman |
| 2007/0093797 A1 | 4/2007 | Chan et al. |
| 2007/0105212 A1 | 5/2007 | Oldham et al. |
| 2007/0121069 A1 | 5/2007 | Andersen et al. |
| 2007/0123851 A1 | 5/2007 | Alejandro et al. |
| 2007/0142881 A1 | 6/2007 | Hennings |
| 2007/0159592 A1 | 7/2007 | Rylander et al. |
| 2007/0173749 A1 | 7/2007 | Williams et al. |
| 2007/0179378 A1 | 8/2007 | Boese et al. |
| 2007/0179470 A1 | 8/2007 | Toombs |
| 2007/0185552 A1 | 8/2007 | Masotti et al. |
| 2007/0191827 A1 | 8/2007 | Lischinsky et al. |
| 2007/0194717 A1 | 8/2007 | Belikov et al. |
| 2007/0197883 A1 | 8/2007 | Zhou et al. |
| 2007/0198004 A1 | 8/2007 | Altshuler et al. |
| 2007/0208252 A1 | 9/2007 | Makower |
| 2007/0213696 A1 | 9/2007 | Altshuler et al. |
| 2007/0213698 A1 | 9/2007 | Altshuler et al. |
| 2007/0213792 A1 | 9/2007 | Yaroslavsky et al. |
| 2007/0213851 A1 | 9/2007 | Bellas et al. |
| 2007/0219602 A1 | 9/2007 | Ostrovsky et al. |
| 2007/0219604 A1 | 9/2007 | Yaroslavsky et al. |
| 2007/0219605 A1 | 9/2007 | Yaroslavsky et al. |
| 2007/0239142 A1 | 10/2007 | Altshuler et al. |
| 2007/0239143 A1 | 10/2007 | Altshuler et al. |
| 2007/0244527 A1 | 10/2007 | Hatayama et al. |
| 2007/0255355 A1 | 11/2007 | Altshuler et al. |
| 2007/0260230 A1 | 11/2007 | Youngquist et al. |
| 2007/0264625 A1 | 11/2007 | DeBenedictis |
| 2007/0288071 A1 | 12/2007 | Rogers et al. |
| 2008/0003536 A1 | 1/2008 | Altshuler et al. |
| 2008/0004608 A1 | 1/2008 | Dacquay et al. |
| 2008/0004611 A1 | 1/2008 | Houbolt et al. |
| 2008/0009842 A1 | 1/2008 | Manstein et al. |
| 2008/0033516 A1 | 2/2008 | Altshuler et al. |
| 2008/0058782 A1 | 3/2008 | Frangcischelli |
| 2008/0058783 A1 | 3/2008 | Altshuler et al. |
| 2008/0082089 A1* | 4/2008 | Jones ............... A61N 5/0616 606/9 |
| 2008/0103565 A1 | 5/2008 | Altshuler et al. |
| 2008/0132886 A1 | 6/2008 | Cohen et al. |
| 2008/0139901 A1 | 6/2008 | Altshuler et al. |
| 2008/0140164 A1 | 6/2008 | Oberreiter et al. |
| 2008/0147054 A1 | 6/2008 | Altshuler et al. |
| 2008/0154157 A1 | 6/2008 | Altshuler et al. |
| 2008/0154247 A1 | 6/2008 | Dallarosa |
| 2008/0172047 A1 | 7/2008 | Altshuler et al. |
| 2008/0183162 A1 | 7/2008 | Altshuler et al. |
| 2008/0183250 A1 | 7/2008 | Tanojo et al. |
| 2008/0186591 A1 | 8/2008 | Altshuler et al. |
| 2008/0194969 A1 | 8/2008 | Werahera et al. |
| 2008/0195183 A1 | 8/2008 | Botchkareva et al. |
| 2008/0208105 A1 | 8/2008 | Zelickson et al. |
| 2008/0214988 A1 | 9/2008 | Altshuler et al. |
| 2008/0215038 A1 | 9/2008 | Bakker |
| 2008/0248554 A1 | 10/2008 | Merchant et al. |
| 2008/0262577 A1 | 10/2008 | Altshuler et al. |
| 2008/0273559 A1 | 11/2008 | Grishin et al. |
| 2008/0294150 A1 | 11/2008 | Altshuler et al. |
| 2008/0294152 A1 | 11/2008 | Altshuler et al. |
| 2008/0294153 A1 | 11/2008 | Altshuler et al. |
| 2008/0306471 A1 | 12/2008 | Altshuler et al. |
| 2008/0319430 A1 | 12/2008 | Zenzie et al. |
| 2009/0018531 A1 | 1/2009 | Welches |
| 2009/0018624 A1 | 1/2009 | Levinson et al. |
| 2009/0024023 A1 | 1/2009 | Welches et al. |
| 2009/0024192 A1 | 1/2009 | Knowlton |
| 2009/0024193 A1 | 1/2009 | Altshuler et al. |
| 2009/0043294 A1 | 2/2009 | Island et al. |
| 2009/0048557 A1 | 2/2009 | Yeshurun et al. |
| 2009/0054956 A1 | 2/2009 | Sierra et al. |
| 2009/0069741 A1 | 3/2009 | Altshuler et al. |
| 2009/0076488 A1 | 3/2009 | Welches et al. |
| 2009/0076489 A1 | 3/2009 | Welches et al. |
| 2009/0132011 A1 | 5/2009 | Altshuler et al. |
| 2009/0137995 A1 | 5/2009 | Altshuler et al. |
| 2009/0149843 A1 | 6/2009 | Smits et al. |
| 2009/0149844 A1 | 6/2009 | Altshuler et al. |
| 2009/0222068 A1 | 9/2009 | Oberreiter et al. |
| 2009/0227995 A1 | 9/2009 | Bhawalkar et al. |
| 2009/0248004 A1 | 10/2009 | Altshuler et al. |
| 2009/0254076 A1 | 10/2009 | Altshuler et al. |
| 2009/0287195 A1 | 11/2009 | Altshuler et al. |
| 2009/0292277 A1 | 11/2009 | Sierra et al. |
| 2009/0312749 A1 | 12/2009 | Pini et al. |
| 2010/0010507 A1 | 1/2010 | Kinoshita |
| 2010/0015576 A1 | 1/2010 | Altshuler et al. |
| 2010/0021867 A1 | 1/2010 | Altshuler et al. |
| 2010/0036295 A1 | 2/2010 | Altshuler et al. |
| 2010/0049180 A1 | 2/2010 | Wells et al. |
| 2010/0054284 A1 | 3/2010 | Dekker et al. |
| 2010/0109041 A1 | 5/2010 | Yin et al. |
| 2010/0123399 A1 | 5/2010 | Bollmann et al. |
| 2010/0145321 A1 | 6/2010 | Altshuler et al. |
| 2010/0195680 A1 | 8/2010 | Sierra et al. |
| 2010/0198134 A1 | 8/2010 | Eckhouse et al. |
| 2010/0204686 A1 | 8/2010 | Yaroslavsky et al. |
| 2010/0217248 A1 | 8/2010 | Mirkov et al. |
| 2010/0278756 A1 | 11/2010 | Chung et al. |
| 2010/0286673 A1 | 11/2010 | Altshuler et al. |
| 2010/0296531 A1 | 11/2010 | Hohm et al. |
| 2010/0298744 A1 | 11/2010 | Altshuler et al. |
| 2011/0046523 A1 | 2/2011 | Altshuler et al. |
| 2011/0087155 A1 | 4/2011 | Uhland et al. |
| 2011/0118722 A1 | 5/2011 | Lischinsky et al. |
| 2011/0137230 A1 | 6/2011 | Altshuler et al. |
| 2011/0152847 A1 | 6/2011 | Mirkov et al. |
| 2011/0172651 A1 | 7/2011 | Altshuler et al. |
| 2011/0182306 A1 | 7/2011 | Hosseini et al. |
| 2011/0184334 A1 | 7/2011 | Altshuler et al. |
| 2011/0207075 A1 | 8/2011 | Altshuler et al. |

(56) References Cited

U.S. PATENT DOCUMENTS

| | | | |
|---|---|---|---|
| 2011/0257584 A1 | 10/2011 | Altshuler et al. | |
| 2011/0264083 A1 | 10/2011 | Welches et al. | |
| 2011/0267830 A1 | 11/2011 | Altshuler et al. | |
| 2011/0313408 A1 | 12/2011 | Tankovich et al. | |
| 2012/0022510 A1 | 1/2012 | Welches et al. | |
| 2012/0023129 A1 | 1/2012 | Vedula et al. | |
| 2012/0046653 A1 | 2/2012 | Welches et al. | |
| 2012/0083862 A1 | 4/2012 | Altshuler et al. | |
| 2012/0099816 A1 | 4/2012 | Wilson | |
| 2012/0116271 A1 | 5/2012 | Caruso et al. | |
| 2012/0165725 A1 | 6/2012 | Chomas et al. | |
| 2012/0253222 A1 | 10/2012 | Welches et al. | |
| 2012/0277659 A1 | 11/2012 | Yaroslavsky et al. | |
| 2012/0301842 A1 | 11/2012 | Altshuler et al. | |
| 2013/0035675 A1 | 2/2013 | Mirkov et al. | |
| 2013/0096546 A1 | 4/2013 | Mirkov et al. | |
| 2013/0178917 A1 | 7/2013 | Mirkov et al. | |
| 2013/0296835 A1 | 11/2013 | Sierra et al. | |
| 2014/0025033 A1 | 1/2014 | Mirkov et al. | |
| 2014/0092926 A1* | 4/2014 | Seelert | H01S 5/041 372/29.02 |
| 2014/0321484 A1 | 10/2014 | Robertson et al. | |
| 2014/0371730 A1 | 12/2014 | Sierra et al. | |
| 2015/0005759 A1 | 1/2015 | Welches et al. | |
| 2015/0080863 A1 | 3/2015 | Welches et al. | |
| 2015/0216598 A1 | 8/2015 | Welches et al. | |
| 2016/0128777 A1 | 5/2016 | Welches | |
| 2018/0026417 A1 | 1/2018 | Sierra et al. | |

FOREIGN PATENT DOCUMENTS

| | | |
|---|---|---|
| CN | 2053926 U | 3/1990 |
| CN | 1073607 A | 6/1993 |
| CN | 1182572 A | 5/1998 |
| CN | 1351483 A | 5/2002 |
| CN | 1535126 A | 10/2004 |
| DE | 2826383 | 12/1979 |
| DE | 3304230 | 8/1984 |
| DE | 8807746 | 11/1988 |
| DE | 3837248 | 5/1990 |
| DE | 3841503 | 6/1990 |
| DE | 9102407 | 7/1991 |
| DE | 3719561 | 1/1998 |
| DE | 19803460 | 8/1999 |
| DE | 19944401 | 3/2001 |
| DE | 10112289 | 8/2001 |
| DE | 10140715 | 3/2002 |
| DE | 10120787 | 1/2003 |
| EP | 0000593 | 2/1979 |
| EP | 0142671 | 5/1985 |
| EP | 0172490 | 2/1986 |
| EP | 0297360 | 1/1989 |
| EP | 0320080 | 6/1989 |
| EP | 0324120 | 7/1989 |
| EP | 0413025 | 2/1991 |
| EP | 0458576 | 11/1991 |
| EP | 0563953 | 10/1993 |
| EP | 0565331 | 10/1993 |
| EP | 0575274 | 12/1993 |
| EP | 0593375 | 4/1994 |
| EP | 0598984 | 6/1994 |
| EP | 0709941 | 5/1996 |
| EP | 0724894 | 8/1996 |
| EP | 0726083 | 8/1996 |
| EP | 0736308 | 10/1996 |
| EP | 0743029 | 11/1996 |
| EP | 0755698 | 1/1997 |
| EP | 0763371 | 3/1997 |
| EP | 0765673 | 4/1997 |
| EP | 0765674 | 4/1997 |
| EP | 0783904 | 7/1997 |
| EP | 0884066 | 12/1998 |
| EP | 0885629 | 12/1998 |
| EP | 0920840 | 6/1999 |
| EP | 0927544 | 7/1999 |
| EP | 1031414 | 8/2000 |
| EP | 1038505 | 9/2000 |
| EP | 1057455 | 12/2000 |
| EP | 1072402 | 1/2001 |
| EP | 1075854 | 2/2001 |
| EP | 1138269 | 4/2001 |
| EP | 1138349 | 10/2001 |
| EP | 1147785 | 10/2001 |
| EP | 1219258 | 7/2002 |
| EP | 1226787 | 7/2002 |
| EP | 1238683 | 9/2002 |
| EP | 1250893 | 10/2002 |
| EP | 1057454 | 11/2003 |
| EP | 1457234 | 9/2004 |
| EP | 1495735 | 1/2005 |
| EP | 1512373 | 3/2005 |
| EP | 1535582 | 6/2005 |
| EP | 1627662 | 2/2006 |
| EP | 1650615 | 4/2006 |
| EP | 1797836 | 6/2007 |
| EP | 1839705 | 10/2007 |
| EP | 1854505 | 11/2007 |
| FR | 2199453 | 4/1974 |
| FR | 2591902 | 6/1987 |
| GB | 1251424 | 10/1971 |
| GB | 1274017 | 5/1972 |
| GB | 1546625 | 5/1979 |
| GB | 2044908 | 10/1980 |
| GB | 2059053 | 4/1981 |
| GB | 2059054 | 4/1981 |
| GB | 2123287 | 2/1984 |
| GB | 2212010 | 7/1989 |
| GB | 2239675 | 7/1991 |
| GB | 2270159 | 3/1994 |
| GB | 2356570 | 5/2001 |
| GB | 2360461 | 9/2001 |
| GB | 2360946 | 10/2001 |
| GB | 2364376 | 1/2002 |
| GB | 2368020 | 4/2002 |
| GB | 2390021 | 12/2003 |
| GB | 2397528 | 7/2004 |
| JP | S54129791 A | 10/1979 |
| JP | S5552766 A | 4/1980 |
| JP | S5577187 A | 6/1980 |
| JP | S574007 A | 1/1982 |
| JP | S62165985 A | 7/1987 |
| JP | S6323648 A | 1/1988 |
| JP | S63249577 A | 10/1988 |
| JP | S6427554 A | 1/1989 |
| JP | H0366387 A | 3/1989 |
| JP | S6481222 A | 3/1989 |
| JP | H01181877 A | 7/1989 |
| JP | H02199 | 1/1990 |
| JP | H022199 A | 1/1990 |
| JP | H0213014 U | 1/1990 |
| JP | H0285694 | 3/1990 |
| JP | H02174804 A | 7/1990 |
| JP | H02285694 A | 11/1990 |
| JP | H0319385 A | 1/1991 |
| JP | H0316956 U | 2/1991 |
| JP | H03183184 A | 8/1991 |
| JP | H03281390 | 12/1991 |
| JP | H0622871 A | 2/1994 |
| JP | H06154239 A | 6/1994 |
| JP | H079179 A | 1/1995 |
| JP | H0763957 A | 3/1995 |
| JP | H07328025 A | 12/1995 |
| JP | H0815539 A | 1/1996 |
| JP | H0854538 A | 2/1996 |
| JP | H0984803 A | 3/1997 |
| JP | H09141869 A | 6/1997 |
| JP | H09220292 A | 8/1997 |
| JP | H1014661 A | 1/1998 |
| JP | H0199574 A | 4/1998 |
| JP | H1147146 A | 2/1999 |
| JP | H11232229 A | 5/1999 |
| JP | 2000037400 A | 2/2000 |
| JP | 2000153003 A | 6/2000 |

(56) References Cited

FOREIGN PATENT DOCUMENTS

| | | |
|---|---|---|
| JP | 2000300684 A | 10/2000 |
| JP | 2001000560 A | 1/2001 |
| JP | 2001029124 A | 2/2001 |
| JP | 2001145520 A | 5/2001 |
| JP | 2001196665 A | 7/2001 |
| JP | 2001343560 A | 12/2001 |
| JP | 2002272861 A | 9/2002 |
| JP | 2003052843 A | 2/2003 |
| JP | 2005017796 A | 1/2005 |
| JP | 2005027702 A | 2/2005 |
| JP | 2006192073 A | 7/2006 |
| RU | 2082337 | 6/1997 |
| RU | 2089126 | 9/1997 |
| RU | 2089127 | 9/1997 |
| RU | 2096051 | 11/1997 |
| RU | 2122848 | 12/1998 |
| WO | WO 1986002783 | 5/1986 |
| WO | WO 1988004592 | 6/1988 |
| WO | WO 1990000420 | 1/1990 |
| WO | WO 1990006727 | 6/1990 |
| WO | WO 1990012548 | 11/1990 |
| WO | WO 1991001053 | 1/1991 |
| WO | WO 1991002562 | 3/1991 |
| WO | WO 1991012050 | 8/1991 |
| WO | WO 1991013652 | 9/1991 |
| WO | WO 1991013653 | 9/1991 |
| WO | WO 1991018646 | 12/1991 |
| WO | WO 1992016338 | 1/1992 |
| WO | WO 1992003977 | 3/1992 |
| WO | WO 1992006739 | 4/1992 |
| WO | WO 1992019165 | 11/1992 |
| WO | WO 1993005920 | 4/1993 |
| WO | WO 1993021843 | 11/1993 |
| WO | WO 1995003089 | 2/1995 |
| WO | WO 1995004393 | 2/1995 |
| WO | WO 1995010243 | 4/1995 |
| WO | WO 1995014251 | 5/1995 |
| WO | WO 1995015725 | 6/1995 |
| WO | WO 1995032441 | 11/1995 |
| WO | WO 1995033518 | 12/1995 |
| WO | WO 1996009853 | 4/1996 |
| WO | WO 1996018347 | 6/1996 |
| WO | WO 1996022741 | 8/1996 |
| WO | WO 1996022813 | 8/1996 |
| WO | WO 1996023447 | 8/1996 |
| WO | WO 1996024182 | 8/1996 |
| WO | WO 1996024406 | 8/1996 |
| WO | WO 1996025979 | 8/1996 |
| WO | WO 1996028212 | 9/1996 |
| WO | WO 1996034316 | 10/1996 |
| WO | WO 1996036396 | 11/1996 |
| WO | WO 1996039734 | 12/1996 |
| WO | WO 1996041579 | 12/1996 |
| WO | WO 1997000777 | 1/1997 |
| WO | WO 1997013458 | 4/1997 |
| WO | WO 1997013552 | 4/1997 |
| WO | WO 1997022384 | 6/1997 |
| WO | WO 1997028752 | 8/1997 |
| WO | WO 1997037602 | 10/1997 |
| WO | WO 1997037723 | 10/1997 |
| WO | WO 1998004317 | 2/1998 |
| WO | WO 1998005286 | 2/1998 |
| WO | WO 1998005380 | 2/1998 |
| WO | WO 1998006456 | 2/1998 |
| WO | WO 1998007379 | 2/1998 |
| WO | WO 1998020937 | 5/1998 |
| WO | WO 1998024507 | 6/1998 |
| WO | WO 1998029134 | 7/1998 |
| WO | WO 1998041158 | 9/1998 |
| WO | WO 1998051235 | 11/1998 |
| WO | WO 1998052481 | 11/1998 |
| WO | WO 1998058595 | 12/1998 |
| WO | WO 1999010046 | 3/1999 |
| WO | WO 1999017666 | 4/1999 |
| WO | WO 1999017667 | 4/1999 |
| WO | WO 1999017668 | 4/1999 |
| WO | WO 1999027997 | 6/1999 |
| WO | WO 1999029243 | 6/1999 |
| WO | WO 1999034867 | 7/1999 |
| WO | WO 1999038569 | 8/1999 |
| WO | WO 1999039410 | 8/1999 |
| WO | WO 1999043387 | 9/1999 |
| WO | WO 1999044638 | 9/1999 |
| WO | WO 1999046005 | 9/1999 |
| WO | WO 1999049937 | 10/1999 |
| WO | WO 1999058195 | 11/1999 |
| WO | WO 1999062472 | 12/1999 |
| WO | WO 1999066988 | 12/1999 |
| WO | WO 2000002491 | 1/2000 |
| WO | WO 2000003257 | 1/2000 |
| WO | WO 2000007514 | 2/2000 |
| WO | WO 2000030714 | 6/2000 |
| WO | WO 2000032272 | 6/2000 |
| WO | WO 2000040266 | 7/2000 |
| WO | WO 2000041278 | 7/2000 |
| WO | WO 2000043070 | 7/2000 |
| WO | WO 2000044294 | 8/2000 |
| WO | WO 2000053113 | 9/2000 |
| WO | WO 2000054649 | 9/2000 |
| WO | WO 2000054685 | 9/2000 |
| WO | WO 2000062700 | 10/2000 |
| WO | WO 2000064537 | 11/2000 |
| WO | WO 2000066226 | 11/2000 |
| WO | WO 2000071045 | 11/2000 |
| WO | WO 2000074583 | 12/2000 |
| WO | WO 2000074781 | 12/2000 |
| WO | WO 2000078242 | 12/2000 |
| WO | WO 2001014012 | 3/2001 |
| WO | WO 2001026573 | 4/2001 |
| WO | WO 2001034048 | 5/2001 |
| WO | WO 2001042671 | 6/2001 |
| WO | WO 2001054606 | 8/2001 |
| WO | WO 2001054770 | 8/2001 |
| WO | WO 2001078830 | 10/2001 |
| WO | WO 2002009813 | 2/2002 |
| WO | WO 2002026147 | 4/2002 |
| WO | WO 2001003257 | 7/2002 |
| WO | WO 2002053050 | 7/2002 |
| WO | WO 2002069825 | 9/2002 |
| WO | WO 2002078559 | 10/2002 |
| WO | WO 2002094116 | 11/2002 |
| WO | WO 2003005883 | 1/2003 |
| WO | WO 2003049633 | 6/2003 |
| WO | WO 2003103529 | 12/2003 |
| WO | WO 2004000150 | 12/2003 |
| WO | WO 2004011848 | 2/2004 |
| WO | WO 2004033040 | 4/2004 |
| WO | WO 2004037068 | 5/2004 |
| WO | WO 2004037287 | 5/2004 |
| WO | WO 2004073537 | 9/2004 |
| WO | WO 2004080279 | 9/2004 |
| WO | WO 2004084752 | 10/2004 |
| WO | WO 2004086947 | 10/2004 |
| WO | WO 2005007003 | 1/2005 |
| WO | WO 2005009266 | 2/2005 |
| WO | WO 2005030317 | 4/2005 |
| WO | WO 2005046793 | 5/2005 |
| WO | WO 2005065288 | 7/2005 |
| WO | WO 2005092438 | 10/2005 |
| WO | WO 2005096981 | 10/2005 |
| WO | WO 2005099369 | 10/2005 |
| WO | WO 2005112815 | 12/2005 |
| WO | WO 2006006123 | 1/2006 |
| WO | WO 2006036968 | 4/2006 |
| WO | WO 2006066226 | 6/2006 |
| WO | WO 2006089227 | 8/2006 |
| WO | WO 2006101735 | 9/2006 |
| WO | WO 2006116141 | 11/2006 |
| WO | WO 2007035444 | 3/2007 |
| WO | WO 2007122611 | 11/2007 |
| WO | WO 2008007218 | 1/2008 |
| WO | WO 2008070747 | 6/2008 |
| WO | WO 2008153999 | 12/2008 |

(56) References Cited

FOREIGN PATENT DOCUMENTS

| | | |
|---|---|---|
| WO | WO 2010102255 | 9/2010 |
| WO | WO 2012023129 | 2/2012 |
| WO | WO 2014145707 | 9/2014 |

OTHER PUBLICATIONS

Qiu et al. "Performance of a Nd:YVO4 microchip laser with continuous-wave pumping at wavelengths between 741 and 825 nm", Appl. Opt. v.32, No. 12, p. 2085, 1993 (Year: 1993).*

[No Author] Bioptron Light Therapy System. Website print-out, accessed Jul. 13, 2006 (2 pages).

[No Author] Derma Chiller advertisement (2 pages) from Paradigm Trex.

[No Author] IPG Data Sheet for TFL Thulium Laser, Jun. 2001.

[No Author] Webpage www.gallery.com—Rutile (Titanium Oxide)—Retrieved Oct. 3, 2011 from Http://www.galleries.com/minerals/oxides/rutile/rutile.htm. 2 pages.

[No Author] Altea Therapeutics—Medicines Made Better (single page website print-out, retrieved Sep. 30, 2004, © 2003-2004).

[No Author] Energy Systems Coropration, "A Practical Guide for the PhotoDern.RTM.VL user," Haifa, Israel, Commercial Brochure 8 Pages, Oct. 1995.

[No Author] "Final Report on the LFDL-10 Laser System for the GCA Corporation," Candela Corp., Natick, MA, Section II, subsection 5, pp. 13-15 & 27, Mar. 1982.

[No Author] "Fractional Photothermolysis Redefines Facial Skin Regeneration Science," Aesthetic Buyers Guide, Mar./Apr. 2004, www.miinews.com, pp. 1-4.

[No Author] "Hydrogel Dressings Contain Particles During Laser Therapy," Dermatology Times, ISSN-01966197, p. 26 (1994).

[No Author] "Instruction Manual, TFDL-10," Adapted for SLAC, Candela Corporation, Natick, Oct. 1985.

[No Author] "Lasers Battle for Prostatectomy Market," Medical Laser Industry Report, 5:1-3 (Aug. 1991).

[No Author] "LFDL-8 Instruction Manual," Candela Laser Corporation, Wayland, MA Revised Oct. 1987.

[No Author] "LFDL-8 Instruction Manual," Candela Laser Corporation, Wayland, MA, Jan. 1982, Revised Jun. 1987.

[No Author] "LFDL-8 Instruction Manual," Cynosure, Inc., Bedford, MA, Revised Nov. 1992.

[No Author] "Prostate Enlargement: Benigh Prostatic Hyperplasia," brochure from U.S. Department of Health and Human Services, pp. 1-14, (at least by 1992).

[No Author] "Special Instruction and Test Results for the LFDL-2 Wave Guide Laser," Candela Laser Corporation, Wayland, MA, Sep. 1982.

[No Author] "The Laser TURP Advantage," Intra-Sonix, Inc. pp. 1-4 (1991).

[No Author] Beckman Laser Institute "Experimental PDT to Prevent Esophagus Cancer," (8 pages) 1996.

[No Author] Cynosure Dioderm 510(k) Notification K992765 for Cynosure, Inc. to Food and Drug Administration, dated: Aug. 16, 1999 and Aug. 20, 1999 (Additional Information).

[No Author] Reliant Technologies, Inc. "Physicians Guide: Understanding Faxel Laser Treatment," pp. 1-10 (2004).

[No Author] Ritter Sybron Corporation, "Electrosurgery, A Guide for Operating Room Personnel," pp. 1-22, (Jun. 1976).

[No Author] Selective Photothermolysis of Sebaceous Glands, Department of Health and Human Services, Public Health Service, Small Business Innovation Research Program II Grant Application, Cynosure, Inc., dated: Jul. 27, 2000, pp. 17-39 and 43-44.

[No Author] "Innovative Non-Surgical Treatment for Barrett's Esophagus", Jul., 1995, see http://www.plsgroup.com/dg950728.htm.

"American Society for Laser Medicine and Surgery Abstracts," Lasers in Surgery and Medicine, Supplement 6, p. 46 (1994).

Anderson, R.R., et al., "Microvasculature Can Be Selectively Damaged Using Dye Lasers: A Basic Theory and Experimental Evidence in Human Skin," Lasers in Surgery and Medicine 1:263-276 (1981).

Altshuler et al., "Human Tooth as an Optical Device," SPIE vol. 1429 Holography and Interferometry and Optical Pattern Recognition in Biomedicine, pp. 95-104, 1991.

Altshuler et al., "Modern Optics and Dentistry," Laser in Dentistry, pp. 283-297, 1995.

Altshuler et al., "New Optical Effects in the Human Hard Tooth Tissues," Lasers and Medicine, Proc. SPIE vol. 1353, pp. 97-102, 1989.

Altshuler, et al., "Self Canalization of Laser Microbeam in Tissue as Fundamental Mechanism of Fractional Skin Resurfacing", Lasers in Surgery and Medicine Supple 15, 21, 2003.

Altshuler, G.B. et al., "Acoustic response of hard dental tissues to pulsed laser action," SPIE, vol. 2080, Dental Application of Lasers, pp. 97-103, 1993.

Altshuler, G.B. et al., "Extended theory of selective photothermolysis," Lasers in Surgery and Medicine, vol. 29, pp. 416-432, 2001.

Amy, R.L. et al., "Selective mitochondrial damage by a ruby laser microbeam: An electron microscopic study," Science, vol. 15, pp. 756-758, Nov. 1965.

Anderson, R.R. et al., "Selective photothermolysis: Precise microsurgery by selective absorption of pulsed radiation," Science, vol. 220, pp. 524-527, Apr. 1983.

Anderson, R.R. et al., "The optics of human skin," Journal of Investigative Dermatology, vol. 77, No. 1, pp. 13-19, 1981.

Ang et al., "Kalman Filtering for Real-Time Orientation Tracking of Handheld . . . ", 2004 IEEE/RSJ Iner Conf on Intell Robots and Systems (IROS), Sendai, Japan.

Ang et al., "Design of All-Accelerometer Inertial Measurement Unit for Tremor Sensing in Hand-Held . . . ", 2003 IEEE Inter Conf on Robotice and Automation (col. 2), Taipei, Taiwan.

Angelis, et al., "Fractional, Non-Ablative Laser Therapy for the Treatment of Striae Distensae", White Paper published by Palomar Medical Technologies, Inc. (2009)5 pages.

Apfelberg et al. "Analysis of Complications of Argon Laser Treatment for Port Wine Hemangiomas with Reference to Striped Technique," Lasers in Surgery and Medicine, 2:357-371 (1983).

Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987).

Apfelberg, D.B., "A Preliminary Study of the Combined Effect of Neodymium: YAG Laser Photocoagulation and Direct Steroid Instillation in the Treatment of Capillary/Cavernous Hemangiomas of Infancy," Department of Plastic Surgery and Comprehensive Laser Center, Palo Alto Medical Foundation, Palo Alto, CA, pp. 94-103 (1989).

Apfelberg, D.B., "Combination Treatment for Massive Cavernous Hemangioma of the Face: YAG Laser Photocoagulation Pulse Direct Steroid Injection Followed by YAG Laser Resection with Sapphire Scalpel Tips, Aided by Superselective Embolization," Lasers in Surgery and Medicine, 10:217-223 (1990).

Belikov, A.V. et al., "Identification of enamel and dentine under tooth laser treatment," SPIE vol. 2623, Progress in Biomedical Optics Europt Series, Proceedings of Medical Applications of Lasers III, pp. 109-116, Sep. 1995.

Benjavitvilai, C. et al., "Fuzzy Calibration of Magnetometer in Presence of Surgical Microscope," 2005 27th Annual International Conference of the IEEE Engineering in Medicine and Biology Society (IEEE Cat. No. 05CH37611C), Shanghai, China, Aug. 31-Sep. 3, 2005.

Bjerring, P. et al., "Selective Non-Ablative Wrinkle Reduction by Laser," J Cutan Laser Ther, vol. 2, pp. 9-15, 2000.

Blankenau et al., "In Vivo Caries-Like Lesion Prevention with Argon Laser: Pilot Study," Journal of Clinical Laser Medicine and Surgery, vol. 17, No. 6, pp. 241-243, 1999.

Bogdan Allemann, et al., "Laser Principles", Physical and Electronic Properties of Lasers, Basics in Dermatological Laser Applications, Curr. Probl. Dermatol, Basel, Karger. Zurich, Switzerland and Miami, Florida. vol. 42, pp. 7-23, 2011, 17 pages.

(56) References Cited

OTHER PUBLICATIONS

Bohm et al., "The Pilosebaceous Unit is Part of the Skin Immune System," Dermatology, 196:75-79, 1998.

Boiteux, M., et al., "A Transverse Flow Repetitive Dye Laser," Applied Optics, 9, 514 (1970).

Boulnois, J., "Photophysical Processes in Recent Medical Laser Developments: a Review," Lasers in Medical Science, vol. 1:47-66 (1986).

Brauer, Jeremy A. et al., "Successful and Rapid Treatment of Blue and Green Tattoo Pigment With a Novel Picosecond Laser", Archives of Dermatology, vol. 148, No. 7, 2012, pp. 820-823.

Britt et al., "The Effect of pH or Photobleaching of Organic Laser Dyes", IEEE J. Quantum Electron. (Dec. 1972), 913-914.

Burlamacchi et al, "A Simple Reliable Waveguide Dye Laser for Ophthalmological Applications," Rev of Sci Instrum; vol. 46; No. 3; pp. 281-283, Mar. 1975.

Chan, E.K., "Effects of Compression on Soft Tissue Optical Properties," IEEE Journal of Selected Topics in Quantum Electronics, vol. 2, No. 4, pp. 943-950 (Dec. 1996).

Costello, A. et al., "Nd:YAG Laser Ablation of the Prostate as a Treatment for Benign Prostatic Hypertrophy," Lasers in Surgery and Medicine, 12:121-124 (1992).

Cox et al., "Short-cavity picosecond dye laser design", Applied Optics, 18:4, Feb. 15, 1979 (4 pages).

Cunliffe, "Acne Vulgaris. The Past, the Present and the Future," Acta Bermatovener (Stockh) Suppl. 120, pp. 34-38, 1985.

Dabrowska, "Intravital Treatment of the Pulp with Stimulation Laser Biostimulation," Abstract Rocz-Akad-Med-Bialymst. 1997; 42(1): 168-76.

Dierickx, C.C. et al., "Thermal Relaxation of Port-wine Stain Vessels Probed In Vivo: The Need for 1-10 Millisecond Laser Pulse Treatment," The Journal for Investigative Dermatology, pp. 709-714 (1995).

Dixon et al. "Hypertrophic Scarring in Argon Laser Treatment of Port-Wine Stains," Plastic and Reconstructive Surgery, 73:771-777 (1984).

Dock et al., "Clinical Histologic and Ultrastructural Evaluation of Solar Elastosis Treated With the Pulsed Dye Laser," American Society for Laser Medicine and Surgery Abstracts, p. 54 (Apr. 1997).

Doukas et al., "Transdermal Drug Delivery With a Pressure Wave," Advanced Drug Delivery Reviews 56 (2004), pp. 559-579.

Dover J.S. et al., "Pigmented guinea pig skin irradiated with Q-switched ruby laser pulses," Arch Dermatol, vol. 125, pp. 43-49, Jan. 1989.

Dufresne et al., "Squamous cell carcinoma arising from the follicular occlusion triad," J. Am. Acad. Dermatol. 35(3), Part 1:475-477, 1996.

Ellenberger, et al. "Single-Frequency Nd:Glass Laser Oscillator with Pulse-Transmission-Mode Q-Switch with Pulse-Transmission-Mode Q-Switch," Optics communication, vol. 81, No. 6 (Mar. 1991).

Ertan et al., "Esophagel Adenocarcinoma Associated with Barrett's Esophagus: Long-term Management with Laser Ablation", Am. J. Gastro, 90: pp. 2201-2203, 1995.

Fallon Friedlander, "Effective Treatment of Acne Fulminans-Associated Granulation Tissue with the Pulsed Dye Laser," Pediatric Dermatology, 15(5):396-398, 1998.

Finkelstein L.H. et al., "Epilation of hair-bearing urethral grafts using the neodymium:yag surgical laser," Journal of Urology, vol. 146, pp. 840-842, Sep. 1991.

Fiskerstrand E.J. et al., "Hair Removal with Long Pulsed Diode Lasers: A Comparison Between Two Systems with Different Pulse Structures," Lasers in Surgery and Medicine, vol. 32, pp. 399-404, 2003.

Fletcher, A.N. et al., "Improving the Output and Lifetime of Flashlamp-Pumped Dye Lasers" Proceedings of the International Conference on Lasers '85, pp. 797-804, Dec. 2-6, 1985.

Forrest-Winchester et al., "The Effect of Infrared Laser Radiation on Dentinal Permeability in vitro," Department of Dentistry, University of Queensland Dental School, pp. 1-8, 1992.

Friedman-Birnbaum et al., "Seborrheic Skin and Acne Vulgaris as Protective Factors against the Development of Basal Cell Epithelioma," Dermatolgica, 183:160-163, 1991.

Furumoto, H., "Dye Chemistry and System Study for Optimum Laser Operation at 436 NM Using the LFDL-10 Laser," Prepared for Burlington Division Geophysical Corporation of America, pp. 1-23, Mar. 1982.

Ginsbach et al. "New Aspects in the Management of Benign Cutaneous Tumors," Laser 79 Opto-Electronics, Munich Conference Proceedings, 344-347 (1979).

Goldberg, "Lasers for Facial Rejuvenation", Am J. Clin. Dermatol., 4(4):225-234, 2003, 10 pages.

Goldberg, "Nonablative Resurfacing", Clinics in Plastic Surgery, Skin Laser and Surgery Specialists of New York and New Jersey. Westwood, New Jersey. vol. 27, No. 2, Apr. 2000, 6 pages.

Goldman, L. et al. "Treatment of basal cell epithelioma by laser radiation," JAMA, vol. 189, No. 10, pp. 773-775, 1964.

Goldman, L. et al., "Effect of the laser beam on the skin, III. Exposure of cytological preparations," Journal of Investigative Dermatology, vol. 42, pp. 247-251, 1964.

Goldman, L. et al., "Effect of the laser beam on the skin, Preliminary report" Journal of Investigative Dermatology, vol. 40, pp. 121-122, 1963.

Goldman, L. et al., "Impact of the laser on nevi and melanomas," Archives of Dermatology, vol. 90, pp. 71-75, Jul. 1964.

Goldman, L. et al., "Laser action at the cellular level," JAMA, vol. 198, No. 6, pp. 641-644, Nov. 1966.

Goldman, L. et al., "Laser treatment of tattoos, A preliminary survey of three year's clinical experience," JAMA, vol. 201, No. 11, pp. 841-844, Sep. 1967.

Goldman, L. et al., "Long-term laser exposure of a senile freckle," ArchEnviron Health, vol. 22, pp. 401-403, Mar. 1971.

Goldman, L. et al., "Pathology, Pathology of the effect of the laser beam on the skin," Nature, vol. 197, No. 4870, pp. 912-914, Mar. 1963.

Goldman, L. et al., "Preliminary investigation of fat embolization from pulsed ruby laser impacts of bone," Nature, vol. 221, pp. 361-363, Jan. 1969.

Goldman, L. et al., "Radiation from a Q-switched ruby laser, EffeCt of repeated impacts of power output of 10 megawatts on a tattoo of man," Journal of Investigative Dermatology, vol. 44, pp. 69-71, 1965.

Goldman, L. et al., "Replica microscopy and scanning electron microscopy of laser impacts on the skin," Journal of Investigative Dermatology, vol. 52, No. 1, pp. 18-24, 1969.

Goldman, L. et al., "The biomedical aspects of lasers," JAMA, vol. 188, No. 3, pp. 302-306, Apr. 1964.

Goldman, L. et al., "The effect of repeated exposures to laser beams," Acta derm.-vernereol., vol. 44, pp. 264-268, 1964.

Goldman, L., "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.

Goldman, L., "Effects of new laser systems on the skin," Arch Dermatol., vol. 108, pp. 385-390, Sep. 1973.

Goldman, L., "Laser surgery for skin cancer," New York State Journal of Medicine, pp. 1897-1900, Oct. 1977.

Goldman, L., "Surgery by laser for malignant melanoma," J. Dermatol. Surg. Oncol., vol. 5, No. 2, pp. 141-144, Feb. 1979.

Goldman, L., "The skin," Arch Environ Health, vol. 18, pp. 434-436, Mar. 1969.

Goldman, L., Biomedical Aspects of the Laser, Springer-Verlag New York Inc., publishers, Chapts. 1, 2 & 23, 1967.

Goldman, M. P., "Leg Veins and Lasers," American Society for Laser Medicine and Surgery Abstracts, Fourteen Annual Meeting, Toronto, Ontario, Canada, p. 48 (Apr. 8-10, 1994).

Goldman, M.P., "Sclerotherapy—Treatment of Varicose and Telangiectatic Leg Veins," Second Edition, Mosby, pp. 454-467 (1995).

(56) References Cited

OTHER PUBLICATIONS

Gottlieb, I., "Power Supplies, Switching Regulators, Inverters & Converters," 1976.

Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981).

Grossman, et al., "780 nm Low Power Diode Laser Irradiation Stimulates Proliferation of Keratinocyte Cultures: Involvement of Reactive Oxygen Species," Lasers in Surgery and Medicine vol. 29, pp. 212-218, 1998.

Grossman, M.C. et al., "Damage to hair follicles by normal-mode ruby laser pulses," Journal of he American Academy of Dermatology, vol. 35, No. 6, pp. 889-894, Dec. 1996.

Grossman, M.C. et al., "Laser Targeted at Hair Follicles," Lasers Med Surg., Suppl. 13:221 (2001).

Habbema, Louis et al., "Minimally invasive non-thermal laser technology using laser-induced optical breakdown fir skin rejuvenation", J. Biophotonics, vol. 5, No. 2, 2012, pp. 194-199.

Haedersal, et el., "Fractional Nonablative 1540 nm Laser Resurfacing for Thermal Burn Scars: A Randomized Controlled Trial", Lasers in Surgery and Medicine, 41:189-195, 2009, 7 pages.

Hicks et al., "After Low Fluence Argon Laser and Flouride Treatment," Compendium, vol. 18, No. 6, Jun. 1997.

Hicks et al., "Enamel Carries Initiation and Progression Following Low Fluence (energy) and Argon Laser and Fluoride Treatment," The Journal of Clinical Pediatric Dentistry, vol. 20, No. 1 pp. 9-13, 1995.

Hsu et al., "Combined Effects of Laser Irradiation/Solution Flouride Ion on Enamel Demineralization," Journal of Clinical Laser Medicine and Surgery, vol. 16, No. 2 pp. 93-105, 1998.

Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984).

Hulsbergen Henning et al., "Port Wine Stain Coagulation Experiments with a 540-nm Continuous Wave Dye-Laser," Lasers in Surgery and Medicine, 2:205-210 (1983).

Invention description to certificate of authorship, No. 719439, "The ring resonator of optical quantum generator" (Aug. 15, 1975).

Invention description to certificate of authorship, No. 741747, "The modulator of optical radiation intensity" (Oct. 10, 1977).

Invention description to certificate of authorship, No. SU 1257475 A1, "Laser interferometric device to determine no-linearity of an index of refraction of optical medium" (Sep. 15, 1986).

Invention description to certificate of authorship, No. SU 1326962 A1, "The way of determination of non-linearity of an index of refraction of optical medium" (Jul. 30, 1987).

Invention description to certificate of 45uthorship, No. 532304, "The way of investigation of radiation time structure of optical quantum generator" (Jul. 9, 1974).

Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987).

Johnsson et al., "No photoinactivation of Propionibacterium acnes with soft laser treatment," Dermatologica, 175(1):50, 1987.

Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230.

Kandel, Laurence B., M.D., et al., "Transurethral Laser Prostatectomy in the Canine Model," Lasers in Surgery and Medicine, 12:33-42 (1992).

Kantor et al., "Treatment of acne keloidalis nuchae with carbon dioxide laser," J. Am. Acad. Dermatol., 14:263-267, 1986.

Karu, "Cell Attachment to Extracellular Matrics is Modulated by Pulsed Radiation at 820 nm and Chemicals that Modify the Activity of Enzymes in the Plasma Membrane," Laser in Surgery and Medicine, vol. 29, pp. 274-281, 2001.

Karu, "Photobiological Fundamentals of Low-Power Laser Therapy," $8^{th}$ Congress of International Society for Laser Surgery and Medicine, Mar. 30, 1987.

Kazmina et al., "Laser Prophlaxis and Treatment of Primary caries," SPIE vol. 1984, pp. 231-233.

Kelly et al., "Nonablative Laser Treatment of Facial Rhytides: United States Phase II Clinical Study," American Society for Laser Medicine and Surgery Abstracts, 10(33):38 (1998).

Kilmer et al., "Pulse Dye Laser Treatment of Rhytids," American Society for Laser Medicine and Surgery Abstracts, p. 44 (Apr. 1997).

Klein, E. et al., "Biological effects of laser radiation 1.," Northeast Electroncis Research and Engineering Meeting, NEREM Record, IEEE catalogue No. F-60, pp. 108-109, 1965.

Kliewer, Michael L. et al., "Excited State Absorption of Pump Radiation as a Loss Mechanism in Solid-State Lasers", IEEE Journal of Quantum Electronics, vol. 25, 1989, pp. 1850-1854.

Korobov et al., "Dependence of the Quantum Yield of Intercombinational Conversion into the Triplet State of Rhodamine 6G on the pH of the Medium", Zhur. Prikl. Spektrosk. 24(1) 28-31 (Jan. 1976).

Kozlov et al., "Laser in Diagnostics and Treatment of Microcirculation Disorders Under Parodontitis," SPIE vol. 1984, pp. 253-264.

Krames et al. "Status and Future of High-Power Light-Emitting Diodes for Solid State Lighting", J. Display Technol., 3(2):160-175 (Jun. 2007).

Kuhns, J.G. et al., "Biological effects of laser radiation II Effects of laser irradiation on the skin," NEREM Record, pp. 152-153, 1965.

Kuhns J.G. et al., "Laser injury in skin," Laboratory Investigation, vol. 17, No. 1, pp. 1-13, Jul. 1967.

Kuizenga, Dirk J. et al., "FM and AM Mode Locing of the Homogenous Laser—Part I: Theory", IEEE Journal of Quantum Electronics, vo. 6, No. 11, Nov. 1970, pp. 694-708.

Lee, Junsu et al., "Q-switched Mode-Locking of an Erbium-doped Fiber Laser through Subharmonic Cavity Modulation", Photonics Conference (IPC), 202 IEEE, Sep. 23, 2012, pp. 664-665.

Leger, J. et al., "Geometrical Transformation of Linear Diode-Laser Arrays for Longitudinal Pumping of Solid-State Lasers", IEEE Journal of Quantum Electronics, vol. 28, No. 4, Apr. 1992.

Lesnik et al., "Agents that cause enlargement of sebaceous glands in hairless mice," Arch. Dermatol., 284:100-105, 1992.

Levin, G. et al., "Designing with hyseretic current-mode control," EDN Magazine, pp. 1-8, Apr. 11, 1996.

Levin, G. et al., "Designing with hyseretic current-mode control, " EDN Magazine, pp. 1-8, Apr. 28, 1994.

Lucchina et al., "Fluorescence photography in the evaluation of acne," J. Am. Acad. Dermatol. 35:58-63 (1996).

Maegawa, et al., "Effects of Near-Infrared Low-Level Laser Irradiation on Microcirculation," Lasers in Surgery and Medicine, vol. 27, pp. 427-437, 2000.

Mamedova et al., "Microbiological Estimate of Parodontis Laser Therapy Efficiency," SPIE vol. 1984, pp. 247-249.

Mang, "Effect of Soft Laser Treatment on Wound Healing in the Hamster Oral Mucosa," Lasers in Surgery and Medicine, Supp. 8, Abstracts, Abstract 25, 1996.

Manstein, D. et al., "Selective Photothermolysis of Lipid-Rich Tissue," American Society for Laser medicine and Surgery Abstracts, No. 17, American Society for Laser Medicine and Surgery Twenty-First Annual Meeting, Apr. 20-22, 2001, p. 6.

Manstein, D., et al., "Fractional Photothermolysis: A New Concept for Cutaneous Remodeling Using Microscopic Patterns of Thermal Injury," Lasers in Surgery and Medicine, 34: 426-438 (2004).

Manuskiatti et al., "Laser hair removal affects sebaceous glands and sebum excretion . . . ," J. Am. Acad. Dermatol., 41:176-180, 1999.

Margolis, R.J. et al., "Visible action spectrum for melanin-specific selective photothermolysis," Lasers in Surgery and Medicine, vol. 9, pp. 389-397, 1989.

Marinelli et al., "Diode laser illuminated automotive lamp systems," SPIE Proceedings vol. 3285:170-177 (1998).

Marshak, I.S., et al., "Pulsed Light Sources," State Power Engineering Press, Moscow and Leningrad (1963).

Matsunaga et al., "Effect of pH on Dye-Laser Output Power", J. Appl. Phys. 48(2):842-844 (Feb. 1977).

(56) References Cited

OTHER PUBLICATIONS

McCullough, David L., M.D., "Transurethral Laser Treatment of Benign Prostatic Hyperplasia," and "Transurethral Ultrasound-guided Laser-Induced Prostatectomy (TULIP) Procedure): A Canine Prostate Feasibility Study," by Roth, Robert A., M.D., et al., The Journal of Urology, 146:1126-1135 (1991).
McDaniel, et al., "Hexascan: A New Robotized Scanning Laser Handpiece," Cutis, 45:300-305 (1990).
McNicholas, T. A., et al., "Interstitial Laser Coagulation of the Prostate: Experimental Studies," SPIE, 1421:30-35 (1991). (From Proceedings of Lasers in Urol., Laparoscopy, and General Surgery, Jan. 21-23, 1991).
Mingxin, Qiu et al., "Performance of a Nd:YVO4 microchip laser with continuous-wave pumping at wavelengths between 741 and 825 nm", Applied Optics, vol. 32, No. 12, Apr. 20, 1993, p. 2085.
Moretti, Michael, "Holmium Boosts Orthopedic Laser Development," Medical Laser Buyers Guide, p. 93 (1992).
Moretti, Michael, "Lasers Improve Prostatectomy Treatment," Medical Laser Buyers Guide, p. 94-96 (1992).
Mostovnikov, V.A. et al., "Recovery of Lasing Properties of Dye Solutions after Their Photolysis," Sov. J. Quantum Electron, 6(9), Sep. 1976, pp. 1126-1128.
Nanni, C.A. et al., "Complications of Carbon Dioxide Laser Resurfacing," Washington Inst. Of Dermatol. Surg. 24:315-320 (1998).
Nemeth, et al., "Copper vapor laser treatment of pigmented lesions," Lasers Surg. Med. Supp. 2:51 (1990).
Ogiso et al, "Phase Transitions of Rat Stratum Corneum Lipids By an Electron Paramagnetic Resonance Study and Relationship of Phase States to Drug Penetration," Biochimica et Biophysica Acta 1301:97-104 (1996).
Ohbayashi, "Stimulatory Effect of Laser Irradiation on Calcified Nodule Formation in Human Dental Pulp Fibroblasts," Abstract J-Endod. Jan. 1999; 25(1): 30-3.
Ohshiro et al., "The Ruby and Argon Lasers in the Treatment of the Naevi," Annals Academy of Medicine, Apr. 1983, vol. 12, No. 2, pp. 388-395.
Oleinik, et al., "Automatized Securing Definition for Laser Therapy Indications in Case of Non-complicated Caries," SPIE, vol. 1984, pp. 238-244.
Oraevsky, Alexander A. et al., "Plasma Mediated Ablation of Biological Tissues with Nanosecond-to-Femtosecond Laser Pulses: Relative Role of Lineear and Nonlinear Absorption", IEEE Journal of Selected Topics in Quantum Electronics, vol. 2, No. 4, Dec. 1996, pp. 801-809.
Orchardson, "Effect of Pulsed Nd:YAG Laser Radiation on Action Potential Conduction in Nerve Fibres Inside Teeth in vitro," Abstract J-Dent. Jul.-Aug. 1998; 26(5-6): 421-6.
Overholt BF et al. "Balloon photodynamic therapy of esophageal cancer: effect of increasing balloon size." PubMed; Lasers Surg Med. 1996, 18(3):248-52.
Ozawa et al., "Stimulatory Effects of Low-Power Laser Irradiation on Bone Formation in vitro," SPIE vol. 1984, pp. 281-288.
Panjehpour M et al. "Spectroscopic diagnosis of esophageal cancer: new classification model, improved measurement system." PubMed; Gastrointest Endosc. Jun. 1995; 41 (6):577-81.
Parrish, J.A., "Selective thermal effects with pulsed irradiation from lasers: From organ to organelle," Journal of Investigative Dermatology, vol. 80, No. 6 Supplement, pp. 75s-80s, 1983.
Petrischev et al. "Clinical and Experimental Low-Intense Laser Therapy in Dentistry," SPIE, vol. 1984, pp. 212-214.
Petrischev et al., "Report on Low Intensity Laser Radiation Usage in Dentistry," SPIE vol. 1984, pp. 202-211.
Polanyi, Thomas & Tobias, Irwin, Lasers—A Series of Advances, Edited by A.K. Levine, vol. 2, Marcel Dekker, Inc, N.Y., 1968, pp. 400, 402-403 & 422.
Polla, L. et al., "Melanosomes are a primary target of Q-switched ruby laser irradiation in guinea pig skin," Journal of Investigative Dermatology, vol. 89, No. 3, pp. 281-286, Sep. 1987.
Powell, "Laser Dental Decay Prevention: does it have a future?" SPIE vol. 3192, 1997.
Reed J.T. et al., "Treatment of Periorbital Wrinkles," Washington Inst. Of Dermatol. Surg. 23:643-648 (1997).
Remillard et al., "Diode laser illuminated automotive brake lamp using a linear fanout diffractive optical element," Proc. Of the Diffractive Optics and Micro-Optics Conference, OSA Technical Digest Series vol. 10, 192-194 (1998).
Remillard et al., "Diode Laser Illuminators for Night-Vision Applications," SPIE Proceedings vol. 4285:14-22 (2001).
Riggle et al., "Laser Effects on Normal and Tumor Tissue," Laser Applications in Medicine and Biology, vol. 1, M.L. Wolbarsht, editor, Plenum Press, publishers, Ch. 3, pp. 35-65 (1971).
Rohrer, "Evaluating the Safety and Efficacy Of A Novel Light Based Hair Removal System," Lasers. Surg. Med. Supp. 13:97 (2001).
Rosenfeld, H., et al., "Treatment of Cutaneous and Deep Vascular Lesions with the Nd:YAG Laser," Lasers in Surgery and Medicine, 6:20-23 (1986).
Rotteleur, et al., "Robotized scanning laser handpiece for the treatment of port wine stains and other angiodysplasias," Lasers Surg. Med., 8:283-287 (1998).
Rubach et al., "Histological and Clinical Evaluation of Facial Resurfacing Using a Carbon Dioxide Laser With the Computer Pattern Generator," Arch Otolaryngol Head Neck Surg., 123:929-934 (1997).
Russel et al. "Flash-Lamp-Excited Self-Injection-Seeded Q-Switch Ti:Al2O3 Laser Oscillator," Applied Optics, vol. 35, No. 24 (Aug. 1996).
Rylander, C.G. et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008).
Sandford et al., "Thermal Effects During Desensitisation of Teeth with Gallium-Aluminum-Arsenide Lasers," University of Queensland Dental School, Periodontology 15: 25-30 (1994).
Schade, W. et al., "Temperature tuned distributed feedback dye laser with high repetition rate", Applied Optics, vol. 2 9, No. 27, Sep. 20, 1990, pp. 3950-3954.
Schappert et al., "Temperture Tuning of an Organic Dye Laser" Applied Physics Letters 13(4):124-126 (Aug. 15, 1968).
Schindl, "Does Low Intensity Laser Irradiation Really Cause Cell Damage?" Laser in Surgery and Medicine vol. 22, pp. 105, 2001.
Sheehan-Dare, et al., "Lasers in Dermatology," British Journal of Dermatology, 129:1-8 (1993).
Sheng et al., "Gain-switching of a LD end-pumped Nd:YVO4 microchip laser", Proceedings of SPIE, 5628:20, Jan. 1, (6 pages).
Shimbashi, T. et al., "Ruby laser treatment of pigmented skin lesions," Aesth. Plast. Surg., vol. 19, pp. 225-229, 1995.
Shimizu et al., "Prospect of Relieving Pain Due to Tooth Movement During Orthodontic Treatment Utilizing a GA-Al As Diode Laser," SPIE vol. 1984, pp. 275-280.
Shumilovitch et al., "Influence of Low Intensity Laser Radiation Upon the Microflora of Carious Cavities and Root Canal," SPIE vol. 1984, pp. 215-220.
Shuster, "Acne: The Ashes of a Burnt Out Controversy," Acta Derm. Venereol. Suppl. (Stockh), 120:43-46, 1985.
Sigurdsson et al., "Phototherapy of Acne Vulgaris with Visible Light," Dermatology, 194:256-260, 1997.
Sing, "Electroacupuncture and Laser Stimulation Treatment: Evaluation by Somatosensory Evoked Potential in Conscious Rabbits," Abstract AM-J-Chin-Med. 1997; 25(3-4): 263-71.
Sliney et al., "Safety with Lasers and Other Optical Sources: A Comprehensive Handbook," Plenum Press, pp. 477-480 (1980).
Sokolova et al., "Low-intense Laser Radiation in Complex Treatment of Inflammatory Diseases of Parodontium," SPIE vol. 1984, pp. 234-237.
Spears et al., "Fluorescence of Experimental Atheromatous Plaques with Hematoporphyrin Derivative," J. Clin. Invest, 71:395-399 (1983).
Spotswood, "Novel Use of Fractional Lasers for Scarring Improves Quality of Life for Injured Troops", http://www.usmedicine.com/articles/novel-use-of-fractional-lasers-for-scarring-improves-quality-of-life-for-injured-troops-.html, (Aug. 2012), U.S. Medicine ISSN: 0191-6246. 4 pages.

(56) References Cited

OTHER PUBLICATIONS

Stratton, K. et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.

Strauss et al., "Skin Lipids and Acne," Annu. Rev. Med., 26: 27-31, 1975.

Sumian, C.C. et al., "A Preliminary Clinical And Histopathological Study Of Laser Skin Resurfacing Using A frequency-Doubled Nd:YAG Laser After Application of Chromofilm®," Journal of Cutaneous Laser Therapy, vol. 1, pp. 159-166, 1999.

Sumian, C.C. et al., "Laser Skin Resurfacing Using A Frequency Doubled Nd:YAG Laser After Topical Application Of An Exogenous Chromophore," Lasers in Surgery and Medicine, vol. 25, pp. 43-50, 1999.

Sumian et al., "A new method to improve penetration depth of dyes into the follicular duct : . . . ," J. Am. Acad. Dermotol., 41(2) Part 1:172-175, 1999.

Supplemental Search Report issued by the European Patent Office for European Patent Application No. 20183061.9 on Nov. 2, 2020 (11 pages).

Tarasov, L. V., Laser Physics, Translated from Russion by Ram S. Wadhwa, MIR publishers, Moscow, pp. 178-181, Chapter 2, 1983.

Tarijian, et al., "Fractional abalative laser skin resurfacing: A review", Journal of Cosmetic and Laser Therapy, 13:262-264, ISSN 1476/4172. Informa UK Ltd. Sep. 2011, 3 pages.

Taylor, C.R. et al., "Treatment of tattoos by Q-switched ruby laser," Arch. Dermatol. vol. 126, pp. 893-899, Jul. 1990.

Togatov, V.V. et al., "Electronic discharge module for pump systems of solid-state lasers", Optical Journal, V. 67, n. 4, pp. 92-96 (2000).

Tuchin, V.V., "Laser light scattering in biomedical diagnostics and therapy," Journal of Laser Applications, vol. 5, No. 2-3, pp. 43-60, 1993.

Unger, W.P., Laser hair transplantation III: Computer-assisted laser transplanting. Dermatol Surg. 1995;21:1047-1055.

Van Bruegel, "Power Density and Exposure Time of He—Ne Irradiation Are More Important Than Total Energy Dose in Photo-Biomodulation of Human Fibroblasts in Vitro," Lasers in Surgery and Medicine, vol. 12 pp. 528-537, 1992.

Vasily, et al., "Non-Ablative Fractional Resurfacing of Surgical and Post-Traumatic Scars", Journal of Drugs in Dermatology, 8(11):998-1005, Nov. 2009, 8 pages.

Volker et al., "Passive mode-locking of an Alexandrite laser for picosecond pulse generation", Journal of Applied Physics, American Institute of Physics, US, 69:6, Mar. 15, 1991 (8 pages).

Walsh, "Laser "Curettage": a Critical Analysis," Periodontology 14:4-12, 1993.

Walsh, "The Current Status of Low Level Laser Therapy in Dentistry. Part 1. Soft Tissue Applications," Aust. Dent. J. Aug. 1997;42(4):247-54.

Watanabe, S. et al., "Comparative studies of femtosecond to microsecond laser pulses on selective pigmented cell injury in skin," Photochemistry and Photobiology, vol. 53, No. 6, pp. 757-762, 1991.

Watanabe, S. et al., "The Effect of Pulse Duration on Selective Pigmented Cell Injury by Dye Lasers," The Journal of Investigative Dermatology, 88:523, 1987.

Watson, G. M., MS, "Minimally Invasive Therapies of the Prostate," Minimally Invasive Therapy, 1:231-240 (1992).

Wei Tech Ang et al., "Design of All-Accelerometer Inertial Measurement Unit for Tremor Sensing in Hand-Held Microsurgical Instrument," 2003 IEEE International Conference on Robotics and Automation (vol. 2), Taipei, Taiwan, Sep. 14-19, 2003.

Wei Tech Ang et al., "Kalman Filtering for Real-Time Orientation Tracking of Handheld Microsurgical Instrument," 2004 IEEE/RSJ International Conference on Intelligent Robots and Systems (IROS), Sendai, Japan, Sep. 28-Oct. 2, 2004.

Welch, A.J. et al., "Evaluation of cooling techniques for the protection of the epidermis during HD-yag laser iradiation of the skin," Neodymium-Yag Laser in Medicine and Surgery, Elsevier Science Publishing Co., publisher, pp. 195-204, 1983.

Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.

Wilson, S.W., "Passive Alignment of a Semiconductor Laser to an Optical Fiber," Universirty of Maryland, Master's Thesis (1995).

Winters, B.H. et al., "Photochemical Products in Coumarin Laser Dyes," Appl. Phys. Lett. 25:723-724 (1974).

Yang et al., "Hybrid optoelectronics: A polymer laser pumped by a nitride light emitting diode," Applied Physics Letters 92, Jan. 23, 2008.

Yules, R.B. et al., "The effect of Q-switched ruby laser radiation on dermal tattoo pigment in man," Arch Surg, vol. 95, pp. 179-180, Aug. 1967.

Zapka et al. "Pulse Slicing and Pockels Cell Shutters," J. Phys. E: Sci, Instrum., vol. 15 (1982).

Zayhowski, J.J. et al., "Gain-switched pulsed operation of microchip lasers", Optice Letters, Optical Society of America, US 14:23, Dec. 1, 1989, pp. 1318-1320.

Zeitler, E. et al., "Laser Characteristics that Might be Useful in Biology," Laser Applications in Medicine and Biology, vol. I, M.L. Wolbarsht, editor, Plenum Press, publishers, Chapter 1, pp. 1-18, 1971.

Zonios et al., "Skin Melanin, Hemoglobin, and Light Scattering Properties can be Quantitatively Assessed in Vivo Using Diffuse Reflectance Spectroscopy," Journal of Investigative Dermatology, 117:1452-1457 (Dec. 2001).

\* cited by examiner

PICOSECOND OPTICAL RADIATION SYSTEMS AND METHODS OF USE

CROSS-REFERENCE TO RELATED APPLICATION

This application is a continuation of U.S. patent application Ser. No. 17/013,082 filed on Sep. 4, 2020, which is a continuation of U.S. patent application Ser. No. 16/363,655, filed on Mar. 25, 2019, now U.S. Pat. No. 10,765,478, which is a continuation of Ser. No. 14/340,961, filed on Jul. 25, 2014, now U.S. Pat. No. 10,245,107, which is a continuation of U.S. patent application Ser. No. 14/216,353, filed on Mar. 17, 2014, now U.S. Pat. No. 10,285,757, which claims priority to and the benefit of U.S. Provisional Application No. 61/789,144 filed on Mar. 15, 2013 entitled Subnanosecond Laser Systems and Methods of Use and U.S. Provisional Application No. 61/891,299 filed on Oct. 15, 2013 entitled Multi-Wavelength Optical Radiation Sources for Dermatology, the entire contents of which are incorporated by reference herein.

FIELD

The present disclosure relates generally to dermatological systems, methods, and devices and, in particular, to systems, methods, and devices for applying optical radiation, e.g. laser radiation in the visible and near infrared wavelengths, to treat tattoos, and other pigmentation disorders.

BACKGROUND

The use of lasers, as controllable sources of relatively monochromatic and coherent radiation, is becoming increasingly common in diverse fields such as telecommunications, data storage and retrieval, entertainment, research, and many others. In the area of medicine, for example, lasers have proven useful in surgical and cosmetic procedures in which a precise beam of high energy radiation can cause localized effects through photothermal processes (e.g., selective photothermolysis) and/or photomechanical processes (e.g., induction of cavitation bubbles and acoustic shock waves). In dermatology specifically, lasers have been used in a wide variety of procedures including hair removal, skin resurfacing, removal of unwanted veins, and the clearance of both naturally-occurring and artificial skin pigmentations (e.g., birthmarks, port wine stains, and tattoos).

Whereas early laser tattoo removal procedures often utilized non-selective ablation of tissue at the tattoo site with water serving as the target chromophore, recent procedures have instead utilized Q-switched lasers capable of producing high-powered, nanosecond pulses to induce photomechanical breakdown of the tattoo particles themselves. In addition to pulse duration and power, the wavelength of the radiation is also an important parameter in the efficacy of a treatment. For example, though alexandrite lasers emitting picosecond pulses at wavelengths between 750 and 760 nm have been found to be especially effective at treating black, blue, and green tattoo pigments (iBrauer et al., "Successful and Rapid Treatment of Blue and Green Tattoo Pigment With a Novel Picosecond Laser," *Archives of Dermatology*, 148(7):820-823 (2012)), radiation in the 750-760 nm range is not nearly as effective in removing red or orange tattoos due to the low absorption coefficient of orange and red tattoo pigments at such wavelengths.

Accordingly, there exists a need for improved methods and apparatus for producing ultra-short pulses of laser radiation at various wavelengths for the treatment of tattoos, pigmented lesions, and other skin disorders.

SUMMARY

Systems, methods, and devices for generating and delivering ultra-short pulses, e.g., picosecond pulses, of laser radiation at multiple wavelengths with low energy losses are provided herein. It has been found, for example, that the picosecond, high power pulses disclosed herein can be particularly effective in removing skin pigmentations, in part, because the pulses induce mechanical waves (e.g., shock waves and pressure waves) at the target sites that cause greater disruption and better clearance of pigment particles. In accordance with various aspects of the present teachings, the wavelength of the applied pulses can be selected to match the absorption spectrum of previously difficult-to-treat pigments (while nonetheless maintaining the ultra-short pulse durations) such that the naturally-occurring and artificial skin pigments can be cleared with a reduced number of treatments relative to known procedures, thereby providing a system that could satisfy a long-felt need in the art. By way of example, the methods and systems disclosed herein can improve the disruption and clearing efficacy of red and orange tattoos by delivering laser pulses having a wavelength between about 400 and about 550 nm, where these pigments exhibit much higher absorption coefficients.

In accordance with various aspects, certain embodiments of the applicants' teachings relate to an apparatus for delivery of pulsed treatment radiation. The apparatus can comprise a pump radiation source generating picosecond pulses at a first wavelength, and a wavelength-shifting resonator having a lasing medium and resonant cavity configured to receive the picosecond pulses from the pump radiation source at the first wavelength and to emit radiation at a second wavelength in response thereto. The resonant cavity of the wavelength-shifting resonator has a round trip time shorter than the duration of the picosecond pulses generated by the pump radiation source, and in some aspects, the wavelength-shifting resonator can have a round trip time at least 5 times shorter than the duration of the picosecond pulses generated by the pump radiation source (e.g., at least 10 times shorter).

In accordance with various aspects of the present teachings, the wavelength-shifting resonator can have a variety of configurations to produce the wavelength-shifted picosecond pulses provided herein. By way of example, the wavelength-shifting resonator can have a cavity length that is from about 0.1 millimeters to about 150 millimeters, or from about 60 millimeters to about 120 millimeters, or from about 80 millimeters to about 100 millimeters. However, in one example, the wavelength-shifting resonator can have a cavity length less than 10 millimeters (e.g., a cavity length between 0.1 and 10 millimeters). In various aspects, for example, the wavelength-shifting resonator has a cavity length between 1 and 8 millimeters. By way of non-limiting example, the resonator can comprise a neodymium-doped vanadate crystal ($Nd:YVO_4$) crystal having a length between the input side and the output side of about 3 mm or a neodymium-doped yttrium-aluminum garnet crystal (Nd:YAG) having a length between the input side and output side of less than about 8 mm (e.g., about 6 mm).

As indicated above, the lasing medium can comprise a variety of materials for receiving the pump pulse from the pump radiation source. By way of example, the lasing medium of the wavelength-shifting resonator can comprise a neodymium-doped crystal, including, a solid state crystal medium selected from the group of neodymium-doped yttrium-aluminum garnet (Nd:YAG) crystals, neodymium-doped pervoskite (Nd:YAP or Nd:YAlO$_3$) crystals, neodymium-doped yttrium-lithium-fluoride (Nd:YAF) crystals, and neodymium-doped, vanadate (Nd:YVO$_4$) crystals. Moreover, in some aspects, the lasing medium can comprise between about 1 and about 3 percent neodymium.

In various aspects, the apparatus can produce polarized optical radiation. For example, the apparatus can comprise a polarizer configured to polarize optical radiation emitted by the wavelength-shifting resonator. Additionally or alternatively, the apparatus can comprise a polarizer embedded within the resonant cavity of the wavelength-shifting resonator. Additionally or alternatively, the lasing medium of the wavelength-shifting resonator can be a substantially polarizing medium.

In some aspects, the apparatus can further comprise a frequency-doubling waveguide. By way of example, the frequency-doubling waveguide can comprise a second harmonic generating, nonlinear crystal material that can receive the radiation emitted by the wavelength-shifting resonator to output a pulse having twice the frequency of the input pulse (i.e., half the wavelength). In various aspects, the frequency-doubling waveguide can comprise a lithium triborate (LiB$_3$O$_5$) material. In a related aspect, an amplifier can be disposed between the wavelength-shifting resonator and the frequency-doubling waveguide.

The pump radiation source can in various embodiments have a variety of configurations. By way of example, the pump radiation source can be a mode-locked laser, that in some embodiments can comprise a resonator, a lasing medium, a Pockels cell and a controller, wherein the controller generates a mode-locked pulse by applying a periodic voltage waveform to the Pockels cell. In some aspects, the mode-locked laser can comprise an alexandrite laser configured to produce pulsed laser energy at about 755 nm having at least about 100 mJ/pulse (e.g., from about 200 to about 800 mJ/pulse). In various aspects, the mode-locked laser can generate pulsed laser energy having a pulse duration of less than 1000 picoseconds (e.g., about 860 picoseconds).

In accordance with various aspects of the present teachings, the apparatus can further comprise a treatment beam delivery system configured to apply a treatment beam to a patient's skin. In some aspects, the treatment beam can comprise at least one of picosecond pulses from the pump radiation source at the first wavelength, picosecond pulses emitted by the wavelength-shifting resonator at the second wavelength, and picosecond pulses at a third wavelength, wherein the picosecond pulses at the third wavelength are output by a frequency-doubling waveguide that receives the picosecond pulses at the second wavelength. In various embodiments, the first wavelength can be about 755 nm, the second wavelength can be about 1064 nm, and the third wavelength can be about 532 nm. Additionally, the apparatus can be operated so as to enable the selection of the wavelength of the pulse(s) to be applied to a patient's skin through the treatment beam delivery system. The apparatus can also control the wavelength-shifting resonator temperature.

In accordance with various aspects, certain embodiments of the applicants' teachings relate to a method for shifting the wavelength of a picosecond optical radiation pulse. The method can comprise generating a pulse of optical radiation at a first wavelength and having a duration less than 1000 picoseconds, pumping a wavelength-shifting resonator with the pulse of optical radiation at the first wavelength, the wavelength-shifting resonator comprising a laser crystal with a high absorption coefficient at the first wavelength, and extracting a pulse of radiation at a second wavelength emitted by the wavelength-shifting resonator, wherein the pulse at the second wavelength also has a duration of less than 1000 picoseconds. The round trip time of the wavelength-shifting resonator is shorter than the pumping laser pulse duration. For example, the wavelength-shifting resonator can have a round trip time at least 10 times shorter than the duration of the pumping pulse.

In various aspects, the method can further comprise one or more of polarizing, amplifying, and frequency-doubling the output of the wavelength-shifting resonator. For example, in some aspects, a polarizer can be configured to polarize optical radiation emitted by the wavelength-shifting resonator. Additionally or alternatively, a polarizer can be embedded within the resonant cavity of the wavelength-shifting resonator or the lasing medium of the wavelength-shifting resonator can be a substantially polarizing medium. In some aspects, the pulse of radiation at a second wavelength can be transmitted to a frequency doubling crystal so as to generate a pulse having twice the frequency of the input pulse (i.e., half the wavelength).

In accordance with various aspects, certain embodiments of the applicants' teachings relate to a method for treating tattoos or skin pigmentation disorder using a picosecond optical radiation source. The method can comprise employing a pump radiation source to generate a pulse of optical radiation at a first wavelength, wherein the pulse has a duration of less than 1000 picoseconds, and pumping a wavelength-shifting resonator with the pulse of optical radiation at the first wavelength, the wavelength-shifting resonator comprising a laser crystal with high absorption coefficient at the first wavelength, and extracting a pulse of radiation at a second wavelength emitted by the wavelength-shifting resonator, wherein the pulse at the second wavelength also has a duration of less than 1000 picoseconds. In accordance with the present teachings, the round trip time of the wavelength-shifting resonator can be shorter than the pumping laser pulse duration. The method can further comprise delivering the pulse of radiation at the second wavelength to a frequency-doubling waveguide so as to generate a pulse of radiation at a third wavelength, wherein the pulse at the third wavelength also has a duration of less than 1000 picoseconds, and directing the pulse at the third wavelength to a tattoo pigment or a skin pigmentation target to disrupt the target and promote clearance thereof. By way of example, the first wavelength can be about 755 nm, the second wavelength can be about 1064 nm, and the third wavelength can be about 532 nm, and the method can comprise selecting the wavelength of the pulse(s) to be applied to a patient's skin.

In accordance with various aspects, certain embodiments of the applicants' teachings relate to a method for removing a tattoo or treating a skin pigmentation disorder. The method comprises applying pulses having a duration less than 1000 picoseconds to an area of a patient's skin comprising a tattoo pigment or skin pigmentation so as to generate photomechanical disruption of the tattoo pigment or skin pigmentation, wherein the pulses have a wavelength in a range of about 400 nm to about 550 nm (e.g., about 532 nm). In some aspects, the method further comprises utilizing a Nd:YVO$_4$ lasing medium to generate picosecond pulses of radiation having a wavelength of about 1064 nm, and frequency doubling the picosecond pulses having a wavelength of about 1064 nm to generate picosecond pulses having a wavelength of about 532 nm.

In one aspect, the disclosure relates to an apparatus for delivery of a pulsed treatment radiation such as a laser. The laser having a light source, a resonator having a mode lock element, and a lasing medium such as an active lasing medium. The lasing medium is impinged upon by the light source. An element is disposed between the light source and the lasing medium, the element enables a substantially uniform gain across the lasing medium. The laser can include a second light source. The first light source and/or the second light source can be a pumped radiation source such a flash lamp. In one embodiment, the lasing medium is an alexandrite crystal. The element can be, for example, an alumina rod having a diameter of about 0.063 inches. The element can be at least one of a deflector, a scattering element, a refractor, a reflector, an absorber, and a baffle. In one embodiment, element is equidistant from the flash lamp and the lasing media. In another embodiment, the element is disposed on the lasing medium, is disposed on the light source, or is disposed on both the lasing medium and the light source.

In another aspect, the disclosure relates to an apparatus for delivery of a pulsed treatment radiation such as a laser. The laser includes a light source and a resonator having a multimode output, a mode lock element and an astigmatic element disposed inside the resonator. The astigmatic element can prevent free space propagation modes such as Hermites within the multimode output from coupling together. In this way, beam uniformity is improved with the use of the astigmatic element compared to where the astigmatic element is absent. Suitable astigmatic elements can include, for example, at least one of a cylindrical lens, an angled spherical lens, and a prism (e.g., an anamorphic prism).

In another aspect, the disclosure relates to a resonator (e.g., an oscillator) for a mode locked laser having a fundamental frequency which is the speed of light divided by the round trip optical path length (2 L) of the resonator and a mode locking element (e.g., a Pockels cell) that is modulated at a frequency that is less than the fundamental frequency. The frequency can be a sub-harmonic (1/n) of the speed of light (c) divided by the round trip optical path length (2 L) where (n) is whole number greater than 1. The resonator can be employed in an apparatus for delivery of a pulsed treatment radiation, such as a laser, to treat tissue.

In another aspect, the disclosure relates to a resonator (e.g., an oscillator) for a mode locked laser that provides a frequency corresponding to a fundamental round trip optical path length (2 L) in a mode locked resonator and selecting a sub-harmonic optical path length that is shortened by dividing the fundamental round trip optical path length (2 L) by a sub-harmonic factor (n), which is a whole number greater than 1, and the sub-harmonic total path length has n round trip optical path lengths. The resonator can be employed in a laser to treat tissue.

These and other features of the applicants' teachings are set forth herein.

BRIEF DESCRIPTION OF THE DRAWINGS

The skilled person in the art will understand that the drawings, described below, are for illustration purposes only. The drawings are not intended to limit the scope of the applicants' teachings in any way.

DETAILED DESCRIPTION

Figure 1:
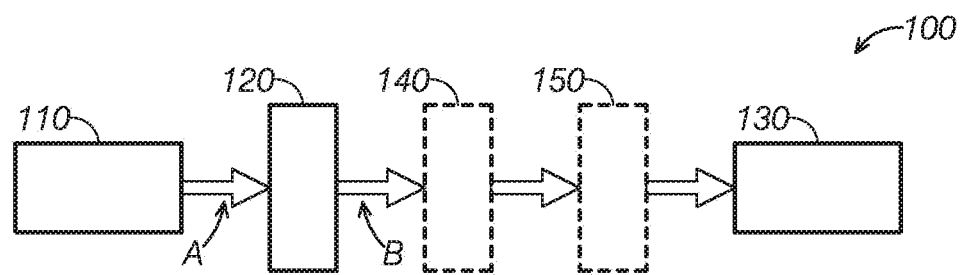
FIG. 1, in a schematic diagram, illustrates an exemplary system having a wavelength-shifting resonator for generating picosecond pulses in accordance with various aspects of the applicants' teachings.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques which would be apparent to one of skill in the art. In addition, in order to more clearly and concisely describe the claimed subject matter, the following definitions are provided for certain terms which are used in the specification and appended claims.

The terms "picosecond" or "picosecond pulse," as used herein, is intended to encompass pulses of optical radiation having durations ranging from 0.1 picoseconds to 1000 picoseconds, preferably less than 1000 picoseconds. e.g., less than 900 picoseconds, less than 800 picoseconds or less than 700 picoseconds. For non-square pulses, pulse durations are typically measured by the full width at half maximum (FWHM) technique.

As used herein, the recitation of a numerical range for a variable is intended to convey that the embodiments may be practiced using any of the values within that range, including the bounds of the range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values ≥0 and ≤2 if the variable is inherently continuous. Finally, the variable can take multiple values in the range, including any sub-range of values within the cited range.

As used herein, unless specifically indicated otherwise, the word "or" is used in the inclusive sense of "and/or" and not the exclusive sense of "either/or."

In accordance with various aspects of the applicants' teachings, the systems and methods described herein can be effective to deliver picosecond pulses of laser radiation for the treatment of naturally-occurring and artificial skin pigmentations utilizing wavelengths that match the pigmentations' absorption spectrum. The picosecond, high power pulses disclosed herein can be particularly effective in removing these previously-difficult to treat skin pigmentations, in part, because the pulses induce photomechanical shock waves at the target sites that cause greater disruption and better clearance of pigment particles. By way of example, the methods and systems disclosed herein can improve the clearing of red and orange tattoos with a reduced number of treatments by delivering picosecond laser pulses having a wavelength between 400 and 550 nm, where these pigments exhibit much higher absorption coefficients. Moreover, applicants have discovered that various embodiments of the wavelength-shifting resonators described herein can surprisingly generate particularly efficacious pulses exhibiting picosecond pulsewidths shorter than the input pumping pulses, with low energy losses and/or minimal pulse-shaping (e.g., without use of a modelocker, Q-switch, pulse picker or any similar device of active or passive type).

The present disclosure relates to laser systems having sub-nanosecond pulsing (e.g., picosecond pulsing). Exemplary systems are described in our U.S. Pat. Nos. 7,929,579 and 7,586,957, both incorporated herein by reference. These patents disclose picosecond laser apparatuses and methods for their operation and use. Herein we describe certain improvements to such systems.

With reference now to FIG. 1, an exemplary system 100 for the generation and delivery of picosecond-pulsed treatment radiation is schematically depicted. As shown in FIG. 1, the system generally includes a pump radiation source 110 for generating picosecond pulses at a first wavelength, a wavelength-shifting resonator 120 for receiving the picosecond pulses generated by the pump radiation source and emitting radiation at a second wavelength in response thereto, and a treatment beam delivery system 130 for delivering a pulsed treatment beam to the patient's skin.

The pump radiation source 110 generally generates one or more pulses at a first wavelength to be transmitted to the wavelength-shifting resonator 120, and can have a variety of configurations. For example, the pulses generated by the pump radiation source 110 can have a variety of wavelengths, pulse durations, and energies. In some aspects, as will be discussed in detail below, the pump radiation source 110 can be selected to emit substantially monochromatic optical radiation having a wavelength that can be efficiently absorbed by the wavelength-shifting resonator 120 in a minimum number of passes through the gain medium. Additionally, it will be appreciated by a person skilled in the art in light of the present teachings that the pump radiation source 110 can be operated so as to generate pulses at various energies, depending for example, on the amount of energy required to stimulate emission by the wavelength-shifting resonator 120 and the amount of energy required to perform a particular treatment in light of the efficiency of the system 100 as a whole.

In various aspects, the pump radiation source 110 can be configured to generate picosecond pulses of optical radiation. That is, the pump radiation source can generate pulsed radiation exhibiting a pulse duration less than about 1000 picoseconds (e.g., within a range of about 500 picoseconds to about 800 picoseconds). In an exemplary embodiment, the pump radiation source 110 for generating the pump pulse at a first wavelength can include a resonator (or laser cavity containing a lasing medium), an electro-optical device (e.g., a Pockels cell), and a polarizer (e.g., a thin-film polarizer), as described for example with reference to FIG. 2 of U.S. Pat. No. 7,586,957, issued on Sep. 8, 2009 and entitled "Picosecond Laser Apparatus and Methods for Its Operation and Use." the contents of which are hereby incorporated by reference in its entirety.

In an exemplary embodiment, the lasing or gain medium of the pump radiation source 110 can be pumped by any conventional pumping device such as an optical pumping device (e.g., a flash lamp) or an electrical or injection pumping device. In an exemplary embodiment, the pump radiation source 110 comprises a solid state lasing medium and an optical pumping device. Exemplary solid state lasers include an alexandrite or a titanium doped sapphire (TIS) crystal, Nd:YAG lasers, Nd:YAP, Nd:YAlO$_3$ lasers, Nd:YAF lasers, and other rare earth and transition metal ion dopants (e.g., erbium, chromium, and titanium) and other crystal and glass media hosts (e.g., vanadate crystals such as YVO$_4$, fluoride glasses such as ZBLN, silica glasses, and other minerals such as ruby). At opposite ends of the optical axis of the resonator can be first and second mirrors having substantially complete reflectivity and/or being substantially totally reflective such that a laser pulse traveling from the lasing medium towards second mirror will first pass through the polarizer, then the Pockels cell, reflect at second mirror, traverse Pockels cell a second time, and finally pass through polarizer a second time before returning to the gain medium.

The terms "substantially complete reflectivity" and/or "substantially totally reflective" are used to indicate that the mirrors completely reflect incident laser radiation of the type normally present during operation of the resonator, or reflect at least 90%, preferably at least 95%, and more preferably at least 99% of incident radiation.

Depending upon the bias voltage applied to the Pockels cell, some portion (or rejected fraction) of the energy in the pulse will be rejected at the polarizer and exit the resonator along an output path to be transmitted to the wavelength-shifting resonator 120. Once the laser energy, oscillating in the resonator of the pump radiation source 110 under amplification conditions, has reached a desired or maximum amplitude, it can thereafter be extracted for transmission to the wavelength-shifting resonator 120 by changing the bias voltage to the Pockels cell such that the effective reflectivity of the second mirror is selected to output laser radiation having the desired pulse duration and energy output.

The wavelength-shifting resonator 120 can also have a variety of configurations in accordance with the applicant's present teachings, but is generally configured to receive the pulses generated by the pump radiation source 110 and emit radiation at a second wavelength in response thereto. In an exemplary embodiment, the wavelength-shifting resonator 120 comprises a lasing medium and a resonant cavity extending between an input end and an output end, wherein the lasing medium absorbs the pulses of optical energy received from the pump radiation source 110 and, through a process of stimulated emission, emits one or more pulses of optical laser radiation exhibiting a second wavelength. As will be appreciated by a person skilled in the art in light of the present teachings, the lasing medium of the wavelength-shifting resonator can comprise a neodymium-doped crystal, including by way of non-limiting example solid state crystals of neodymium-doped yttrium-aluminum garnet (Nd:YAG), neodymium-doped pervoskite (Nd:YAP or Nd:YAlO$_3$), neodymium-doped yttrium-lithium-fluoride (Nd:YAF), and neodymium-doped vanadate (Nd:YVO$_4$ crystals. It will also be appreciated that other rare earth transition metal dopants (and in combination with other crystals and glass media hosts) can be used as the lasing medium in the wavelength-shifting resonator. Moreover, it will be appreciated that the solid state laser medium can be doped with various concentrations of the dopant so as to increase the absorption of the pump pulse within the lasing medium. By way of example, in some aspects the lasing medium can comprise between about 1 and about 3 percent neodymium.

The lasing medium of the wavelength-shifting resonator 120 can also have a variety of shapes (e.g., rods, slabs, cubes) but is generally long enough along the optical axis such that the lasing medium absorbs a substantial portion (e.g., most, greater than 80%, greater than 90%) of the pump pulse in two passes through the crystal. As such, it will be appreciated by a person skilled in the art that the wavelength of the pump pulse generated by the pump radiation source 110 and the absorption spectrum of the lasing medium of the resonator 120 can be matched to improve absorption. However, whereas prior art techniques tend to focus on maximizing absorption of the pump pulse by increasing crystal length, the resonator cavities disclosed can instead utilize a short crystal length such that the roundtrip time of optical radiation in the resonant cavity (i.e., $t_{roundtrip} = 2\, L_{resonator}/C$, where $L_{resonator}$ is the optical path length of the resonator (the optical path length can account for differences due to the photons traveling through the lasing medium and/or the air in other parts of the path) and c is the speed of light) in some embodiments the optical path length is substantially less than the pulse duration of the input pulse (i.e., less than the pulse duration of the pulses generated by the pump radiation source 110). For example, in some aspects, the roundtrip time can be less than 5 times shorter than the duration of the picosecond pump pulses input into the resonant cavity (e.g., less than 10 times shorter). Without being bound by any particular theory, it is believed that by shortening the resonant cavity, the output pulse extracted from the resonant cavity can have an ultra-short duration without the need for additional pulse-shaping (e.g., without use of a modelocker, Q-switch, pulse picker or any similar device of active or passive type). For example, the pulses generated by the wavelength-shifting resonator can have a pulse duration less than 1000 picoseconds (e.g., about 500 picoseconds, about 750 picoseconds).

After the picosecond laser pulses are extracted from the wavelength-shifting resonator 120, they can be transmitted directly to the treatment beam delivery system 130 for application to the patient's skin, for example, or they can be further processed through one or more optional optical elements shown in phantom, such as an amplifier 140, frequency doubling waveguide 150, and/or filter (not shown). As will be appreciated by a person skilled in the art, any number of known downstream optical (e.g., lenses) electro-optical and/or acousto-optic elements modified in accordance with the present teachings can be used to focus, shape, and/or alter (e.g., amplify) the pulsed beam for ultimate delivery to the patient's skin to ensure a sufficient laser output, while nonetheless maintaining the ultrashort pulse duration generated in the wavelength-shifting resonator 120.

Figure 2:
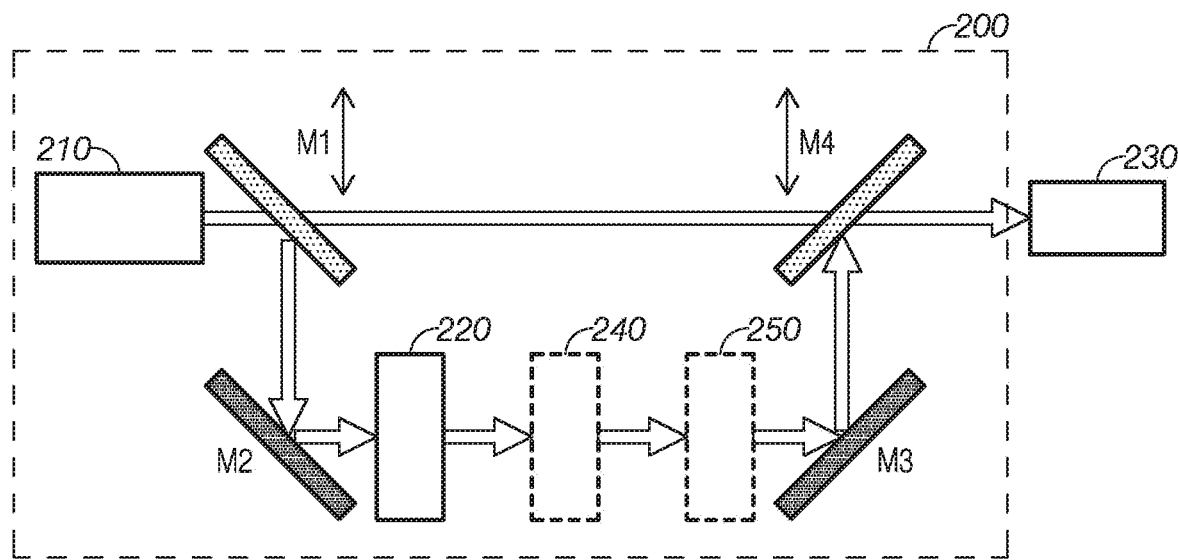
FIG. 2, in a schematic diagram, illustrates an exemplary system having a wavelength-shifting resonator, the system for generating multiple wavelengths of picosecond pulses in accordance with various aspects of the applicants' teachings.

With reference now to FIG. 2, an exemplary system 200 is depicted that includes a wavelength-shifting resonator 220 as described for example in FIG. 1. As shown in FIG. 2, however, the system 200 can also be used to generate and selectively apply multiple wavelengths of picosecond pulses depending, for example, on the absorption spectrum of the target pigment or tissue. As shown in FIG. 2, the exemplary system generally includes a pump radiation source 210 for generating picosecond pulses at a first wavelength (e.g., an alexandrite source emitting 755 nm pulses having a duration less than 1000 picoseconds), at least one optical element (M1 and/or M2) configured to selectively divert the picosecond pulses at the first wavelength to a wavelength-shifting resonator 220 (e.g., a 1064 nm oscillator configured to receive the pump pulses and generate 1064 nm picosecond pulses of radiation in response thereto), at least one optical element (M3 and/or M4) and a treatment beam delivery system 230 that can deliver the picosecond pulses of one or more wavelengths to the treatment target. As shown in phantom, and discussed otherwise herein, the system 200 can additionally include, for example, an amplifier 240 and a second harmonic generator 250 (e.g., a lithium triborate (LBO) or potassium trianyl phosphate (KTP) frequency doubling crystal).

As discussed above, the wavelength-shifting resonator 220 can comprise a rare earth doped laser gain crystal. In some aspects, rare earth doped laser crystals that generate a polarized laser beam like Nd:YVO$_4$ can be used to eliminate the need for an additional polarizing element. Crystals like Nd:YAG or Nd doped glasses can be used with an additional polarizing element in the resonator. In the exemplary embodiment, the input side of the Nd:YVO$_4$ crystal can be AR coated for the alexandrite wavelength and HR coated for 1064 nm, while the output side of the crystal can be IR coated for the alexandrite wavelength and can exhibit approximately 20 to 70% reflectivity at 1064 nm. In an exemplary embodiment, the Nd:YVO$_4$ crystal length can be selected such that it absorbs most (greater than 90%) of the alexandrite laser pulse in the two passes through the crystal. For example, with neodymium doping in the range 1 to 3%, the Nd:YVO$_4$ crystal can be chosen to be around 3 mm long (with no other optical elements in the resonator, the resonator length is substantially equal to the crystal length of 3 mm). That means the resonator round-trip time is around 39 ps—substantially less than the pulse duration of the alexandrite pumping pulse (around 500 to 800 ps). The 1064 nm pulse generated in the very short round trip time Nd:YVO$_4$ resonator may be slightly longer than the pumping alexandrite pulse and shorter than 1000 ps. The quantum defect will account for a 30% pulse energy loss and another 15% of the energy is likely to be lost due to coatings, crystal and geometry imperfection, for an overall energy conversion efficiency of around 50 to 60% such that 100 mJ pulse energy can be produced at 1064 nm, by way of non-limiting example. In the Second Harmonic Generator 250 the second harmonic conversion in the frequency-doubling crystal is around 50%, such that a 50 mJ pulse energy can therefore be produced at 532 nm. Given the high absorption at 532 nm of red and/or orange tattoo pigments, a 50 mJ, 532 nm pulse with a pulse duration less than 1000 picoseconds can be effective at disrupting, and eventually clearing, red and/or orange tattoo granules.

Figure 3:
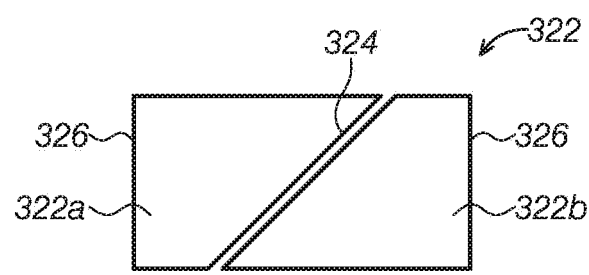
FIG. 3, in a schematic diagram, illustrates an exemplary wavelength-shifting resonator having an embedded polarizer for use in the systems of FIGS. 1 and 2 in accordance with various aspects of the applicants' teachings.

Though the above described example utilized an Nd:YVO$_4$ crystal in the wavelength-shifting resonator 220 (and without the need for a polarizing element), Nd:YAG crystals or other Nd-doped glasses can alternatively be used as the short resonator to generate the picosecond pulses in response to stimulation from the pump radiation source. In such embodiments, a polarizing element as known in the art can be utilized external to the wavelength-shifting resonator or can be embedded therein. As shown in FIG. 3, for example, a short Nd:YAG resonator 322 can consist of two identically shaped crystals 322a,b with one face 324 cut at an angle that is AR coated for the alexandrite wavelength and polarized-coated for the stimulated emission wavelength (e.g., 1064 nm and high p transmission). The flat faces 326 of the two Nd:YAG crystals can have different coatings-one is AR coated at 755 nm and HR coated at 1064 nm and the other is HR coated for 755 nm and has an output coupler reflectivity around 50 to 80% for 1064 nm. The higher output coupler reflectivity for the Nd:YAG crystal compared to the Nd:YVO$_4$ crystal is due to the lower gain cross-section in Nd:YAG.

With reference again to FIG. 2, it will be appreciated in light of the present teachings that utilizing a wavelength-shifting resonator 220 to generate picosecond pulses depends on the pulse duration of the pumping pulse (e.g., shorter pumping pulses will lead to shorter generated pulses at 1064 nm) and the roundtrip time determined by the length of the resonator cavity (e.g., shorter crystals lead to shorter roundtrip time, however the crystal has to be sufficiently long to absorb greater than 90% of the alexandrite energy). For example, an 8 mm long Nd:YAG resonator would have a 97 ps round trip time. Though such a roundtrip time is longer than the roundtrip time that can be achieved with a Nd:YVO$_4$, resonator, it remains much shorter than the pumping Alexandrite laser pulse duration. It will be appreciated by a person skilled in the art in light of the present teaching that one possible way to shorten the crystal length is to tune the alexandrite laser in the range 750 to 760 nm for maximum absorption in the Nd doped crystal and use the minimum possible crystal length. In addition, by tuning the alexandrite laser in the range of 750 to 757 nm allows for the alexandrite wavelength to be set to avoid the excited state absorption bands in the Nd ion as described by Kliewer and Powell, IEEE Journal of Quantum Electronics vol. 25, page 1850-1854 (1989).

With reference again to FIG. 2, the laser beam emitted by the pump radiation source 210 (e.g., an alexandrite laser source generating pulses at around 755 nm and 200 mJ/pulse, with a pulse duration shorter than 800 ps) can be reflected on 100% reflectors M1 and M2 to serve as the pump beam for the wavelength-shifting resonator 220 (e.g., an Nd:YVO$_4$ or Nd:YAG short round trip time 1064 nm oscillator), thereby stimulating the oscillator 220 to produce up to around 100 mJ pulse energy at 1064 nm at less than 1000 ps pulse duration. The output firm the 1064 nm oscillator 220 can be reflected on the 100% reflectors M3 and M4 and can be coupled into the treatment beam delivery system 230.

Alternatively, the output from the 1064 nm oscillator 220 can be amplified in the 1064 nm amplifier 240 to a pulse energy between 200 and 900 mJ, for example, while maintaining the less than 1000 ps pulse duration and then reflected on the 100% reflectors M3 and M4 and coupled into the treatment beam delivery system.

Alternatively or additionally, the output from the 1064 nm oscillator 220 or the output from the 1064 nm amplifier 240 can be converted to second harmonic 532 nm radiation in the Second Harmonic Generator 250. For a typical 50% conversion efficiency in the Second Harmonic Generator 250, the 532 nm pulse output can have a pulse energy around 50 mJ when there is no 1064 nm amplifier, or between 100 to 500 mJ when the 1064 nm pulse is amplified in the 1064 nm amplifier 240 before it reaches the Second Harmonic Generator 250. In both cases, the 532 nm pulse will have a pulse duration of around 750 ps or less due to the pulse shortening effect of the second harmonic conversion process. After being frequency doubled, the 532 nm pulse can propagate in parallel with the 1064 nm pumping pulse. By choosing mirrors M3 and M4 to be 100% reflectors or substantially totally reflective reflectors on both the 1064 nm and 532 nm wavelengths, a combined wavelength treatment can be delivered to the target through the treatment beam delivery system.

Alternatively, in some embodiments, mirrors M3 and M4 can be chosen to be 100% reflectors at 532 nm and 100% transmitters at 1064 nm so as to deliver a single wavelength 532 nm treatment through the treatment beam delivery system. Moreover, by allowing the mirrors (M1, M2) to selectively transmit or deflect the 755 nm alexandrite pulse, for example, by translating the mirrors into and out of the pulse beam, the system 200 can be designed to transmit all three treatment wavelengths 755, 1064 and 532 nm. That is, when mirrors M1 and M4 are moved out of the beam path of the pump radiation source 210, the pulsed pump beam of 755 nm is coupled directly to the treatment beam delivery system to be used for patient treatments.

EXAMPLE

Figure 4:
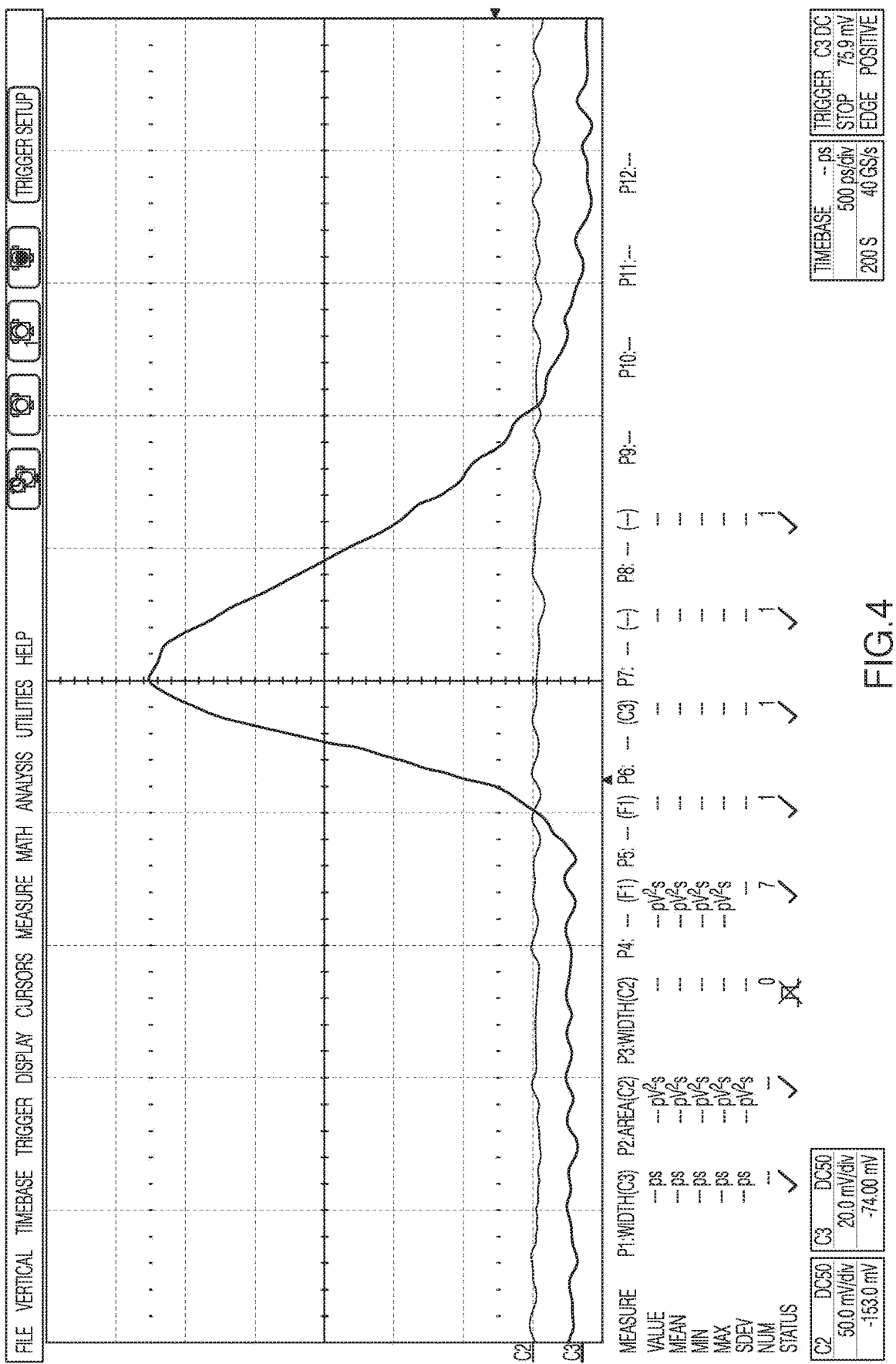
FIG. 4 depicts an exemplary output pulse of an Nd:YAG resonator operated in accordance with various aspects of the applicants' teachings.

An example plot of the output pulse shape of a short wavelength-shifting Nd:YAG resonator with a 70% output coupler is shown in FIG. 4, as measured at position (B) of FIG. 1. The Nd:YAG crystal was doped to 1.3 at. % (30% higher than the standard 1 at. % doping) to allow for a shorter resonator—6.2 mm in length, shorter roundtrip time, and a shorter output pulse duration. The Nd:YAG oscillator was pumped by an Alexandrite laser with 200 mJ per pulse, 680 ps pulse duration, and a 4.4 mm spot (as measured at position (A) of FIG. 1). As shown in FIG. 4, the output of the wavelength-shifting Nd:YAG resonator at 1064 nm was 65 mJ per pulse, 750 ps mean pulse duration. The roundtrip time in the Nd:YAG resonator was about 76 picoseconds, substantially shorter than the 680 ps Alexandrite input pulse.

Figure 5:
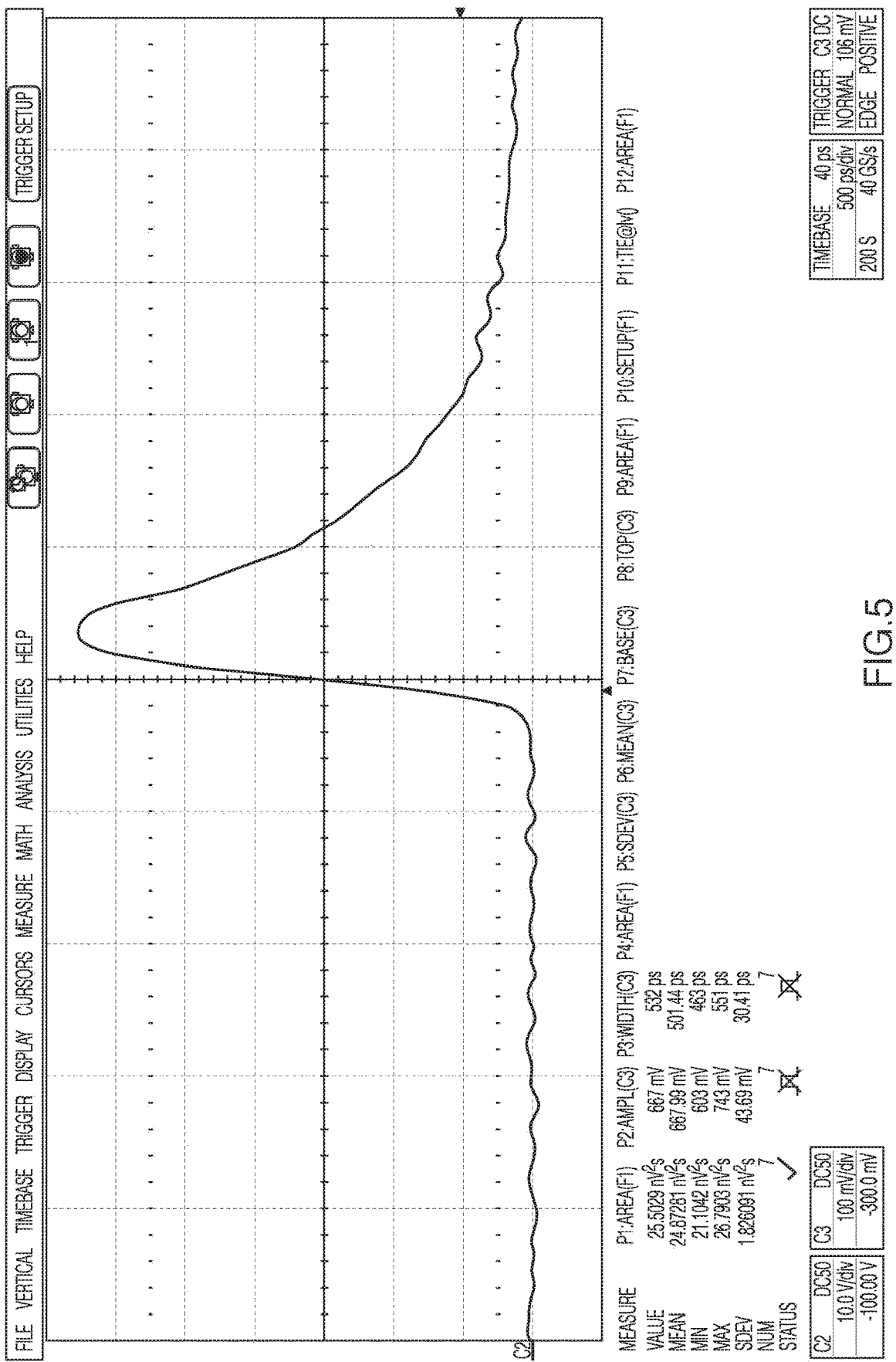
FIG. 5 depicts an exemplary output pulse of an Nd:YVO$_4$ resonator operated in accordance with various aspects of the applicants' teachings.

With reference now to FIG. 5, the output pulse shape of a short resonator Nd:YVO$_4$ laser having a length of 3 mm with a 50% output coupler is depicted, as measured at position (B) of FIG. 1. The Nd:YVO$_4$ oscillator was pumped by the output of an Alexandrite laser delivering 200 mJ per pulse, 720 ps pulse duration focused to a 6.3 mm spot (as measured at position (A) of FIG. 1). The pump spot was apertured down to 3.6 mm diameter. As shown in FIG. 5, the output wavelength-shifting Nd:YVO$_4$ resonator at 1064 nm was 34 mJ per pulse, 500 ps mean pulse duration. It is surprising that the output pulse duration of the short pulse Nd:YVO$_4$ laser resonator is shorter than the pulse duration of the pumping Alexandrite pulse—500 ps relative to 720 ps, especially considering that the shorter output pulse duration is achieved without any extra elements in the laser resonator aimed at pulse shaping (e.g., in the resonator there is no modelocker, Q-switch, pulse picker or any similar device of active or passive type). The short Nd:YVO$_4$ resonator is also remarkably and surprisingly efficient. That is, with 33% of the Alexandrite energy being transmitted through the aperture (i.e., 66 mJ), the 34 mJ Nd:YVO$_4$ resonator output is 51% of the pump energy transmitted thereto. The roundtrip time in the Nd:YVO$_4$ resonator was about 39 ps, substantially shorter than the 720 ps Alexandrite input pulse.

Figure 6:
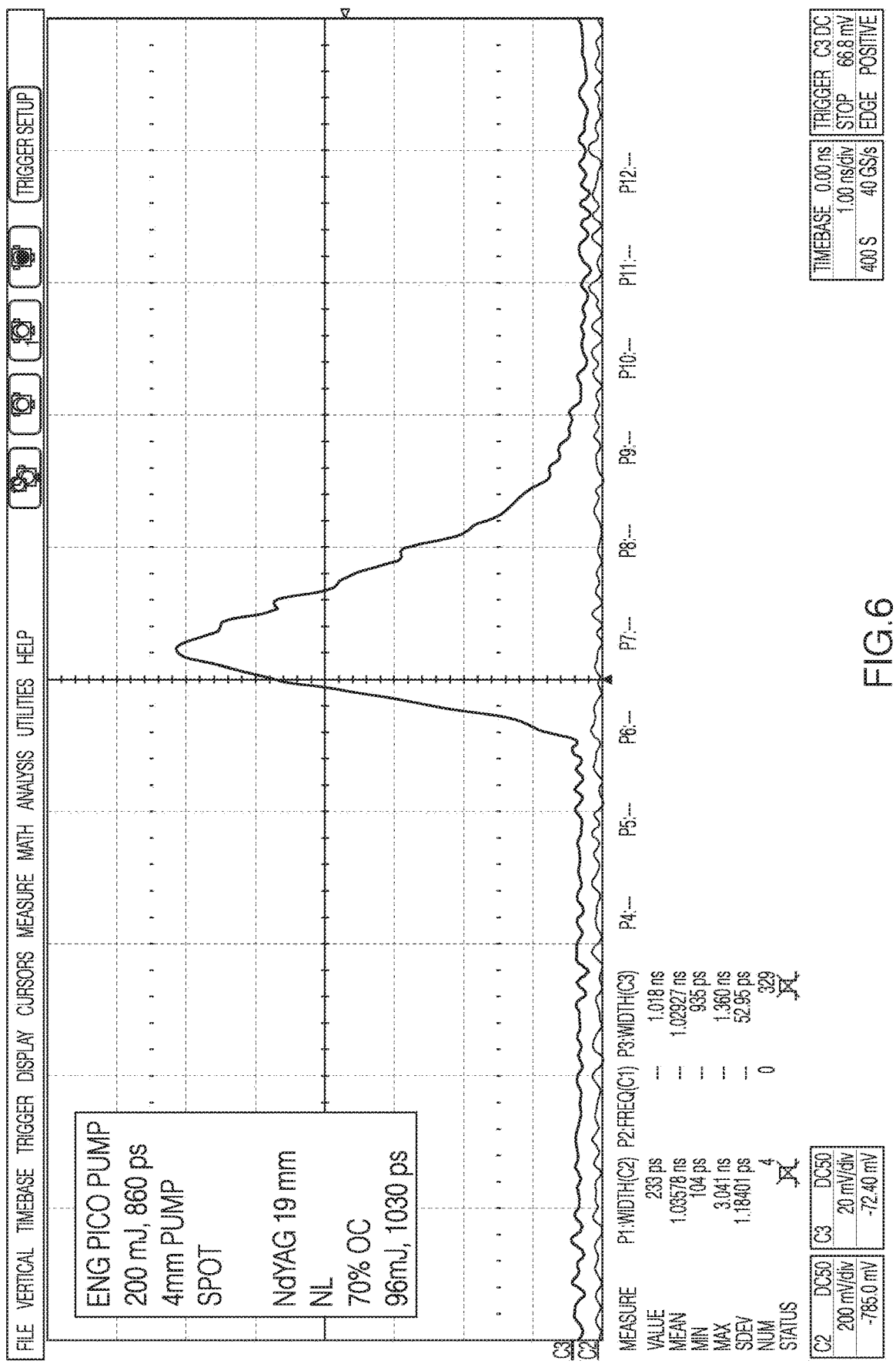
FIG. 6 illustrates an example of the output pulse shape of a short resonator Nd:YAG laser with a 70% output coupler.

An example plot of the output pulse shape of a short resonator Nd:YAG laser with a 70% output coupler is shown on FIG. 6. The Nd:YAG oscillator was pumped with 200 mJ per pulse, 860 ps pulse duration, 4 mm spot. The oscillator output at 1064 nm was 96 mJ per pulse, 1030 ps pulse duration. FIG. 6 shows that it is possible to generate and have an output that has a longer pulse duration 1030 ps than the pulse duration of the pumping pulse, 860 ps.

The short pulse output from the short roundtrip time oscillator (e.g., resonator) can be amplified to increase the pulse energy while keeping the pulse duration shorter than 1000 ps as described previously. When the oscillator and amplifier material are the same, for example Nd:YAG or Nd:YVO$_4$, the oscillator output wavelength can be matched to the amplifier gain profile to enable maximum energy extraction from the amplifier.

In one embodiment, the oscillator and amplifier materials are different from one another, optionally, it is advantageous for the oscillator to be made from different materials than the amplifier. For example a Nd:YVO$_1$ oscillator can be designed with a shorter roundtrip time vs a Nd:YAG oscillator, and a shorter output pulse duration will be produced by the Nd:YVO$_4$ oscillator when pumped with a short pulse Alexandrite laser, as compared to a Nd:YAG oscillator as discussed previously. Amplifying the Nd:YVO$_4$ oscillator output in a Nd:YVO$_4$ amplifier is relatively difficult because of the shorter fluorescence lifetime of Nd:YVO$_4$ is 100 ps versus the 230 ps fluorescence lifetime of the Nd:YAG. Amplifying the Nd:YVO$_4$ oscillator output in a Nd:YAG amplifier is possible, but sub-optimal because of the wavelength mismatch of the two different materials. According to Koechner "Solid-State Laser Engineering", 5$^{th}$ Ed., the laser wavelength of Nd:YVO$_4$ is 1064.3 nm, while the Nd:YAG peak gain wavelength is 1064.1 nm.

More detailed data for the laser output wavelength of a Nd:YVO$_4$ oscillator is published by Mingxin et al. "Performance of a Nd:YVO$_4$ microchip laser with continuous-wave pumping at wavelengths between 741 and 825 nm", Appl. Opt. v. 32, p. 2085, where the laser output wavelength of a Nd:YVO$_4$ microchip laser is shown to vary when the oscillator temperature is varied such that the laser output is 1063.9 nm when the oscillator temperature is about 0° C., and the laser output is 1064.5 nm when the oscillator temperature is about 100° C. An optimized laser system consisting of a Nd:YVO$_4$ oscillator and a Nd:YAG amplifier can be envisioned where the temperature of the oscillator and/or the amplifier is controlled and/or adjusted such that and the peak wavelength can be varied. In one embodiment, one controls the temperature of the Nd:YVO$_4$ so that it is well amplified in the amplifier. In one embodiment, the temperature of the oscillator and/or the amplifier is controlled so that one can provide a maximum energy output pulse with a minimal pulse duration. The range of temperature adjustment can be between about 0° C. and about 100° C., between about 20° C., and about 80° C., or between about 30° C., and about 70° C.

In addition to temperature control, other possible approaches to controlling and/or varying the peak wavelength can include external pressure applied to the laser material and doping the laser material with trace amounts of elements that would alter, for example, the crystal lattice stress. The approaches to varying peak wavelength such as oscillator and/or amplifier temperature control, pressure applied to the laser material, and doping the laser material can be employed alone or in combination.

Gain Uniformity

Gain uniformity in the lasing medium of a laser (e.g., in a solid state alexandrite lasing medium) has a direct effect on the uniformity of the output beam. In the case of a multimode, mode locked laser, as discussed previously herein (e.g., at FIGS. 1 and 2), where the beam energy propagates through the gain medium multiple times, a difference in gain uniformity of only a few percent can cause undesired modes with high peak fluences to develop. Gain uniformity is important because in the early stages of laser profile generation differences in gain uniformity in the lasing medium (e.g., a rod) have an exponential build up. Relatively small differences in the lasing medium gain profile (this is the pump profile) become exacerbated. To optimize the energy extracted from the resonator, a relatively even fluence is most desirable, for example, a round beam of even fluence is preferred. It is desirable to obtain a more uniform fluorescence profile such that the center of the lasing medium, for example, a crystal rod and its edges have substantially the same amount of fluorescence (e.g., a relatively even fluorescence).

In order to generate light via a light source (e.g., a pumped radiation source such as a flash lamp) the light couples into a lasing medium (e.g., a crystal laser rod) and that coupling can be done via a reflecting enclosure. The reflector can be diffuse (e.g., scattered) or specular (e.g., like a silvered surface that is mirror-like and not scattered). The lasing medium (e.g., crystal rod) absorbs the light coupled into it from the flash lamp. An absorption profile develops in lasing medium (e.g., the crystal rod). The function of the lasing medium is to absorb the light from the flash lamp and then to re-emit the light at changed wavelength (e.g., a longer wavelength). Where the lasing medium is a crystal rod if the middle of the rod absorbed the most light the middle of the rod would appear to be the brightest in that emitted wavelength—i.e., to emit the most changed wavelength. The phenomenon of the rod center being brighter than the rod edges is referred to as "fluorescence non-uniformity" this can generally occur for any laser where a flash lamp is coupled to a crystal (e.g., a crystal rod).

Figure 7:
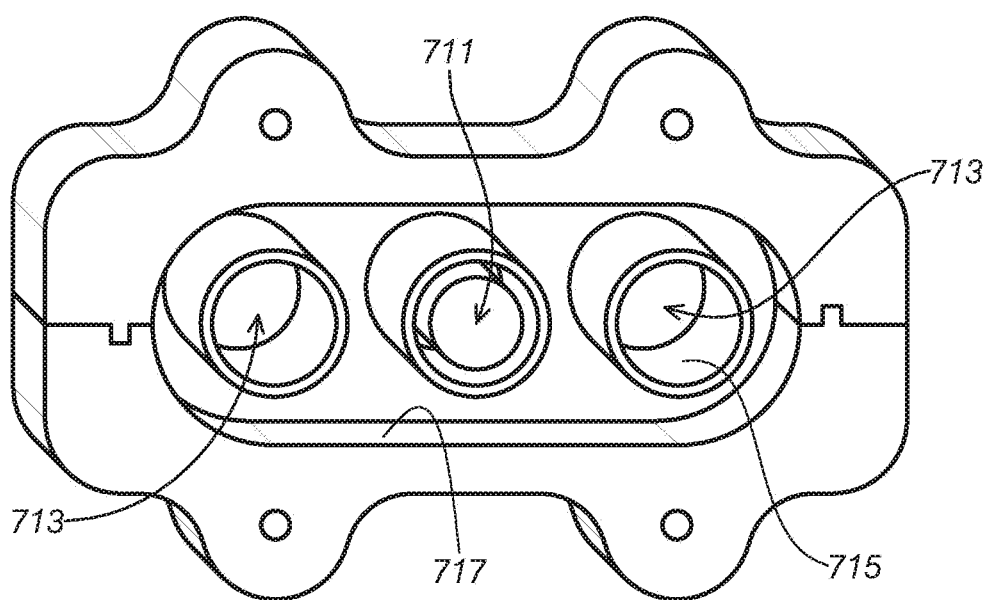
FIG. 7 is a cross-section of a pump chamber in accordance with various aspects of the applicants' teachings.

Turning now to FIG. 7, a cross section of a traditional dual-flash lamp diffuse pump chamber is depicted. Two flash lamps 713, each encased in glass coolant tubes 715, are arranged in parallel on both sides of a central lasing medium 711 (e.g., an alexandrite crystal rod lasing medium). The two flash lamps 713 and the lasing medium crystal 711 are all encased within a diffusing material 717 as shown in FIG. 7. Any diffusing material which would survive the high intensity light from the flash lamps 713 is suitable. Suitable modifications can include sandblasting a texture on the flash lamps 713 for example, on the coolant tubes 715 that encase the flash lamps 713, or in an area between the flash lamps 713 and the crystal lasing rod 711, shown in FIG. 7 and/or providing a coated a strip of aluminum with a white diffusing coating for example on one or more of the flash lamps 713 (e.g., on the coolant tube(s) 715). Some white diffusing coating examples include potassium sulfate, aluminum oxide, compressed PTFE and fumed silica.

Many factors can contribute to non-uniform gain distribution within the lasing medium. Lasing medium crystals may have different absorption coefficients at different wavelength(s) and/or along different axis of the crystal. This can be further imbalanced by the unequal output spectrum of the flash lamp pump source and how it matches the absorption spectrum of the lasing medium 711 (e.g., the active lasing medium). There is also the magnitude of the quantum defect within the flash lamp pump bands. It is desirable to improve gain uniformity on any material which lases, and the choice of lasing media is considered to be within the skill of an ordinary practitioner in view of the teachings provided herein.

The pump chamber geometry can also contribute to non-uniform gain by coupling more light into the crystal along one direction. In the case of an alexandrite crystal in a diffuse pump chamber, an increase in gain was observed in the direction of the flash lamps.

Figure 8:
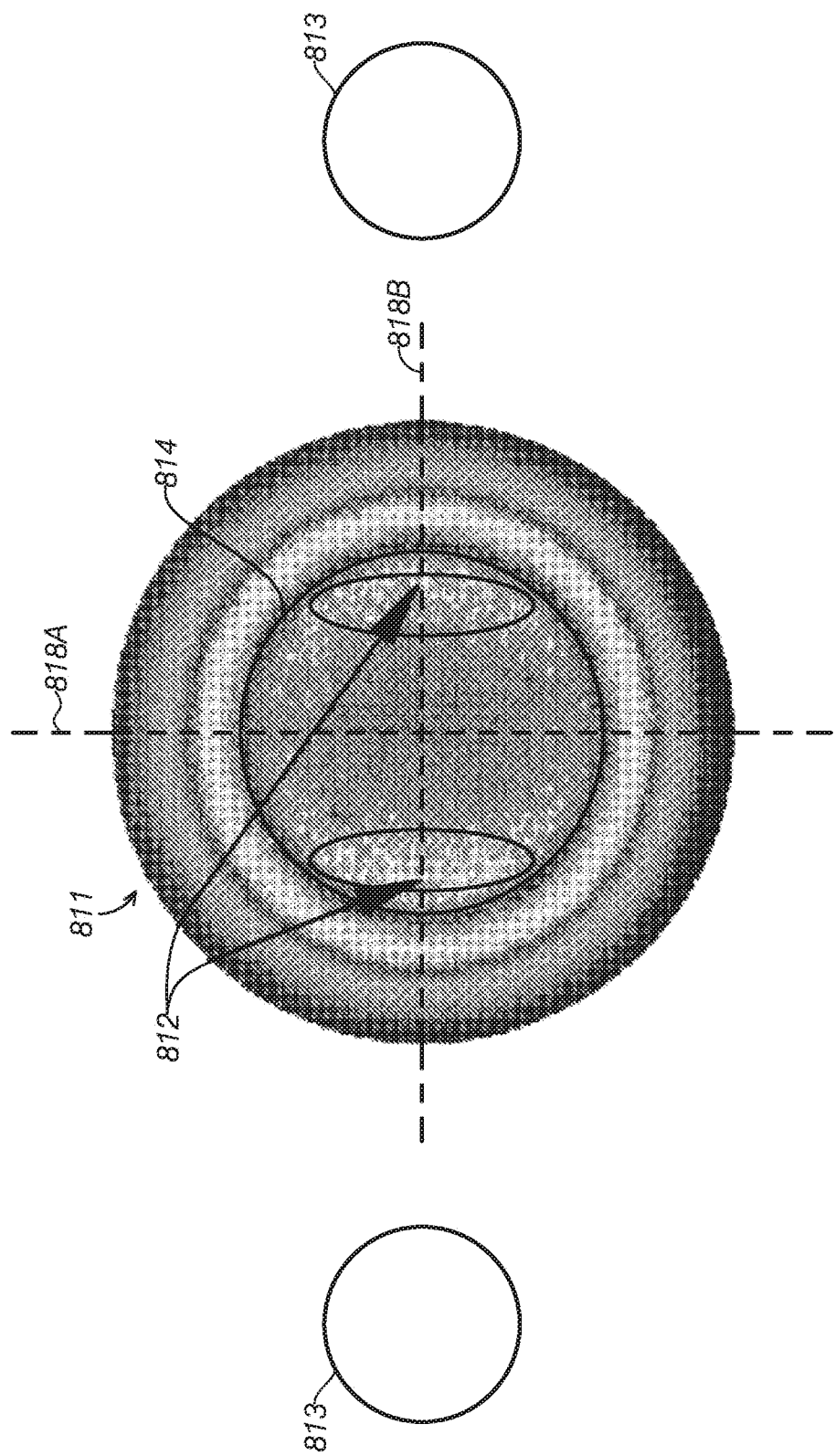
FIG. 8 is an axial-view image of the fluorescence of a pumped laser rod in accordance with various aspects of the applicants' teachings.

FIG. 8 depicts an image generated by the pump chamber geometry of FIG. 7, and captured by aligning a camera to the axis of the lasing medium 811 (e.g., the alexandrite crystal laser rod) and imaging the fluorescence of the pumped lasing medium 811 (e.g., the alexandrite crystal laser rod). The end face 814 of the lasing medium 811 is depicted as having a substantially circular boundary. The areas of the laser rod end face 814 that are most proximate to the flash lamps 813 exhibit high gain regions 812.

Figure 9:
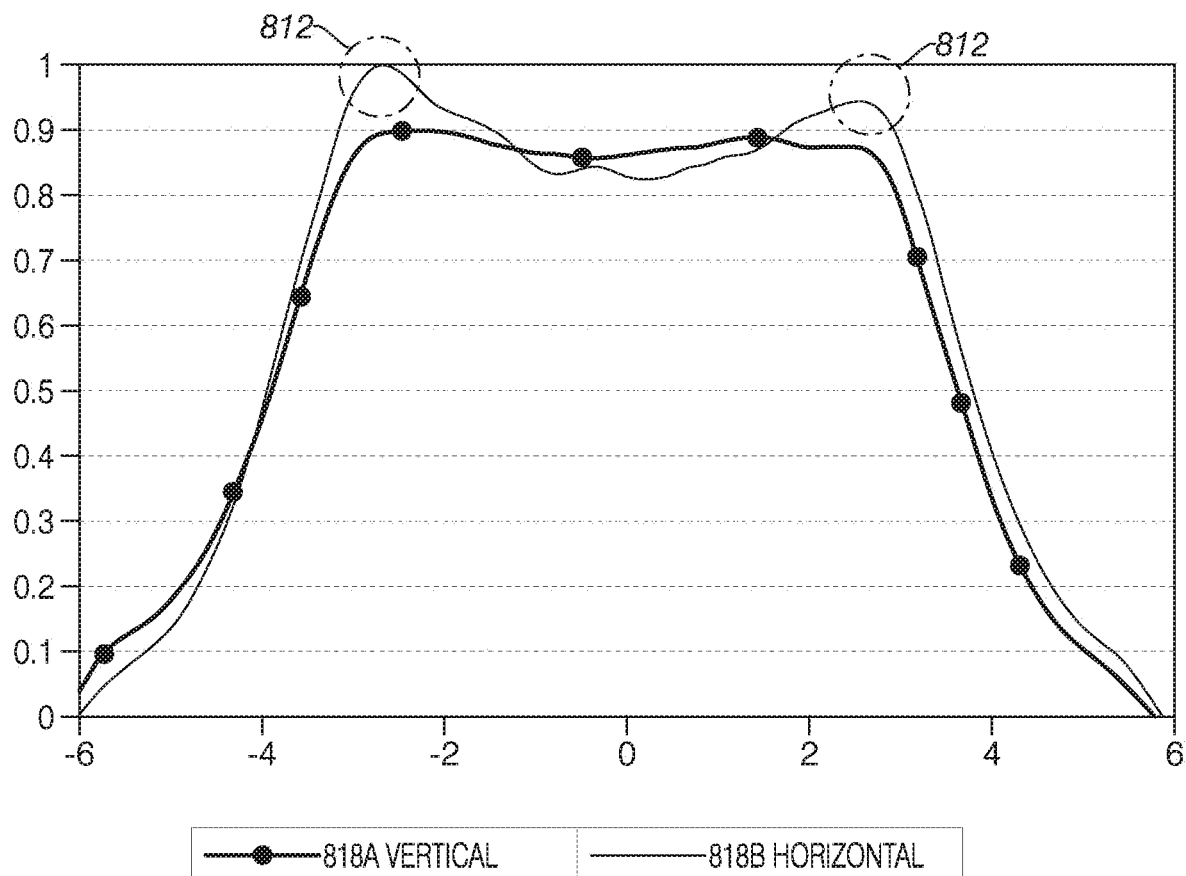
FIG. 9 is a graph depicting the normalized gain distribution in an unmodified diffuse pump chamber.

FIG. 9 depicts a graph showing profiles of the lasing medium 811 described in FIGS. 7 and 8 with the profiles taken along the horizontal axis 818B and along the vertical axis 818A. As can be seen by the graph in FIG. 9, the gain at the edge regions 812 of the end face 814 of the lasing medium 811 (in FIG. 8) in the horizontal direction 818B may be about 5 to 10 percent higher than the gain in the vertical direction 818A. These edge region 812 peaks correspond to the high gain regions depicted in the image of FIG. 8. This uneven gain distribution is problematic in that it leads to failure of the laser system due, for example, to uneven heating of the lasing medium that results in system breakdown and unacceptable down time and repair times. Further, where there is substantially uniform beam gain one can increase the system power output with less system failure than in the system where the gain is not uniform.

Accordingly, in order to improve system reliability, it is desirable to lessen and/or eliminate these gain peaks such that gain is substantially uniform across all axis of the lasing medium (e.g., that the gain is substantially uniform along both the horizontal axis 818B and along the vertical axis 818A of the lasing medium).

Embodiments of the present disclosure that improve gain uniformity include an optical system comprising a pump chamber with one or more elements that enable a substantially uniform gain across the lasing medium, for example, diffusing element(s) disposed between a flash lamp and a crystal. Elements that enable a substantially uniform gain across the lasing medium can include, for example, light shaping elements for example deflectors that lead to diffusion, scattering, refraction, and/or reflection or elements that provide absorption. In one embodiment, the element that enables a substantially uniform gain across the lasing medium is a diffusing element that acts to scatter a portion of the light coupling into the crystal and to increase the diffuse illumination of the rod, thereby avoiding non-uniform high-gain regions and achieving a circular symmetry to the gain region within the crystal rod.

Figure 10:
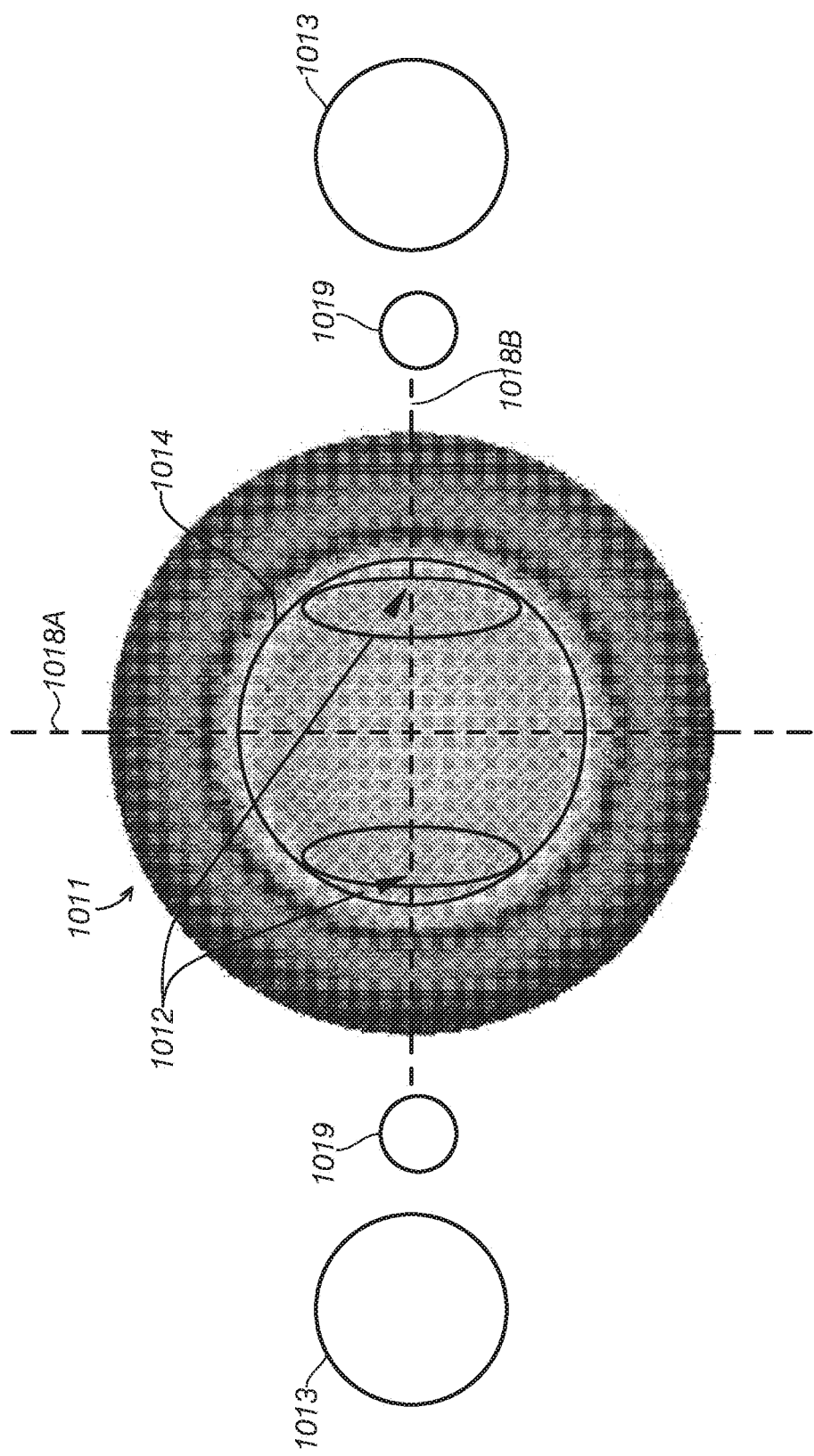
FIG. 10 is an axial-view image of the fluorescence of a pumped laser rod in accordance with an embodiment of the present disclosure.
Figure 11:
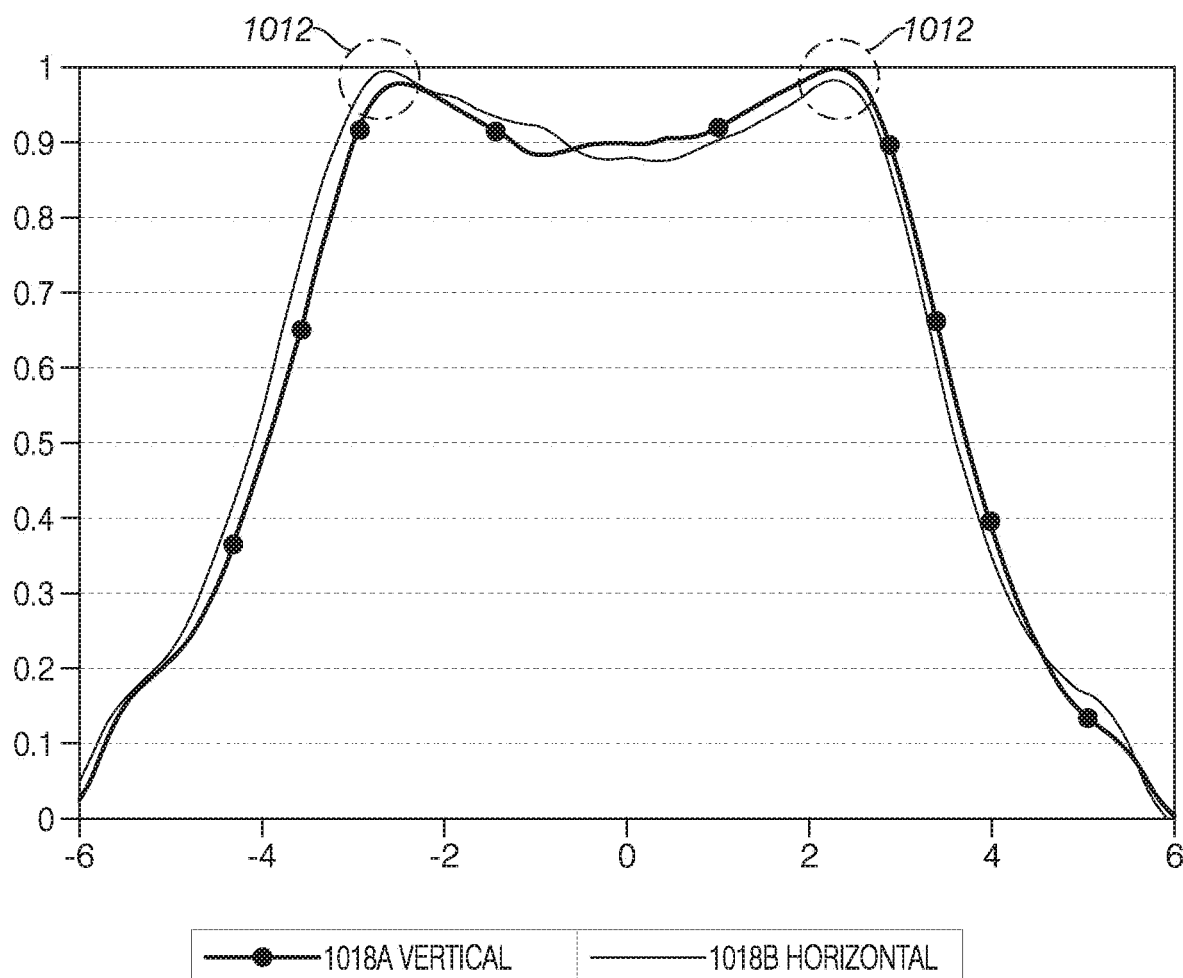
FIG. 11 is a graph depicting the normalized gain distribution in a modified diffuse pump chamber in accordance with an embodiment of the disclosure.

Referring to FIGS. 10 and 11, relatively uniform fluorescence can be achieved via elements that enable a substantially uniform gain across the lasing medium. Suitable elements include diffusing elements 1019. The stored photons from the rod fluoresce and enter into the cavity of the resonator formed by two or more mirrors. The photons travel between at least two mirrors that are along the relatively long axis of the gain medium and the photons build up energy through multiple trips between the opposing mirrors, which are substantially totally reflective. It is during this buildup of energy that the impact of the contrast between a non-uniform fluorescence and a relatively uniform fluorescence can be best understood when considering the laser energy profile that is emitted. A non-uniform fluorescence results in non-uniform energy emission from the laser, which is problematic due to the wear it causes on, for example, the optical components of the laser. For example, coatings present on the Pockels cells can be deteriorated by the non-uniform energy emission. A more uniform fluorescence results in a more uniform energy emission from the laser, which is desirable including due to the resulting increase in optical component longevity. By using an element that improves gain uniformity, such as a diffuser 1019 (e.g., the baffle and/or an absorber) obtaining more uniform gain and thereby more uniform fluorescence is favored, but at the expense of pumping efficiency, which is sacrificed due the presence of the element 1019.

Referring still to FIGS. 10 and 11, according to one embodiment of the disclosure, a lasing medium 1011 (e.g., a crystal rod) was placed between each flash lamp 1013 and a diffusing element 1019 (e.g., a baffle and/or an absorber) was placed in between the flash lamp 1013 and the lasing medium 1011 to scatter a portion of the light coupling directly into the lasing medium 1011 and to increase the diffuse illumination of the crystal rod lasing medium 1011. According to one embodiment, when a suitably-sized diffusing element 1019 was placed in the chamber, the lasing medium 1011 (e.g., a crystal rod) achieved substantially uniform gain (e.g., substantially circular symmetry). In one embodiment, the diffusing element 1019 is a 0.063 inch diameter alumina rod that was placed equidistant between the flash lamp 1013 and the crystal rod lasing medium 1011. Suitable diffusing element 1019 diameters can be about the same diameter as the lasing medium (e.g., about 0.375 inches) to as small a diameter as can be structurally sound (e.g., about 0.03 inches).

FIG. 10 depicts an image of the fluorescence using such an implementation. The fluorescence resulting from this chamber configuration shows the gain is more evenly distributed in a circularly symmetric fashion and the high-gain regions seen in FIG. 8 (when diffusing elements are absent) are eliminated.

The graph of FIG. 11 shows that the horizontal and vertical beam profiles have a closer agreement between the gain in the two axes (e.g., the vertical axis 1018A and horizontal axis 1018B show a substantially similar gain distribution) of the beam are in close agreement. The normalized gain distribution in the chamber having the diffusing element shows that the edge region 1012 of FIG. 10 lacks the peaks seen in FIG. 9 that were a result when there was no diffusing element in place.

In some embodiments, the choice of gain uniformity element material (e.g., a diffuser, absorber, deflector, baffle, scattering element, refractor, and/or reflector) and in the case of a material in the shape of a rod the selected diameter of the gain uniformity material can be adjusted to improve the beam uniformity of the system. The gain uniformity element (e.g., the diffusing element) need not sit between the flash lamp and the laser rod, rather the diffusing element can be a grating that is etched on the surface of one or more of the flash lamp or the laser rod.

Figure 12:
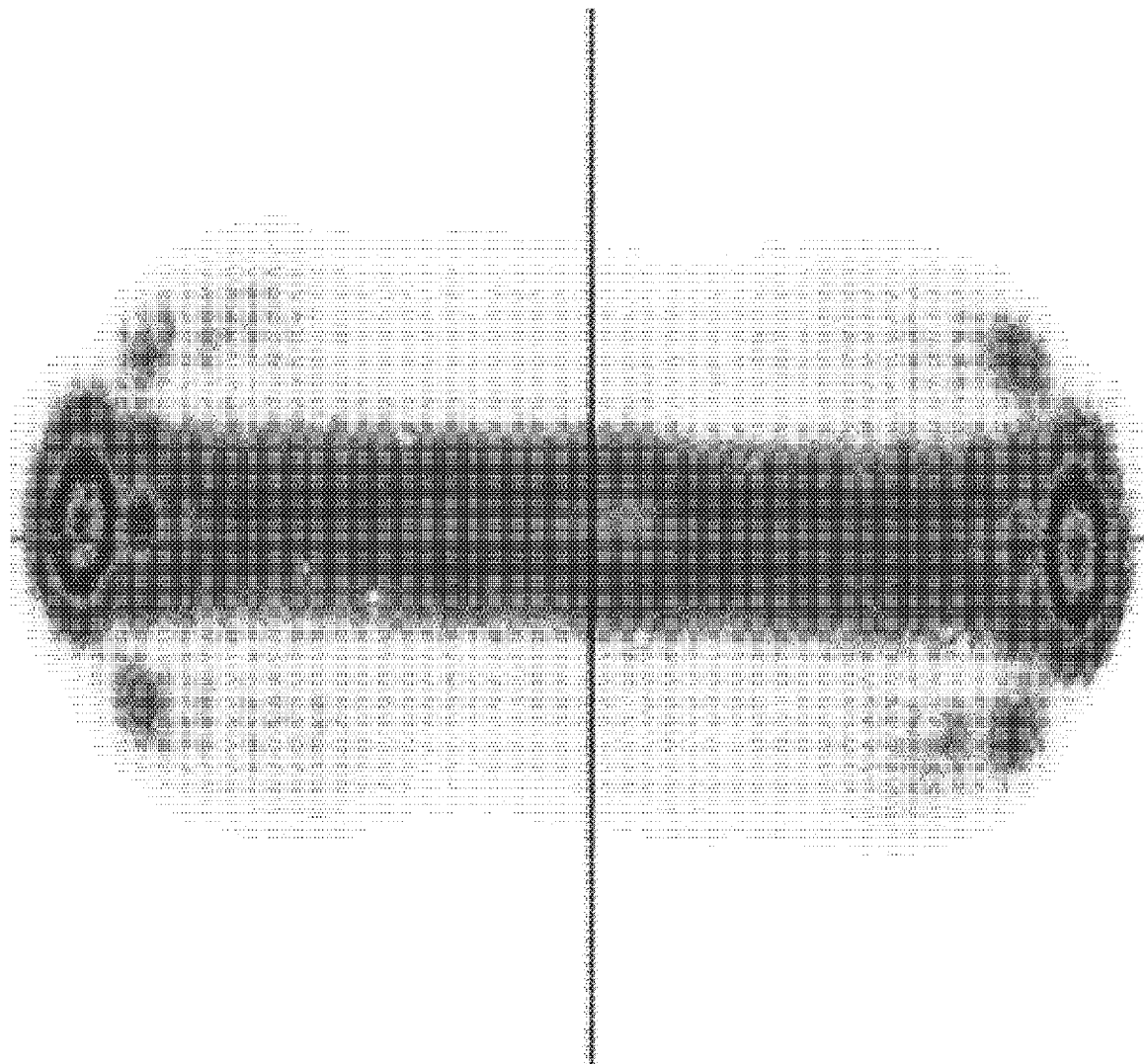
FIG. 12 is a laser beam profile image of a mode-locked laser using an unmodified pump chamber in accordance with various aspects of the applicants' teachings.
Figure 13:
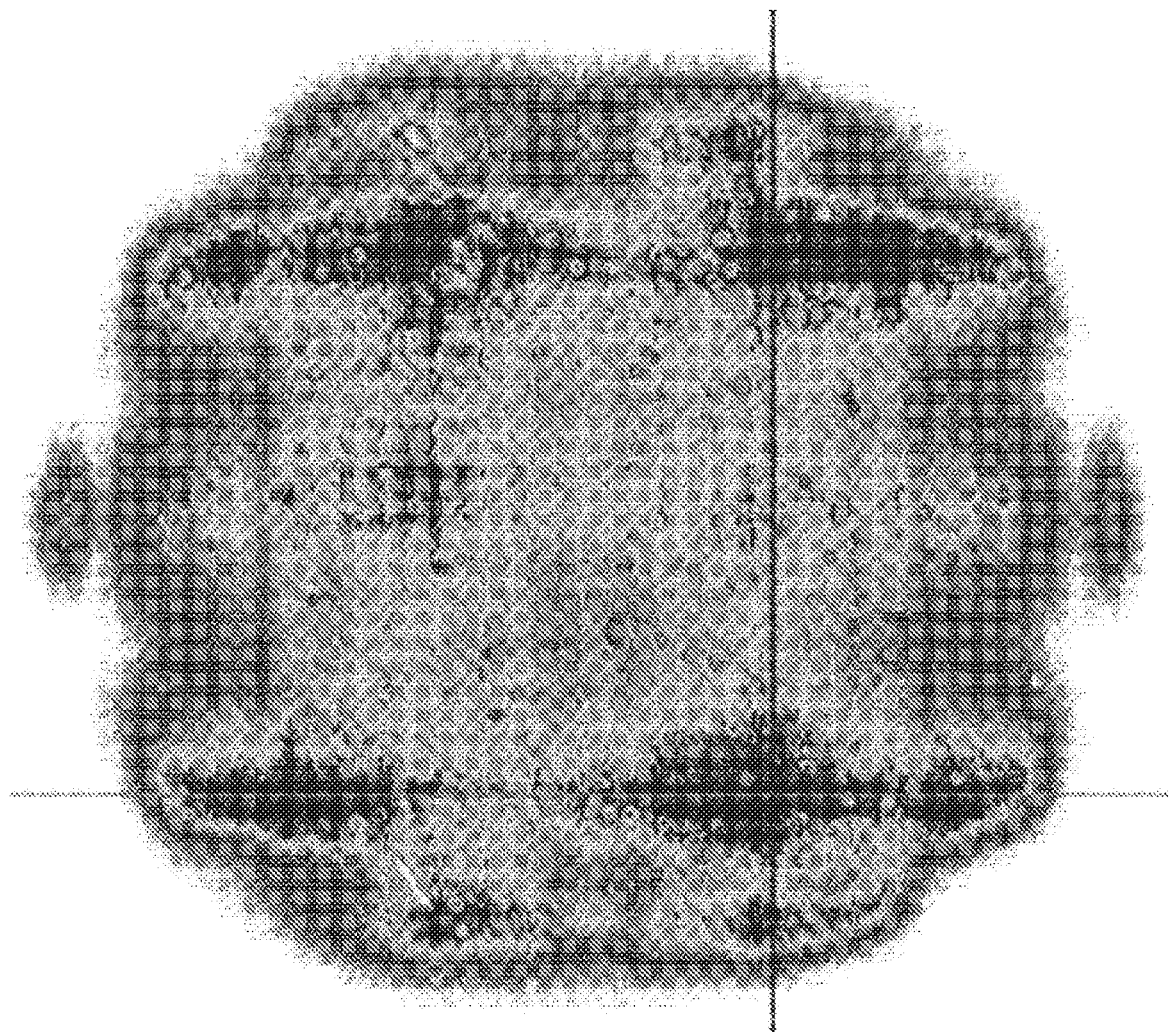
FIG. 13 is a laser beam profile image of a mode-locked laser using a modified pump chamber in accordance with an embodiment of the disclosure.

The effect of balancing and/or improving gain uniformity on the beam profile of a mode locked laser by altering pump chamber geometry, e.g., by adding one or more diffusing element, is dramatic. The image depicted in FIG. 12 shows the beam produced by the unmodified chamber described in connection with FIG. 8. The high peak fluence produced at the sides of the beam in FIG. 12 are beyond the damage threshold of the optics contained in the laser resonator. In comparison, the beam profile shown in FIG. 13, is produced by an embodiment that includes one or more diffusing elements (e.g., a baffled chamber with an alumina rod) like that described in connection to FIG. 10 and the beam profile is produced by the modified chamber is more circular, indicating the energy from the beam is spread over a greater area. As a result, the peak fluence of the beam generated with the embodiment of the pump chamber modified to include at least one diffusing element was greatly reduced and overall system power may be increased without damaging the optics in the resonator. As a result, the life and/or reliability of the laser system is improved due to the presence of the at least one gain uniformity improvement elements (e.g., a baffle).

Non-Spherical Lenses Lessen Free Space Propagation Mode Effect

Picopulse laser treatment energy relies on laser intensity, which is the square of the sum of the lasers electric fields. When free space propagation modes couple together the laser output intensity profile can tend toward non-uniformity. Free space propagation modes can include one or more of Hermite profiles, Leguerre profiles and Ince Gaussian profiles.

For the multi transverse mode laser it is beneficial to have sufficient transverse modes present such that the beam profile is filled in (substantially even). This ensures the peak fluence will be as close as possible to the average fluence. The ideal situation is the where the beam profile has a "top hat" beam profile, which looks like a top hat in profile e.g., referring to the representation of the normalized gain distribution shown in FIG. 1 in an idealized situation the two gain regions 1012 connect with a straight line and the sloping sides are much steeper. A low peak fluence will prevent laser damage to optical coatings and thus prolong the life of the laser.

The picopulse resonator can produce many multimode Hermite profile electric fields and can produce unwanted combinations of multimode Hermites. In order meet the desired laser treatment energy levels. Hermite profiles can result in high intensity profiles. These high intensity profiles can damage the optics of the resonator leading to reduced lifetime issues.

It is desirable to lessen the impact of free space propagation modes including Hermites in the beam output profile. Introducing a lens element that provides astigmatism can act to decouple free space propagation modes thereby obviating or lessening their impact on the beam profile. Lens elements that can lessen the impact of free space propagation modes (e.g., Hermites) could be for example, cylinder lens, angled spherical lens, anamorphic prisms, etc.

Unlike a spherical lens, which is cut from a sphere, a non-spherical lens (e.g., an astigmatic lens such as a cylindrical lens) can be cut from a rod. Specifically, a non-spherical lens can be cut along the long axis of a rod such that its end face looks like the letter "D". The non-spherical lens provides only one axis of curvature in contrast to a spherical lens which provides two axis of curvature. When light travels through the curved axis the light is deviated (e.g., focused or defocused) by the curvature of the lens such that the light is different in the x-plane versus the y-plane. Light that travels across the other axis does not get focused or defocused—it sees no deviation.

Alternatively, a spherical lens may be angled such that light impinges on the spherical lens at an angle that provides the effect of a cylindrical lens such that the angled spherical lens output of light is different in the x-plane versus the y-plane. These are just a few of many ways to produce an astigmatic lens effect. Other methods or means of utilizing lenses or prisms to produce an astigmatic effect are known to those of skill in the relevant art.

There is a phenomenon in multimode lasers by which multiple Hermite profiles can build up within a resonator and interfere with each other to cancel portions of one another out and thereby create hotspots that give an unacceptable laser beam intensity profile. By controlling and/or managing the mix of Hermites their interference in the laser output can be limited. The mix of Hermites can be limited by utilizing different astigmatism for the x and y axis' in the resonator. In this way, the astigmatic element prevents multiple Hermite profiles from interfering with one another to produce a bad profile. Rather, each individual Hermite profile exits the laser individually. In this way, the astigmatic lens element avoids Hermite's canceling portions of one another out that results in undesirable hot spots in the laser beam profile that can cause wear on the optics of the system. As discussed previously, it is important to provide a beam output that shows a relatively even energy distribution (e.g., beam uniformity). The astigmatic effect element can aid in beam uniformity, because it avoids coupling of free space propagation modes that result in undesirable hot spots.

Figure 14A:
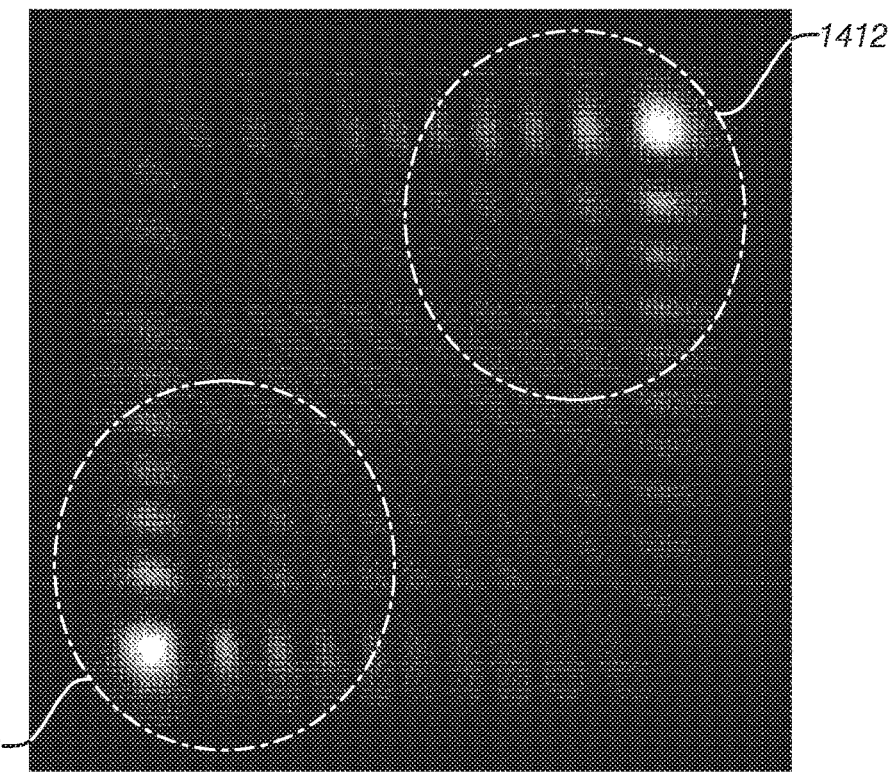
FIG. 14A shows a laser intensity profile that includes the free space propagation mode effects caused by two propagating Hermite fields that are in phase with one another in accordance with various aspects of the applicants' teachings.

An example of an unwanted two electric field combination with a resultant laser intensity combination is shown FIG. 14A. In FIG. 14A, the majority of the beam energy is contained in two distinct regions 1412 within the profile. This is an unwanted electric field, which is a result of the combination of two individual propagating Hermite fields that remain in phase, i.e. each field is in step with the other.

By introducing astigmatism into the picopulse resonator the undesirable phase relationship of the propagating Hermite electric fields is broken along the astigmatic axes (physics Gouy phase effect). Using the same two Hermites of the previous combination example shown in FIG. 14A, but now showing the effect of phase mismatch created by the astigmatic element (e.g., astigmatic lens) on intensity is FIG.

Figure 14B:
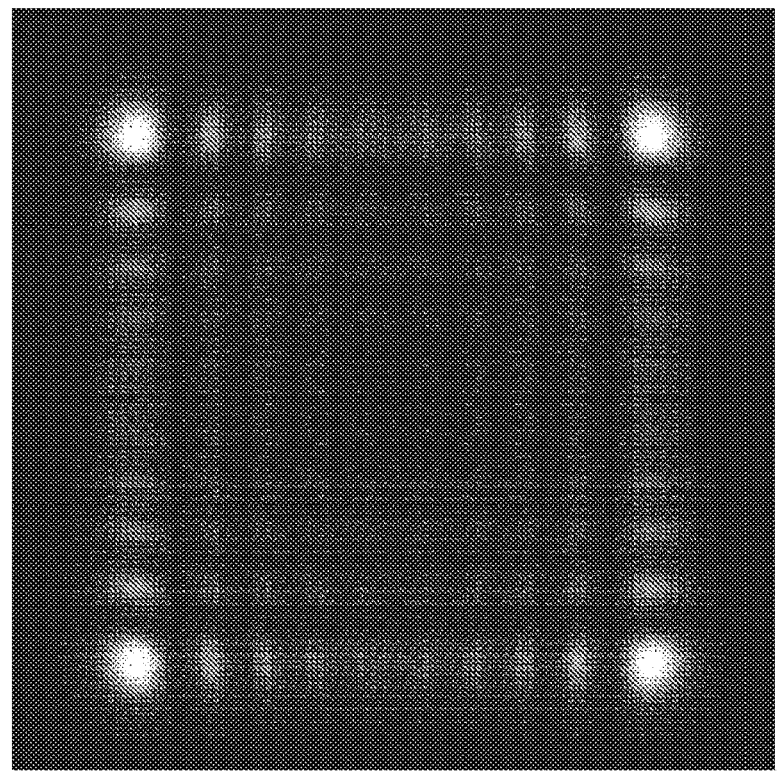
FIG. 14B shows a laser intensity profile when an astigmatic element is introduced to decouple propagating Hermite fields such that they are not in phase with one another in accordance with various aspects of the applicants' teachings.

14B. The FIG. 14B profile has a better fill of energy or distribution of energy in that all four corners of the beam profile are illuminate, which is much less likely to damage the optics compared to the beam profile in FIG. 14A where energy is concentrated into two of the four corners of the beam profile.

The picopulse laser transverse mode profile is improved when astigmatism is introduced into the resonator. The astigmatism essentially provides two resonator configurations, each with a preferred set of modes. In one embodiment, astigmatism was introduced by a weak cylindrical lens «0.5 Dioptres. The astigmatic generating element could be placed anywhere within the resonator path. The cylinder lens worked well when its axis was perpendicular or parallel to the plane polarized light in the picopulse laser.

There are many approaches to introducing an astigmatic element to the resonator, for example, the goal of different net curvature can be achieved within a resonator by, for example, positioning a spherical lens or spherical lenses such that one or more spherical lens is tilted relative to the optical axis, thereby providing one or more astigmatic element(s). Alternatively, the beam can be expanded in a single direction (e.g., anamorphic expansion) prior to a lens or a spherical mirror.

Another method of free space propagation mode control is to place an obscuration (e.g., a wire) at the electric field zero crossings of a wanted mode. The obscuring element (e.g., for a Hermite a line, fora LeGuerre a radial obscuration) can be produced in a substrate or in the anti-reflection coating on a substrate. The obscuration element prevents unwanted free space propagation modes from lasing and effectively filters them out of the distribution of energy lased from the system. Preferably, obscuring elements have thin lines (e.g., lines that are <50 um thick), which can be produced, for example, by UV laser writing directly into the substrate (e.g., glass). The lines are best situated near the rod where resonator misalignment will have least effect on line position.

Picosecond Laser Sub-Harmonic Resonator

In a simple, free running, laser resonator a number of longitudinal modes develop independently. These modes have no set phase relationship so they are free to interfere with each other, which leads to fluctuations in the output intensity of the laser as the output signal is an average of all modes inside the resonator.

In frequency space, each mode corresponds to a spectral line and the separation of spectral lines is called the axial mode interval, c/2 L, where c is the speed of light and L is the optical path length of the resonator (2 L is the round trip optical path length of the resonator). The temporal output of the laser is related to the frequency space by a Fourier transform.

Mode locking is a technique used to create pulses of light with durations less than 1 nanoseconds. This is done by introducing an element which periodically inhibits the lasing of the resonator. This inhibiting element can take a number of forms but the implementation is broken down into two categories:

(a) Passive mode locking uses an element whose properties are varied by the light inside the resonator
(b) Active mode locking utilizes elements that need to be driven using external signals.

When the mode locking element is a Pockels cell it can be used in combination with a polarizer to vary the losses inside of the resonator. Using the Pockels cell in this manner is equivalent to modifying the reflectivity of one of the cavity mirrors.

The voltage applied to the Pockels cell can be increased until the lasing within the resonator is inhibited. The highest voltage in which laser emissions are produced is called the threshold voltage. To mode lock the resonator the voltage is modulated around the threshold voltage at a set frequency. When the voltage is lower than threshold the losses are less and lasing can occur. Voltages higher than threshold will result in no lasing.

In traditional mode locked lasers the oscillation period of the lasing inhibitor is equal to the time for a pulse to travel one round trip through the resonator. Since lasing is inhibited when the Pockels cell voltage is above threshold a single pulse of light is formed which propagates through the resonator. This pulse is formed of longitudinal modes whose phases are aligned. The peak longitudinal mode will have a frequency which experiences minimal losses when propagating through the mode locking element. In the region around this peak the modes will experience greater loss for greater differences in frequency. This creates a relationship between the longitudinal modes that doesn't exist in free running lasers and leads to the smaller pulse durations of mode locked lasers.

A traditional mode locked laser works based on the principal that the electrical switching frequency at which a mode locker (e.g., a Pockels cell) is switched is directly tied to the optical path length of the resonator. The optical path length of the mode locked resonator can range from about 3 meters to about 0.5 meters in length, for example.

Active mode locking involves modulation of a component inside the resonator at a frequency whose period is equal to the time required for light to propagate one round trip in the resonator. The purpose of this component is to only allow lasing to occur over a portion of this period and the end result is a single pulse of light traveling within the resonator.

In the case of the traditional picosecond resonator (i.e., the fundamental) the modulation is applied to the Pockels cell which requires several hundred volts of modulation in order to produce the mode locking effect. The length of the picopulse resonator is limited by the highest modulation frequency that can reliably be produced at this voltage level.

At this point 75 MHz is believed to be the maximum frequency which can be created which leads to a 2 meter long resonator. A shorter resonator would be preferable from a mechanical point of view as the mirror positional sensitivity increases as the resonator length increases.

Figure 15A:
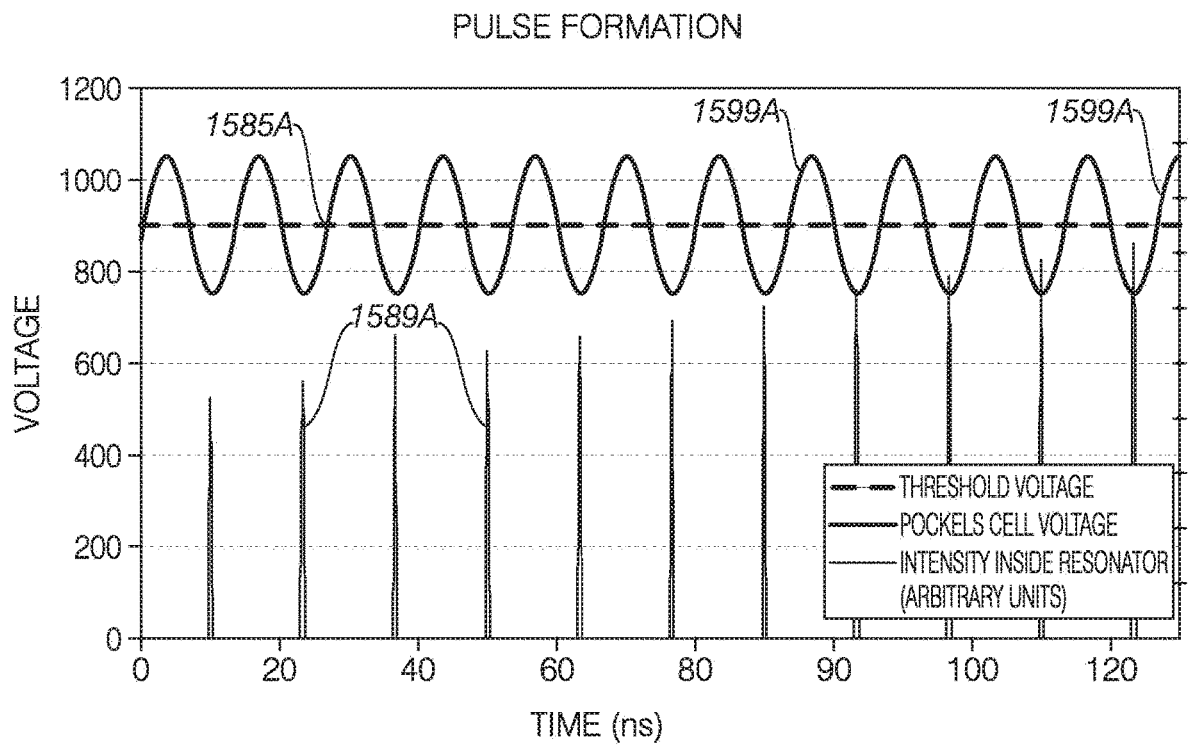
FIG. 15A shows the modulation signal applied to the Pockels cell in a picosecond resonator and the intensity that builds up in the resonator over time in accordance with various aspects of the applicants' teachings.

FIG. 15A shows the modulation signal 1599A applied to the Pockels cell in a traditional picosecond resonator having a threshold voltage 1585A. In the presence of this modulation signal 1599A the intensity 1589A builds up in the resonator over time.

For example, a resonator having an optical round-trip length of 10 ft requires an electrical switching frequency of about 100 MHz. The speed of light in air is approximately 1 ft per nanosecond; therefore, the round-trip time of a photon in a 10 ft resonator is about 10 nanoseconds. The Pockels cell therefore is switched at about 100 MHz. In accordance with a traditional picosecond resonator (i.e., the fundamental) picosecond seed pulses that are generated in the resonator pass through the Pockels cell one time per electrical switching event. Unfortunately, switching the Pockels cell at 100 MHz is not an option due limitations and to issues such as fidelity issues.

In order to resolve such a problem, a sub-harmonic solution may be employed. The sub-harmonic approach can include (A) divide the Pockels cell switching frequency by a factor of the $n^{th}$ harmonic (e.g., by any power of 2) and/or (B) dividing the optical path length by a factor of the $n^{th}$ harmonic (e.g., by any power of 2). The approaches A and B were first tested on a prototype. This test was done whereby a traditional picopulse laser approach to a 75 MHz modulation frequency would call for a 2 meter resonator length (A) using the switching frequency approach the modulation frequency of the existing 75 MHz, 2 meter resonator was changed to a modulation frequency of 37.5 MHz. Then (B) using the optical path length approach the 75 MHz modulation frequency was maintained, but the path length of the resonator was reduced to 1 meter, which was half the original 2 meter length. Approaches (A) and (B) produced pulses of similar pulse widths to the traditional 75 MHz and 2 meter resonator length design.

Embodiments Relating to Dividing the Pockels Cell Switching Frequency by a Factor of the $n^{th}$ harmonic (e.g., by any n>1, n is a Whole Number.)

In one embodiment, a system in which the electrical switching frequency is a sub-multiple of the standard resonator switching frequency is implemented. In other words, a system is implemented in which seed pulses that flow in the resonator pass through the Pockels more than one time for every electrical switching event. The modulation signal can be viewed as a gate which allows the light to pass. When the Pockels cell voltage is below threshold the gate is closed. So a single pulse travels around the resonator passing the Pockels cell while the gate is open and all other radiation is suppressed when the gate is closed. Considering this analogy, the proposed idea is to close the gate every other round trip through the resonator. This would allow for shorter resonator lengths for a given modulation frequency.

Figure 15B:
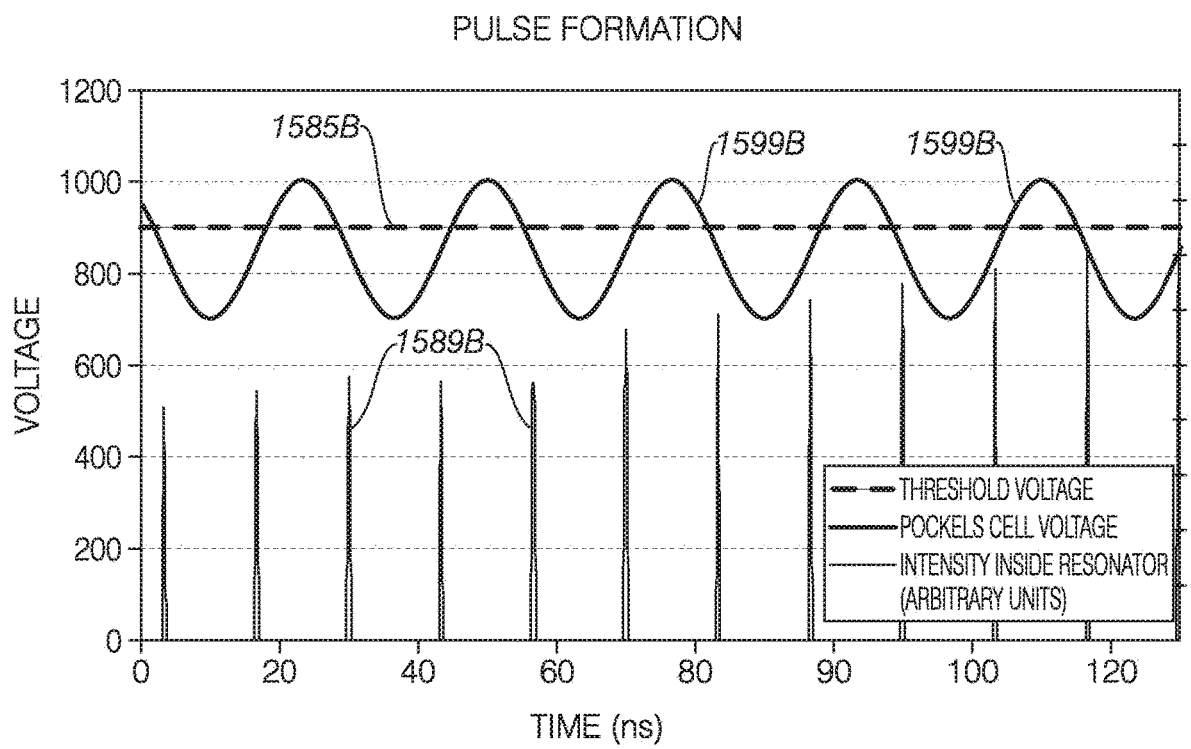
FIG. 15B shows the modulation signal applied to the Pockels cell in a sub-harmonic picosecond resonator and the intensity that builds up in the resonator over time in accordance with various aspects of the applicants' teachings.

FIG. 15B shows a lower frequency modulation signal 1599B applied to the Pockels cell in a sub-harmonic picosecond resonator having a threshold voltage 1585B, this is the nth harmonic of the switching frequency of frequency modulation signal 1599A shown in FIG. 15A. In the presence of this lower frequency modulation signal 1599B the intensity 1589B builds up in the resonator over time such that, referring now to FIGS. 15A and 15B, at the time of about 140 nanoseconds the intensity inside the resonator 1589A and 1589B is substantially the same.

While we have shown the modulation signal 1599A in FIG. 15A and the modulation signal 1599B in FIG. 15B as featuring an idealized sine wave, in actual usage in the picosecond system the modulation signal has at least some harmonic content. More specifically, the modulation signal should have from about 5% to about 50% harmonic content, and from about 10% to about 20% harmonic content.

Embodiments Relating to Dividing the Optical Path Length by a Factor of the Nth Harmonic (e.g., by n>1, n is a Whole Number).

In another sub-harmonic approach, inhibiting the lasing on every other pass through the resonator would be sufficient to produce a mode locked pulse. This sub-harmonic approach can decrease the picopulse resonator length and/or ease the electrical burden by decreasing the modulation frequency.

In a normal mode locked laser a pulse of light propagates one round trip through the resonator for each oscillation of the mode locking element. If the element were instead driven at half the frequency, or the first sub harmonic, then the pulse would travel two round trips for each oscillation. During the first trip the pulse would travel through the resonator while the element was at maximum transmission. This is the same in the standard mode locking resonator. During the second trip the pulse will hit the element at minimal transmission and experience loss. If the gain of the active medium is sufficient then the pulse energy will increase more during the first trip than it loses in the second trip and a mode locked pulse can be generated.

Since the modulation frequency is tied to the propagation time through the resonator, modulating with a subharmonic provides the benefit of a shorter overall resonator length. For example, if the electrical circuit can reliably switch the required voltages at 50 MHz then the period of one oscillation is 20 nanoseconds. A 6 meter round trip cavity length is required for a travel time of 20 nanoseconds. However, if 50 MHz is the first subharmonic of the resonator then the round trip cavity length is cut in half to 3 meters. If we consider the frequency of oscillation to be a limiting factor then subharmonic operation provides smaller resonators than traditional mode locking.

A method of evaluating mode locked resonators was developed by Kuizenga and Siegman (D. J. Kuizenga and A. E. Siegman, "FM and AM mode locking of the homogenous laser-Part1: Theory", IEEE Journal of Quantum Electronics, November 1970, pp. 694-708 [1]) Their analysis applies a self-consistent criterion on the pulse after one round trip of the resonator. Energy travels through an active medium and back then through a modulator and back.

The following expression, Formula (1), relates the pulse width, $\tau$, to the gain, g, modulation depth, $\delta$, modulation frequency, fm, and gain bandwidth, $\Delta f$.

$$\tau = \frac{\sqrt{\sqrt{2}\ln 2}}{\pi}\left(\frac{g}{\delta}\right)^{\frac{1}{4}}\left(\frac{1}{f_m \Delta f}\right)^{\frac{1}{2}} \qquad \text{Formula (I)}$$

A similar analysis can be done for the sub harmonic resonator, but the self-consistent criterion can only be applied after n round trips of the resonator, n>1, n a whole number. The overall transmission function for the n round trips must be computed to discover the modulation depth variable ($\delta$). The sub harmonic overall transmission will be <100% and shows a variation from one round trip to the next during the n round trips taken for the analysis.

In one embodiment, a resonator was constructed using an 8 mm Alexandrite rod, 85 mm in length and a KD*P Pockels cell. In the first configuration the Pockels cell is driven at 75 MHz and the path length is 2 meters. This system is operating with the traditional fundamental mode locking frequency for this resonator. Pulsewidth of 550 picoseconds are produced by this configuration. The system is then configured to mode lock at the first sub harmonic such that it modulates at 50 MHz and the path length is decreased to 1.5 meters. Pulses of 700 picoseconds are produced by this system. Even though the equation at Formula (1) was developed for a traditional mode locking approach the pulse widths of these two systems reasonably follow the square root of one over the frequency term of the above expression.

Figure 16:
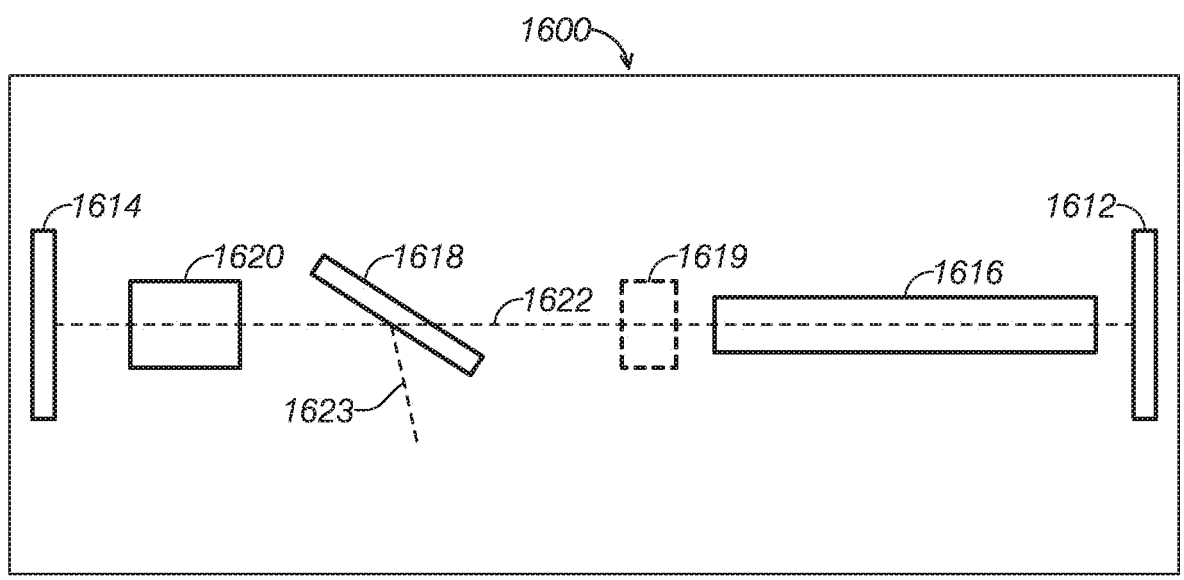
FIG. 16, in a schematic diagram, illustrates an exemplary system for generating picosecond pulses in accordance with various aspects of the applicants' teachings.

FIG. 16 depicts a representative embodiment of an apparatus 1600 according to the present disclosure, which is capable of achieving the above pulse duration and energy output parameters, suitable for the effective treatment of pigmented lesions through photomechanical means. Advantageously, the apparatus includes a resonator (or laser cavity) capable of generating laser energy having the desirable pulse duration and energy per pulse, as described herein. The resonator has a characteristic longitudinal or optical axis 1622 (i.e., the longitudinal flow path for radiation in the resonator), as indicated by the dashed line. Also included in the representative apparatus shown are an electro-optical device, in this case a Pockels cell 1620, and a polarizing element also referred to as a polarizer 1618 (e.g., a thin-film polarizer). During operation, the laser pulse output will be obtained along output path 1623.

At opposite ends of the optical axis 1622 of the resonator are a first mirror 1612 and a second mirror 1614 having substantially complete reflectivity. This term, and equivalent terms such as "substantially totally reflective" are used to indicate that the mirrors 1612 and 1614 completely reflect incident laser radiation of the type normally present during operation of the resonator, or reflect at least 90%, preferably at least 95%, and more preferably at least 99% of incident radiation. The mirror reflectivity is to be distinguished from the term "effective reflectivity," which is not a property of the mirror itself but instead refers to the effective behavior of the combination of second mirror 1614, Pockels cell 1620, and polarizer 1618 that is induced by the particular operation of the Pockels cell 1620, as discussed in detail below.

In particular, a laser pulse traveling from lasing or gain medium 1616 towards second mirror 1614 will first pass through polarizer 1618, then Pockels cell 1620, reflect at second mirror 1614, traverse Pockels cell 1620 a second time, and finally pass through polarizer 1618 a second time before returning to gain medium 1616. Depending upon the bias voltage applied to Pockels cell 1620, some portion (or rejected fraction) of the energy in the pulse will be rejected at polarizer 1618 and exit the resonator along output path 1623. The remaining portion (or non-rejected fraction) of the energy (from 0% to 100% of the energy in the initial laser pulse) that returns to the medium 1616 is the "effective reflectivity" of second mirror 1614. As explained above, for any given applied voltage to Pockels cell 1620, the effective behavior of the combination of second mirror 1614, Pockels cell 1620, and polarizer 1618 is indistinguishable, in terms of laser dynamics, from that of a single partially reflective mirror, reflecting the same non-rejected fraction described above. An "effective reflectivity of substantially 100%" refers to a mirror that acts as a substantially totally reflective mirror as defined above.

Also positioned along the optical axis 1622 of the resonator is a lasing or gain medium 1616, which may be pumped by any conventional pumping device (not shown) such as an optical pumping device (e.g., a flash lamp) or possibly an electrical or injection pumping device. A solid state lasing medium and optical pumping device are preferred for use in the present disclosure. Representative solid state lasers operate with an alexandrite or a titanium doped sapphire crystal. Alternative solid lasing media include a yttrium-aluminum garnet crystal, doped with neodymium (Nd:Y AG laser). Similarly, neodymium may be used as a dopant of pervoskite crystal (Nd:YAP or Nd:Y Al03 laser) or a yttrium-lithium-fluoride crystal (Nd:YAF laser). Other rare earth and transition metal ion dopants (e.g., erbium, chromium, and titanium) and other crystal and glass media hosts (e.g., vanadite crystals such as YV04, fluoride glasses such as ZBLN, silica glasses, and other minerals such as ruby) of these dopants may be used as lasing media.

The above mentioned types of lasers generally emit radiation, in predominant operating modes, having wavelengths in the visible to infrared region of the electromagnetic spectrum. In an Nd:YAG laser, for example, population inversion of Nd+3 ions in the YAG crystal causes the emission of a radiation beam at 1064 nm as well as a number of other near infrared wavelengths. It is also possible to use, in addition to the treating radiation, a low power beam of visible laser light as a guide or alignment tool. Alternative types of lasers include those containing gas, dye, or other lasing media. Semiconductor or diode lasers also represent possible sources of laser energy, available in varying wavelengths. In cases where a particular type of laser emits radiation at both desired and undesired wavelengths, the use of filters, reflectors, and/or other optical components can aid in targeting a pigmented lesion component with only the desired type of radiation.

Aspects of the disclosure also relate to the manner in which the apparatus 1600, depicted in FIG. 16, is operated to generate laser energy with the desirable pulse duration and energy output requirements discussed above. For example, laser energy from the lasing medium 1616 is reflected between the first mirror 1612 and second mirror 1614 at opposite ends of the optical axis 1622 of the resonator. Laser energy emanating from the lasing medium 1616 therefore traverses the thin film polarizer 1618 and Pockels cell 1620 before being reflected by the substantially totally reflective second mirror 1614, back through the Pockels cell 1620 and polarizer 1618.

Naturally birefringent laser gain materials such as alexandrite, and other crystals such as Nd:YV04 exhibit a large stimulated emission cross-section selectively for radiation having an electric field vector that is aligned with a crystal axis. Radiation emitted from such lasing materials is therefore initially linearly polarized, the polarized axis corresponding to the materials highest gain crystalographic axis. Typically the polarizer 1618 is configured for transmission of essentially all incident radiation by proper alignment with respect to the electric field vector.

Optionally, referring still to FIG. 16, an astigmatic element 1619 may be placed anywhere along the optical axis 1622 including, for example, directly in front of one or more mirrors 1612, 1614. Further, one or more of the mirrors 1612, 1614 can provide an astigmatic element by possessing two different radii of curvature that are perpendicular to one another.

Referring to the simple apparatus of FIG. 16. When the laser threshold bias DC voltage is applied to the Pockels cell 1620 then the effective mirror reflectivity is set at such a value that the medium 1616 will lase. Varying the voltage above and below the bias voltage is called modulating the voltage. In one embodiment, using an Alexandrite medium 1616, a typical DC bias voltages applied to Pockels cells is around 650V and the modulated voltage applied to the Pockels cell is about 200V.

Figure 17:
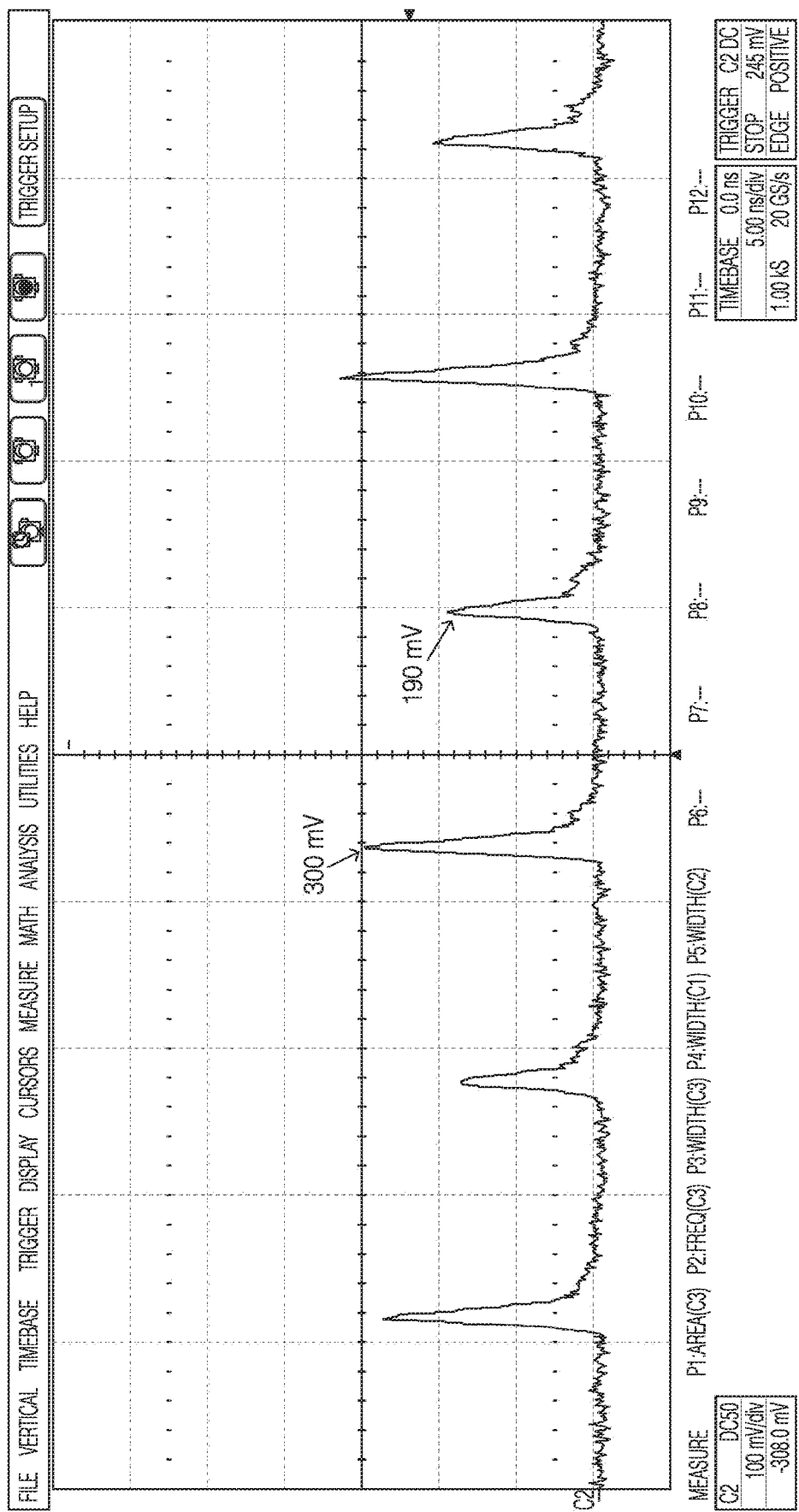
FIG. 17 is a plot of the seed pulse generation with a laser capable of generating a sub-harmonic pulse group at 300 mV when the Pockels cell voltage was low and at 190 mV when the Pockels cell voltage was high in accordance with various aspects of the applicants' teachings.

FIG. 17 depicts a representation of the seed pulse grown using a sub-harmonic resonator as disclosed herein. The varying amplitude of the seed pulses while operating in the sub-harmonic regime is depicted in this plot. The trace pulse height variation of repeated high then low is due to the subharmonic used being an n=2.

The picopulse laser uses a mode locking to achieve its short pulsewidth. The mode locker is a constricting device which is only fully open for a small fraction of the time it takes a photon to make a round trip in the resonator. So of all the photons circulating and making round trips, only those which arrive at the gate at the right moment will find it fully open, all other photons will experience a loss. Over many round trips this elimination of all but the 'correctly' timed photons results in a shortening of the pulsewidth. All prior literature suggests you drive open the gate once per round trip or even twice per round trip for 2 pulses to be present and so on. The picopulse laser with the sub-harmonic resonator is not run at once per round trip but at once per 2 round trips, hence it is sub-harmonic on a single round trip (e.g., in this example it is one half harmonic).

While the embodiments of the disclosure described herein detail the advantages of implementing the modified pump chamber of a multi-mode, mode-locked operated laser, one skilled in the art would recognize that such advantages may be experiences using other types of lasers and operations, such as, for example, multi-mode, non-mode locked operation.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

While only certain embodiments have been described, it will be understood by those skilled in the art that various changes in form and details may be made therein without departing from the spirit and scope as defined by the appended claims. Those skilled in the art will recognize, or be able to ascertain using no more than routine experimentation, many equivalents to the specific embodiments described specifically herein. Such equivalents are intended to be encompassed in the scope of the appended claims.

The patent, scientific and medical publications referred to herein establish knowledge that was available to those of ordinary skill in the art. The entire disclosures of the issued U.S. patents, published and pending patent applications, and other references cited herein are hereby incorporated by reference.

The invention claimed is:

1. An apparatus for delivery of pulsed treatment radiation comprising:
a pump radiation source generating pumping pulses at a first wavelength,
a wavelength-shifting oscillator defining a resonant cavity comprising a first laser gain material, and
an optical amplifier comprising a second laser gain material that is different from the first laser gain material, wherein the oscillator output wavelength varies in response to controlled temperature changes, wherein the oscillator temperature is controlled to emit a maximum energy amplified output pulse from the optical amplifier at a second wavelength.

2. The apparatus of claim 1, wherein the resonant cavity of the wavelength-shifting oscillator has a round trip time shorter than the duration of the pumping pulses.

3. The apparatus of claim 1, wherein the oscillator output wavelength varies with the peak amplification wavelength of the optical amplifier.

4. The apparatus of claim 1, wherein the oscillator output second wavelength varies so that the amplified output pulse has minimal pulse duration.

5. The apparatus of claim 1, wherein the pumping pulses at the first wavelength are sub nanosecond pulses.

6. The apparatus of claim 1, wherein the oscillator temperature is controlled to range between about 0° C. and about 100° C.

7. The apparatus of claim 1, wherein the oscillator temperature is controlled to range between about 20° C. and about 80° C.

8. The apparatus of claim 1, wherein the oscillator temperature is controlled to range between about 30° C. and about 70° C.

9. The apparatus of claim 1, wherein the wavelength-shifting oscillator operates without use of a modelocker or a Q-switch.

10. The apparatus of claim 1, wherein the wavelength-shifting oscillator emits a subnanosecond pulse.

11. The apparatus of claim 1, wherein a lasing medium of the wavelength-shifting oscillator comprises a neodymium-doped crystal.

12. The apparatus of claim 1, wherein a lasing medium of the wavelength-shifting oscillator comprises a solid state crystal medium selected from the group consisting of neodymium-doped yttrium-aluminum garnet (Nd:YAG) crystals, neodymium-doped pervoskite (Nd:YAP or Nd:YAlO$_3$) crystals, and neodymium-doped yttrium-lithium-fluoride (Nd:YAF) crystals.

13. The apparatus of claim 1, wherein a lasing medium of the wavelength-shifting oscillator comprises a neodymium-doped, vanadate (Nd:YVO$_4$) crystal.

14. The apparatus of claim 1 further comprising a polarizer embedded within the wavelength-shifting oscillator.

15. The apparatus of claim 1, wherein a lasing medium of the wavelength-shifting oscillator is a polarizing medium.

16. The apparatus of claim 1 further comprising a frequency-doubling crystal.

17. The apparatus of claim 16, wherein the frequency-doubling crystal comprises a nonlinear crystal material.

18. The apparatus of claim 16, wherein the frequency-doubling waveguide comprises a lithium triborate (LiB$_3$O$_5$) material or a KTP material.

19. The apparatus of claim 1, wherein the pump radiation source is a mode-locked laser.

20. The apparatus of claim 19, wherein the mode-locked laser comprises an alexandrite laser.

21. The apparatus of claim 19, wherein the mode-locked laser generates pulsed laser energy having at least about 100 mJ/pulse.

22. The apparatus of claim 1 further comprising a treatment beam delivery system configured to apply a treatment beam in the form of the second wavelength to a target tissue.

23. The apparatus of claim 1, wherein the wavelength-shifting oscillator emits a laser energy having at least about 100 mJ/pulse.

24. The apparatus of claim 1 further comprising a second harmonic generator, wherein the pulsed treatment radiation at the second wavelength from the optical amplifier is transmitted through the second harmonic generator and is converted to a third wavelength.

25. The apparatus of claim 24, wherein the wavelength-shifting oscillator followed by the optical amplifier and the second harmonic generator emits a laser energy having at least about 100 mJ/pulse.

26. A method of delivering pulsed treatment radiation comprising:
   generating pumping pulses, using a pump radiation source, wherein one or more pumping pulses are at a first wavelength and a first pulse duration;
   transmitting the pumping pulses to a wavelength-shifting oscillator and then from the oscillator to an optical amplifier, the oscillator comprising a first laser gain material;
   varying the temperature of the first laser gain material such that the oscillator output wavelength varies;
   controlling the temperature of the first laser gain material to emit a maximum energy output from the optical amplifier; and
   emitting pulsed treatment radiation at a second wavelength from the optical amplifier, the optical amplifier comprising a second laser gain material that is different from the first laser gain material.

27. The method of claim 26 further comprising applying a treatment beam to a patient, the treatment beam comprising pulsed treatment radiation.

28. The method of claim 26 wherein the pulsed treatment radiation comprises a subnanosecond pulse.

29. The method of claim 26 further comprising applying one or more subnanosecond pulses to a patient.

30. The method of claim 26 further comprising applying one or more subnanosecond pulses to a tattoo or a region of skin pigmentation.

31. The method of claim 26, wherein the optical amplifier emits a laser energy having at least about 100 mJ/pulse.

32. The method of claim 26, further comprising a second harmonic generator, wherein the pulsed treatment radiation at the second wavelength from the optical amplifier is transmitted through the second harmonic generator and is converted to a third wavelength.

33. The method of claim 32, wherein the wavelength-shifting oscillator followed by the optical amplifier and the second harmonic generator emits a laser energy having at least about 100 mJ/pulse.

34. A system for generating picosecond pulses, the system consisting essentially of:
   a pump radiation source generating pumping pulses at a first wavelength,
   a wavelength-shifting oscillator defining a resonant cavity comprising a first laser gain material, and
   an optical amplifier comprising a second laser gain material that is different from the first laser gain material, wherein the oscillator output wavelength varies in response to controlled temperature changes, wherein the oscillator temperature is controlled to emit a maximum energy amplified output pulse from the optical amplifier at a second wavelength.

* * * * *